US009803008B2

(12) United States Patent
Eriksson et al.

(10) Patent No.: US 9,803,008 B2
(45) Date of Patent: Oct. 31, 2017

(54) METHOD OF TREATING DIABETIC NEPHROPATHY BY ADMINISTERING ANTIBODIES TO VASCULAR ENDOTHELIAL GROWTH FACTOR B (VEGF-B)

(71) Applicants: CSL LIMITED, Parkville, Victoria (AU); B-CREATIVE SWEDEN AB, Balsta (SE)

(72) Inventors: Ulf Eriksson, Stockholm (SE); Annelie Falkevall, Stockholm (SE); Annika Mehlem, Stockholm (SE)

(73) Assignees: CSL Limited, Parkville, Victoria (AU); B-CREATIVE SWEDEN AB, Balsta (SE)

( * ) Notice: Subject to any disclaimer, the term of this patent is extended or adjusted under 35 U.S.C. 154(b) by 0 days.

(21) Appl. No.: 15/039,606

(22) PCT Filed: Nov. 28, 2014

(86) PCT No.: PCT/AU2014/050387
§ 371 (c)(1),
(2) Date: May 26, 2016

(87) PCT Pub. No.: WO2015/077845
PCT Pub. Date: Jun. 4, 2015

(65) Prior Publication Data
US 2017/0037119 A1    Feb. 9, 2017

(30) Foreign Application Priority Data
Nov. 28, 2013 (AU) .................... 2013904595

(51) Int. Cl.
| C07K 16/22 | (2006.01) |
| A61K 31/713 | (2006.01) |
| A61K 39/395 | (2006.01) |
| A61K 45/06 | (2006.01) |
| C12N 15/113 | (2010.01) |
| A61K 39/00 | (2006.01) |

(52) U.S. Cl.
CPC ........... *C07K 16/22* (2013.01); *A61K 31/713* (2013.01); *A61K 39/3955* (2013.01); *A61K 45/06* (2013.01); *C12N 15/1136* (2013.01); *A61K 2039/505* (2013.01); *C07K 2317/24* (2013.01); *C07K 2317/56* (2013.01); *C07K 2317/76* (2013.01); *C12N 2320/30* (2013.01)

(58) Field of Classification Search
CPC   C07K 16/22; C07K 2317/24; C07K 2317/56; C07K 2317/76; C12N 15/1136; C12N 2320/30; A61K 45/06; A61K 39/3955; A61K 31/713; A61K 2039/505
See application file for complete search history.

(56) References Cited

U.S. PATENT DOCUMENTS

| 4,676,980 A | 6/1987 | Segal et al. |
| 4,816,397 A | 3/1989 | Boss et al. |
| 4,816,567 A | 3/1989 | Cabilly et al. |
| 5,225,539 A | 7/1993 | Winter |
| 5,260,203 A | 11/1993 | Ladner et al. |
| 5,530,101 A | 6/1996 | Queen et al. |
| 5,565,332 A | 10/1996 | Hoogenboom et al. |
| 5,807,715 A | 9/1998 | Morrison et al. |
| 5,837,821 A | 11/1998 | Wu |
| 5,885,793 A | 3/1999 | Griffiths et al. |
| 6,054,297 A | 4/2000 | Carter et al. |
| 6,113,898 A | 9/2000 | Anderson et al. |
| 6,204,023 B1 | 3/2001 | Robinson et al. |
| 6,248,516 B1 | 6/2001 | Winter et al. |
| 6,291,158 B1 | 9/2001 | Winter et al. |
| 6,300,064 B1 | 10/2001 | Knappik et al. |
| 6,331,415 B1 | 12/2001 | Cabilly et al. |
| 7,030,146 B2 | 4/2006 | Baynes et al. |
| 7,217,797 B2 | 5/2007 | Hinton et al. |
| 7,217,798 B2 | 5/2007 | Hinton et al. |
| 7,250,297 B1 | 7/2007 | Beste et al. |
| 7,270,969 B2 | 9/2007 | Watt et al. |
| 7,566,771 B1 | 7/2009 | Adair et al. |
| 7,732,578 B2 | 6/2010 | Foote |
| 2005/0037000 A1 | 2/2005 | Stavenhagen et al. |
| 2007/0224633 A1 | 9/2007 | Skerra et al. |
| 2008/0139791 A1 | 6/2008 | Lipovsek et al. |
| 2009/0041770 A1 | 2/2009 | Chamberlain et al. |

FOREIGN PATENT DOCUMENTS

| EP | 0569141 A2 | 10/1993 |
| WO | 9404678 | 3/1994 |
| WO | 9749805 | 12/1997 |
| WO | 9932619 | 7/1999 |
| WO | 9945110 | 9/1999 |
| WO | 9949029 | 9/1999 |

(Continued)

OTHER PUBLICATIONS

International Preliminary Report on Patentability together with the Written Opinion from related International Application No. PCT/AU2014/050387 dated May 31, 2016.
International Search Report and Written Opinion dated Jan. 15, 2015 issued in PCT/AU2014/050387.
Hagberg, Carolina E. et al., "Targeting VEGF-B as a novel treatment for insulin resistance and type 2 diabetes", Nature (Oct. 18, 2012), vol. 490, pp. 426-430.
Yang, Keun Suk et al., "Vascular Endothelial Growth Factor-Receptor 1 Inhibition Aggravates Diabetic Nephropathy through eNOS Signaling Pathway in db/db Mice", PLOS ONE (Apr. 23, 2014), vol. 9, No. 4, p. e94540.
Breyer, Matthew D. et al., "Mouse Models of Diabetic Nephropathy", Journal of the American Society of Nephrology (2005), vol. 16, pp. 27-45.

(Continued)

*Primary Examiner* — Robert Landsman
(74) *Attorney, Agent, or Firm* — Scully Scott Murphy and Presser; Frank Digiglio

(57) ABSTRACT

The present disclosure provides a method of treating diabetic nephropathy in a subject suffering from diabetic nephropathy, the method comprising administering to the subject a compound that inhibits VEGF-B signalling.

11 Claims, 22 Drawing Sheets

(56) References Cited

FOREIGN PATENT DOCUMENTS

| WO | 9953050 | 10/1999 |
|---|---|---|
| WO | 0034317 | 6/2000 |
| WO | 0134815 A1 | 5/2001 |
| WO | 02088171 A2 | 11/2002 |
| WO | 2004108158 A1 | 12/2004 |
| WO | 2005056764 A2 | 6/2005 |
| WO | 2005118629 A1 | 12/2005 |
| WO | 2006012688 A1 | 2/2006 |
| WO | 2007019620 A1 | 2/2007 |
| WO | 2007117410 A2 | 10/2007 |
| WO | 2010080238 A1 | 7/2010 |
| WO | 2011107595 A1 | 3/2011 |
| WO | WO 2014/045266 A1 | 3/2014 |

OTHER PUBLICATIONS

Sharma, Kumar et al., "Diabetic kidney disease in the db/db mouse", American Journal of Physiology Renal Physiology (2003), vol. 284, pp. F1138-F1144.
De Vriese, A. S. et al., "Antibodies against Vascular Endothelial Growth Factor Improve Early Renal Dysfunction in Experimental Diabetes", Journal of American Society of Nephrology (2001), vol. 12, pp. 993-1000.
Schrijvers, Bieke F. et al., "The role of vascular endothelial growth factor (VEGF) in renal pathophysiology", Kidney International (2004), vol. 65, pp. 2003-2017.
Schena, Francesco P. et al., "Pathogenetic Mechanisms of Diabetic Nephropathy", Journal of the American Society of Nephrology (2005), vol. 16, pp. S30-S33.
Al-Lazikani et al., :Standard Conformations for the Canonical Structures of Immunoglobulins; J Mol Biol 273: 927-948, 1997.
Chothia and Lesk J., "Canonical Structures for the Hypervariable Regions of Immunoglobulins"; Mol Biol. 196: 901-917, 1987.
Chothia et al., "Conformations of Immunoglobulin Hypervariable Regions"; Nature 342, 877-883, 1989.
Jones et al., "A Method for Rapid, Ligation-Independent Reformatting of Recombinant Monoclonal Antibodies"; J Immunol Methods. 354:85-90, 2010.
Jostock et al., Rapid Generation of Functional Human IgG Antibodies Derived From Fab-on-phage Display Libraries; J Immunol Methods, 289: 65-80, 2004.
Kimmel et al., Diabetic Nephropathy in Type 2 Diabetes Acta Diabetologica, 29, 142-148, 1992.
Kosugi et al , "Soluble Flt-1 Gene Therapy Ameliorates Albuminuria but Accelerates Tubulointerstitial Injury in Diabetic Mice"; (Am J Physiol Renal Physiol 298: F609-F616, 2010).
Largaespada et al, "The Activity of an ABL-MYC Retrovirus in Fibroblast Cell Lines and in Lymphocytes"; Curr. Top. Microbiol. Immunol, 166, 91-96. 1990.
Lonberg et al., "Antigen Specific Human Antibodies from Mice comprising Four Distinct Genetic Modifications"; Nature 368 (1994): 856-859).
Milstein; "Continuous Cultures of Fused Cells Secreting Antibody of Predefined Specificity"; Nature 256, 495-497, 1975.
Nakagawa et al.; "Abnormal Angiogenesis in Diabetic Nephropathy"; Diabetes, 58, p. 1471-8, 2009.
Novotny et al., "A Soluble, Single-Chain T-cell Receptor Fragment Endowed with Antigen-combining Properties"; Proc Mall Acad Sci USA 88: 8646-8650, 1991.
Rees and Alcolado, "Animal Models of Diabetes Mellitus"; Diabet. Med. 22, 359-370, 2005.
Shalaby et al.; "Development of Humanized Bispecific Antibodies Reactive with Cytotoxic Lymphocytes and Tumor Cells Overexpressing the HER2 Protooncogene"; J. Exp. Med., 175: 217-225, 1992.

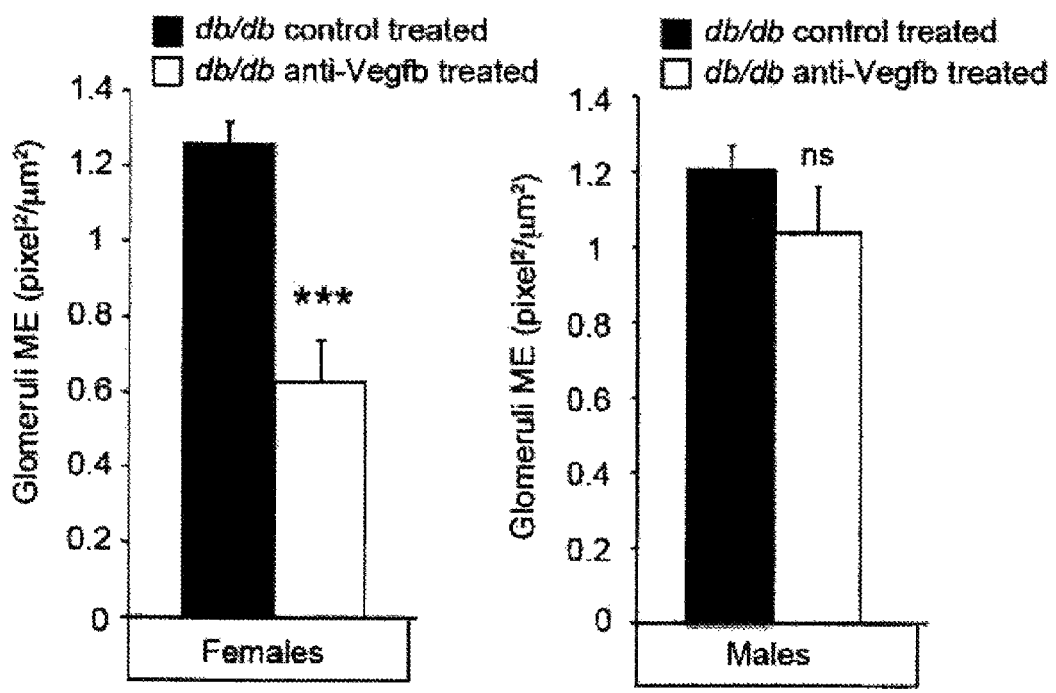
FIGURE 23A  FIGURE 23B
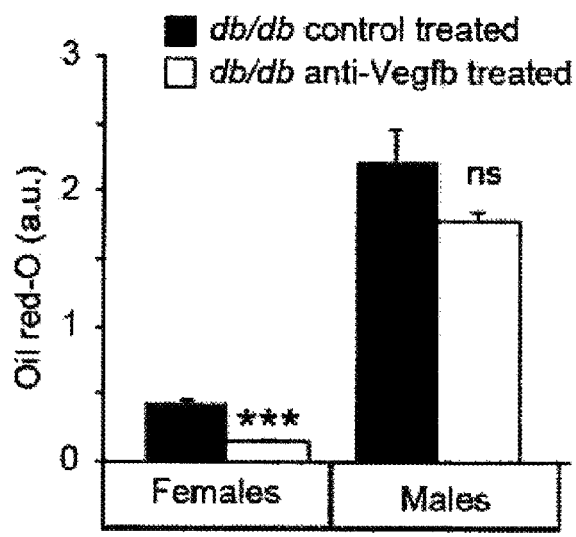
FIGURE 24

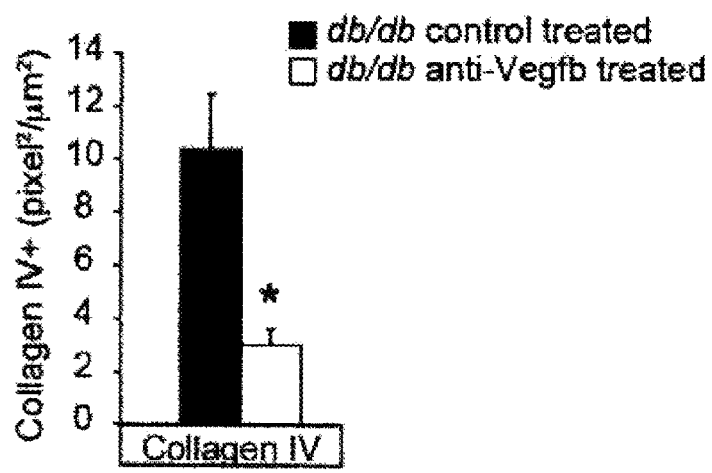
FIGURE 26A
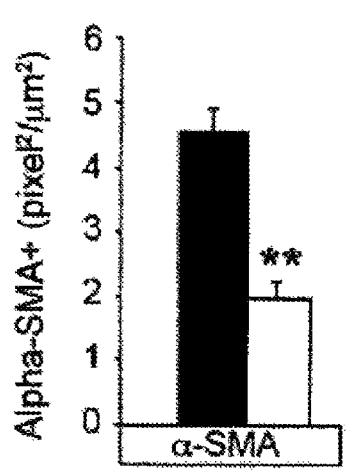 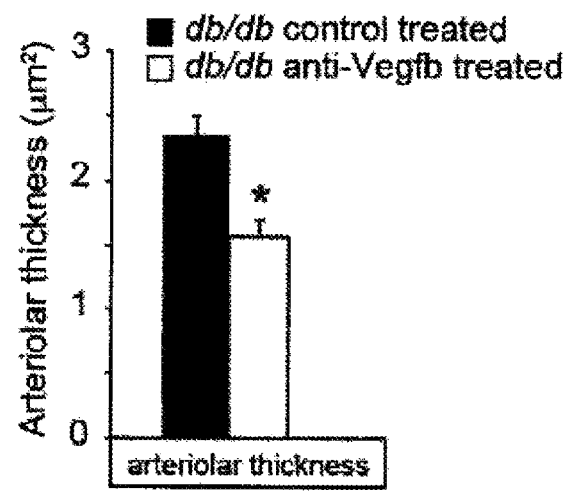
FIGURE 26B
FIGURE 26C

SEQUENCE LISTING

```
<160> NUMBER OF SEQ ID NOS: 46

<210> SEQ ID NO 1
<211> LENGTH: 207
<212> TYPE: PRT
<213> ORGANISM: Homo sapiens
<220> FEATURE:
<221> NAME/KEY: SIGNAL
<222> LOCATION: (1)..(21)
<223> OTHER INFORMATION: Signal sequence

<400> SEQUENCE: 1

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
    130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205

<210> SEQ ID NO 2
<211> LENGTH: 188
<212> TYPE: PRT
<213> ORGANISM: Homo sapiens
<220> FEATURE:
<221> NAME/KEY: SIGNAL
<222> LOCATION: (1)..(21)
<223> OTHER INFORMATION: Signal sequence

<400> SEQUENCE: 2

Met Ser Pro Leu Leu Arg Arg Leu Leu Leu Ala Ala Leu Leu Gln Leu
1               5                   10                  15
```

```
Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Pro Leu Thr Val Glu Leu Met Gly Thr Val
50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
130                 135                 140

Cys Thr Gln His His Gln Arg Pro Asp Pro Arg Thr Cys Arg Arg Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
                180                 185

<210> SEQ ID NO 3
<211> LENGTH: 119
<212> TYPE: PRT
<213> ORGANISM: artificial
<220> FEATURE:
<223> OTHER INFORMATION: amino acid sequence from a VH of antibody 2H10

<400> SEQUENCE: 3

Val Gln Leu Gln Gln Pro Gly Thr Glu Leu Val Lys Pro Gly Ala Ser
1               5                   10                  15

Val Lys Leu Ser Cys Lys Ala Ser Gly Tyr Thr Phe Thr Gly Phe Trp
            20                  25                  30

Ile His Trp Val Lys Gln Arg Pro Gly Gln Gly Leu Glu Trp Ile Gly
        35                  40                  45

His Ile Asn Pro Gly Asn Gly Gly Thr Asn Tyr Asn Glu Lys Phe Lys
    50                  55                  60

Arg Met Ala Thr Leu Thr Val Asp Lys Ser Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Ser Tyr Ser Asn Tyr Val Arg Ala Met Asp Tyr Trp Gly Gln Gly
            100                 105                 110

Thr Ser Val Thr Val Ser Ser
        115

<210> SEQ ID NO 4
<211> LENGTH: 106
<212> TYPE: PRT
<213> ORGANISM: artificial
<220> FEATURE:
<223> OTHER INFORMATION: amino acid sequence from a VL of antibody 2H10

<400> SEQUENCE: 4

Ile Gln Met Thr Gln Thr Thr Ser Ser Leu Ser Ala Ser Leu Gly Asp
```

```
            1               5                  10                 15
          Arg Val Thr Ile Ser Cys Arg Ala Ser Gln Asp Ile Ser Asn Phe Leu
                          20                 25                 30

Asn Trp Tyr Gln Gln Lys Pro Asp Gly Thr Val Lys Leu Leu Ile Tyr
                          35                 40                 45

Tyr Thr Ser Thr Leu His Ser Gly Val Pro Ser Arg Phe Ser Gly Ser
                  50                 55                 60

Gly Ser Gly Thr Asp Tyr Ser Leu Thr Ile Ser Asn Leu Glu Gln Glu
          65                  70                 75                 80

Asp Ile Ala Thr Tyr Phe Cys Gln Gln Gly Lys Thr Leu Pro Pro Thr
                          85                 90                 95

Phe Gly Gly Gly Thr Lys Leu Glu Ile Lys
                          100                105

<210> SEQ ID NO 5
<211> LENGTH: 119
<212> TYPE: PRT
<213> ORGANISM: artificial
<220> FEATURE:
<223> OTHER INFORMATION: amino acid sequence from a VH of a humanized
      form of antibody 2H10

<400> SEQUENCE: 5

Val Gln Leu Val Gln Ser Gly Ala Glu Val Lys Lys Pro Gly Ala Ser
          1               5                  10                 15

Val Lys Val Ser Cys Lys Ala Ser Gly Tyr Thr Phe Thr Gly Phe Trp
                          20                 25                 30

Ile His Trp Val Arg Gln Ala Pro Gly Gln Gly Leu Glu Trp Met Gly
                          35                 40                 45

His Ile Asn Pro Gly Asn Gly Gly Thr Asn Tyr Asn Glu Lys Phe Lys
                  50                 55                 60

Arg Arg Val Thr Met Thr Arg Asp Lys Ser Ile Ser Thr Ala Tyr Met
          65                  70                 75                 80

Glu Leu Ser Arg Leu Arg Ser Asp Asp Thr Ala Val Tyr Tyr Cys Ala
                          85                 90                 95

Arg Ser Tyr Ser Asn Tyr Val Arg Ala Met Asp Tyr Trp Gly Gln Gly
                          100                105                110

Thr Leu Val Thr Val Ser Ser
                  115

<210> SEQ ID NO 6
<211> LENGTH: 107
<212> TYPE: PRT
<213> ORGANISM: artificial
<220> FEATURE:
<223> OTHER INFORMATION: amino acid sequence of a VL of a humanized
      form of antibody 2H10

<400> SEQUENCE: 6

Asp Ile Gln Met Thr Gln Ser Pro Ser Ser Leu Ser Ala Ser Val Gly
          1               5                  10                 15

Asp Arg Val Thr Ile Thr Cys Arg Ala Ser Gln Asp Ile Ser Asn Phe
                          20                 25                 30

Leu Asn Trp Tyr Gln Gln Lys Pro Gly Lys Ala Pro Lys Leu Leu Ile
                          35                 40                 45

Tyr Tyr Thr Ser Thr Leu His Ser Gly Val Pro Ser Arg Phe Ser Gly
                  50                 55                 60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Gly Lys Thr Leu Pro Pro
                    85                  90                  95

Thr Phe Gly Gly Gly Thr Lys Val Glu Ile Lys
                100                 105

<210> SEQ ID NO 7
<211> LENGTH: 116
<212> TYPE: PRT
<213> ORGANISM: artificial
<220> FEATURE:
<223> OTHER INFORMATION: amino acid sequence from a VH of antibody 4E12

<400> SEQUENCE: 7

Val Gln Pro Gln Gln Pro Gly Ala Glu Leu Val Lys Pro Gly Ala Ser
1               5                   10                  15

Val Lys Met Ser Cys Lys Ala Ser Gly Asp Thr Phe Thr Asn Ser Trp
                20                  25                  30

Ile Gly Trp Val Thr Gln Arg Pro Gly Gln Gly Leu Glu Trp Ile Gly
            35                  40                  45

Asp Ile Phe Pro Gly Ser Gly His Thr Asn Tyr Asn Glu Lys Phe Lys
        50                  55                  60

Asn Arg Ala Thr Leu Thr Val Asp Thr Ser Ser Ser Thr Ala Tyr Met
65                  70                  75                  80

Leu Leu Ser Ser Leu Thr Ser Asp Asp Ser Ala Val Tyr Tyr Cys Val
                85                  90                  95

Ile Glu Asn Tyr Ala Trp Phe Ala Tyr Trp Gly Gln Gly Thr Leu Val
                100                 105                 110

Thr Val Ser Ala
        115

<210> SEQ ID NO 8
<211> LENGTH: 107
<212> TYPE: PRT
<213> ORGANISM: artificial
<220> FEATURE:
<223> OTHER INFORMATION: amino acid sequence of a VL of antibody 4E12

<400> SEQUENCE: 8

Asp Ile Val Met Thr Gln Ser Gln Lys Phe Met Ser Ser Ser Val Gly
1               5                   10                  15

Asp Arg Val Ser Val Thr Cys Lys Ala Ser Gln Asn Val Asn Thr Asn
                20                  25                  30

Val Ala Trp Tyr Gln Gln Lys Gln Gly Gln Ser Pro Arg Pro Leu Ile
            35                  40                  45

Tyr Ser Ala Ser Ser Arg Cys Ser Gly Val Pro Asp Arg Phe Thr Gly
        50                  55                  60

Ser Gly Phe Gly Thr Asp Phe Thr Leu Thr Ile Ser Asn Val Gln Ser
65                  70                  75                  80

Glu Asp Leu Ala Glu Tyr Phe Cys Gln Gln Tyr His Ser Phe Pro Leu
                85                  90                  95

Thr Phe Gly Ala Gly Ala Lys Leu Asp Leu Lys
                100                 105

<210> SEQ ID NO 9
<211> LENGTH: 118
<212> TYPE: PRT
<213> ORGANISM: artificial
<220> FEATURE:
```

<223> OTHER INFORMATION: amino acid sequence from a VH of antibody 2F5

<400> SEQUENCE: 9

Val Gln Leu Gln Gln Ser Gly Pro Glu Leu Val Lys Pro Gly Thr Ser
1               5                   10                  15

Val Arg Ile Ser Cys Lys Ala Ser Gly Tyr Thr Phe Thr Phe Tyr
            20                  25                  30

Ile His Trp Val Lys Gln Arg Pro Gly Gln Gly Leu Glu Trp Ile Gly
        35                  40                  45

Trp Phe Tyr Pro Gly Asn Val Asn Thr Asn Tyr Asn Glu Lys Leu Lys
    50                  55                  60

Gly Lys Ala Thr Leu Thr Ala Asp Lys Ser Ser Ser Ala Ala Tyr Leu
65                  70                  75                  80

Gln Leu Asn Ser Leu Thr Ser Glu Asp Ser Ala Val Tyr Phe Cys Thr
                85                  90                  95

Arg Ser Pro Tyr Tyr Gly Tyr Val Phe Asp Tyr Trp Gly Gln Gly Thr
            100                 105                 110

Thr Leu Thr Val Ser Ser
            115

<210> SEQ ID NO 10
<211> LENGTH: 107
<212> TYPE: PRT
<213> ORGANISM: artificial
<220> FEATURE:
<223> OTHER INFORMATION: amino acid sequence of a VL of antibody 2F5

<400> SEQUENCE: 10

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Ser Leu Thr
                85                  90                  95

Phe Gly Ala Gly Ala Thr Lys Leu Glu Leu Lys
            100                 105

<210> SEQ ID NO 11
<211> LENGTH: 33
<212> TYPE: DNA
<213> ORGANISM: Artificial Sequence
<220> FEATURE:
<223> OTHER INFORMATION: Nucleotide sequence of 2H10 VL CDR1

<400> SEQUENCE: 11
agggcaagtc aggacattag caatttttta aac                              33

<210> SEQ ID NO 12
<211> LENGTH: 21
<212> TYPE: DNA
<213> ORGANISM: Artificial Sequence
<220> FEATURE:
<223> OTHER INFORMATION: Nucleotide sequence of 2H10 VL CDR2

<400> SEQUENCE: 12
tacacatcaa cattacactc a                                            21

<210> SEQ ID NO 13
<211> LENGTH: 27
<212> TYPE: DNA
<213> ORGANISM: Artificial Sequence
<220> FEATURE:
<223> OTHER INFORMATION: Nucleotide sequence of 2H10 VL CDR3

<400> SEQUENCE: 13
caacagggta aaacgcttcc tcccacg                                      27

<210> SEQ ID NO 14
<211> LENGTH: 30
<212> TYPE: DNA
<213> ORGANISM: Artificial Sequence
<220> FEATURE:
<223> OTHER INFORMATION: Nucleotide sequence of 2H10 VH CDR1

<400> SEQUENCE: 14
ggctacactt tcactggctt ctggatacac                                   30

<210> SEQ ID NO 15
<211> LENGTH: 51
<212> TYPE: DNA
<213> ORGANISM: Artificial Sequence
<220> FEATURE:
<223> OTHER INFORMATION: Nucleotide sequence of 2H10 VH CDR2

<400> SEQUENCE: 15
catattaatc ctggcaatgg tggcactaac tacaatgaga agttcaagag a            51

<210> SEQ ID NO 16
<211> LENGTH: 33
<212> TYPE: DNA
<213> ORGANISM: Artificial Sequence
<220> FEATURE:
<223> OTHER INFORMATION: Nucleotide sequence of 2H10 VH CDR3

<400> SEQUENCE: 16
tcctatagta actacgtgcg ggctatggac tac                               33

<210> SEQ ID NO 17
<211> LENGTH: 11
<212> TYPE: PRT
<213> ORGANISM: Artificial Sequence
<220> FEATURE:
<223> OTHER INFORMATION: Amino acid sequence of 2H10 VL CDR1

<400> SEQUENCE: 17

Arg Ala Ser Gln Asp Ile Ser Asn Phe Leu Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: amino acid sequence of 2H10 VL CDR2

<400> SEQUENCE: 18

Tyr Thr Ser Thr Leu His Ser
1               5

```
<210> SEQ ID NO 19
<211> LENGTH: 9
<212> TYPE: PRT
<213> ORGANISM: Artificial Sequence
<220> FEATURE:
<223> OTHER INFORMATION: amino acid sequence of 2H10 VL CDR3

<400> SEQUENCE: 19

Gln Gln Gly Lys Thr Leu Pro Pro Thr
1               5

<210> SEQ ID NO 20
<211> LENGTH: 10
<212> TYPE: PRT
<213> ORGANISM: Artificial Sequence
<220> FEATURE:
<223> OTHER INFORMATION: amino acid sequence of 2H10 VH CDR1

<400> SEQUENCE: 20

Gly Tyr Thr Phe Thr Gly Phe Trp Ile His
1               5                   10

<210> SEQ ID NO 21
<211> LENGTH: 17
<212> TYPE: PRT
<213> ORGANISM: Artificial Sequence
<220> FEATURE:
<223> OTHER INFORMATION: amino acid sequence of 2H10 VH CDR2

<400> SEQUENCE: 21

His Ile Asn Pro Gly Asn Gly Gly Thr Asn Tyr Asn Glu Lys Phe Lys
1               5                   10                  15

Arg

<210> SEQ ID NO 22
<211> LENGTH: 11
<212> TYPE: PRT
<213> ORGANISM: Artificial Sequence
<220> FEATURE:
<223> OTHER INFORMATION: amino acid sequence of 2H10 VH CDR3

<400> SEQUENCE: 22

Ser Tyr Ser Asn Tyr Val Arg Ala Met Asp Tyr
1               5                   10

<210> SEQ ID NO 23
<211> LENGTH: 33
<212> TYPE: DNA
<213> ORGANISM: Artificial Sequence
<220> FEATURE:
<223> OTHER INFORMATION: nucleotide sequence of 2F5 VL CDR1

<400> SEQUENCE: 23
aaggccagtc aggatgtggg tactgctgta gcc                              33

<210> SEQ ID NO 24
<211> LENGTH: 21
<212> TYPE: DNA
<213> ORGANISM: Artificial Sequence
<220> FEATURE:
<223> OTHER INFORMATION: nucleotide sequence of 2F5 VL CDR2

<400> SEQUENCE: 24
tgggcatcca cccggcacac t                                           21

<210> SEQ ID NO 25
```

```
<211> LENGTH: 24
<212> TYPE: DNA
<213> ORGANISM: Artificial Sequence
<220> FEATURE:
<223> OTHER INFORMATION: nucleotide sequence of 2F5 VL CDR3

<400> SEQUENCE: 25
caacaatata gcagctctct cacg                                          24

<210> SEQ ID NO 26
<211> LENGTH: 30
<212> TYPE: DNA
<213> ORGANISM: Artificial Sequence
<220> FEATURE:
<223> OTHER INFORMATION: nucleotide sequence of 2F5 VH CDR1

<400> SEQUENCE: 26
ggctacacct tcacaacctt ctatatacac                                    30

<210> SEQ ID NO 27
<211> LENGTH: 51
<212> TYPE: DNA
<213> ORGANISM: Artificial Sequence
<220> FEATURE:
<223> OTHER INFORMATION: nucleotide sequence of 2F5 VH CDR2

<400> SEQUENCE: 27
tggttttatc ctggaaatgt taataccaac tacaatgaga agctcaaggg c             51

<210> SEQ ID NO 28
<211> LENGTH: 30
<212> TYPE: DNA
<213> ORGANISM: Artificial Sequence
<220> FEATURE:
<223> OTHER INFORMATION: nucleotide sequence of 2F5 VH CDR3

<400> SEQUENCE: 28
tccccttact acggctacgt ttttgactac                                    30

<210> SEQ ID NO 29
<211> LENGTH: 11
<212> TYPE: PRT
<213> ORGANISM: Artificial Sequence
<220> FEATURE:
<223> OTHER INFORMATION: amino acid sequence of 2F5 VL CDR1

<400> SEQUENCE: 29

Lys Ala Ser Gln Asp Val Gly Thr Ala Val Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: amino acid sequence of 2F5 VL CDR2

<400> SEQUENCE: 30

Trp Ala Ser Thr Arg His Thr
1               5

<210> SEQ ID NO 31
<211> LENGTH: 8
<212> TYPE: PRT
<213> ORGANISM: Artificial Sequence
<220> FEATURE:
<223> OTHER INFORMATION: amino acid sequence of 2F5 VL CDR3
```

-continued

```
<400> SEQUENCE: 31

Gln Gln Tyr Ser Ser Ser Leu Thr
1               5

<210> SEQ ID NO 32
<211> LENGTH: 10
<212> TYPE: PRT
<213> ORGANISM: Artificial Sequence
<220> FEATURE:
<223> OTHER INFORMATION: amino acid sequence of 2F5 VH CDR1

<400> SEQUENCE: 32

Gly Tyr Thr Phe Thr Thr Phe Tyr Ile His
1               5                   10

<210> SEQ ID NO 33
<211> LENGTH: 17
<212> TYPE: PRT
<213> ORGANISM: Artificial Sequence
<220> FEATURE:
<223> OTHER INFORMATION: amino acid sequence of 2F5 VH CDR2

<400> SEQUENCE: 33

Trp Phe Tyr Pro Gly Asn Val Asn Thr Asn Tyr Asn Glu Lys Leu Lys
1               5                   10                  15

Gly

<210> SEQ ID NO 34
<211> LENGTH: 10
<212> TYPE: PRT
<213> ORGANISM: Artificial Sequence
<220> FEATURE:
<223> OTHER INFORMATION: amino acid sequence of 2F5 VH CDR3

<400> SEQUENCE: 34

Ser Pro Tyr Tyr Gly Tyr Val Phe Asp Tyr
1               5                   10

<210> SEQ ID NO 35
<211> LENGTH: 33
<212> TYPE: DNA
<213> ORGANISM: Artificial Sequence
<220> FEATURE:
<223> OTHER INFORMATION: nucleotide sequence of 4E12 VL CDR1

<400> SEQUENCE: 35
aaggccagtc agaatgtgaa cactaatgta gcc                                33

<210> SEQ ID NO 36
<211> LENGTH: 21
<212> TYPE: DNA
<213> ORGANISM: Artificial Sequence
<220> FEATURE:
<223> OTHER INFORMATION: nucleotide sequence of 4E12 VL CDR2

<400> SEQUENCE: 36
tcggcatcct cccggtgcag t                                             21

<210> SEQ ID NO 37
<211> LENGTH: 27
<212> TYPE: DNA
<213> ORGANISM: Artificial Sequence
<220> FEATURE:
<223> OTHER INFORMATION: nucleotide sequence of 4E12 VL CDR3
```

```
<400> SEQUENCE: 37
cagcaatatc acagctttcc gctcacg                                        27

<210> SEQ ID NO 38
<211> LENGTH: 30
<212> TYPE: DNA
<213> ORGANISM: Artificial Sequence
<220> FEATURE:
<223> OTHER INFORMATION: nucleotide sequence of 4E12 VH CDR1

<400> SEQUENCE: 38
ggcgacacct tcaccaactc ctggataggc                                     30

<210> SEQ ID NO 39
<211> LENGTH: 51
<212> TYPE: DNA
<213> ORGANISM: Artificial Sequence
<220> FEATURE:
<223> OTHER INFORMATION: nucleotide sequence of 4E12 VH CDR2

<400> SEQUENCE: 39 gatattttc ctgggagtgg tcatactaac tacaatgaga agttcaagaa c              51

<210> SEQ ID NO 40
<211> LENGTH: 24
<212> TYPE: DNA
<213> ORGANISM: Artificial Sequence
<220> FEATURE:
<223> OTHER INFORMATION: nucleotide sequence of 4E12 VH CDR3

<400> SEQUENCE: 40
gagaattatg cctggtttgc ttat                                           24

<210> SEQ ID NO 41
<211> LENGTH: 11
<212> TYPE: PRT
<213> ORGANISM: Artificial Sequence
<220> FEATURE:
<223> OTHER INFORMATION: amino acid sequence of 4E12 VL CDR1

<400> SEQUENCE: 41

Lys Ala Ser Gln Asn Val Asn Thr Asn Val Ala
1               5                   10

<210> SEQ ID NO 42
<211> LENGTH: 7
<212> TYPE: PRT
<213> ORGANISM: Artificial Sequence
<220> FEATURE:
<223> OTHER INFORMATION: amino acid sequence of 4E12 VL CDR2

<400> SEQUENCE: 42

Ser Ala Ser Ser Arg Cys Ser
1               5

<210> SEQ ID NO 43
<211> LENGTH: 9
<212> TYPE: PRT
<213> ORGANISM: Artificial Sequence
<220> FEATURE:
<223> OTHER INFORMATION: amino acid sequence of 4E12 VL CDR3

<400> SEQUENCE: 43

Gln Gln Tyr His Ser Phe Pro Leu Thr
1               5
```

```
<210> SEQ ID NO 44
<211> LENGTH: 10
<212> TYPE: PRT
<213> ORGANISM: Artificial Sequence
<220> FEATURE:
<223> OTHER INFORMATION: amino acid sequence of 4E12 VH CDR1

<400> SEQUENCE: 44

Gly Asp Thr Phe Thr Asn Ser Trp Ile Gly
1               5                   10

<210> SEQ ID NO 45
<211> LENGTH: 17
<212> TYPE: PRT
<213> ORGANISM: Artificial Sequence
<220> FEATURE:
<223> OTHER INFORMATION: amino acid sequence of 4E12 VH CDR2

<400> SEQUENCE: 45

Asp Ile Phe Pro Gly Ser Gly His Thr Asn Tyr Asn Glu Lys Phe Lys
1               5                   10                  15

Asn

<210> SEQ ID NO 46
<211> LENGTH: 8
<212> TYPE: PRT
<213> ORGANISM: Artificial Sequence
<220> FEATURE:
<223> OTHER INFORMATION: amino acid sequence of 4E12 VH CDR3

<400> SEQUENCE: 46

Glu Asn Tyr Ala Trp Phe Ala Tyr
1               5
```

METHOD OF TREATING DIABETIC NEPHROPATHY BY ADMINISTERING ANTIBODIES TO VASCULAR ENDOTHELIAL GROWTH FACTOR B (VEGF-B)

RELATED APPLICATION DATA

The present application claims priority from Australian Patent Application No. 2013904595 filed on 28 Nov. 2013 and entitled "Method of treating nephropathy", now Australian Patent Publication No. AU2014354588AA. The entire contents of that application are incorporated by reference.

SEQUENCE LISTING

The present application is filed with a Sequence Listing in electronic form. The entire contents of the Sequence Listing are hereby incorporated by reference.

FIELD

The present application relates to a method for treating or preventing nephropathy.

INTRODUCTION

Nephropathy

Nephropathy is a class of disorders characterized by damage to a kidney and encompasses nephritis (inflammatory kidney disease) and nephrosis (non-inflammatory kidney disease). Causes of nephropathy include chronic conditions (including systemic lupus erythematosus, diabetes mellitus and high blood pressure (hypertension)), deposition of IgA antibodies in the glomerulus, administration of analgesics, xanthine oxidase deficiency, toxicity of chemotherapy agents, and long-term exposure to lead or its salts.

Nephropathy associated with diabetes (i.e., "diabetic nephropathy") is the most common cause of end-stage renal disease in the United States and several other developed countries. For example, diabetic nephropathy accounts for almost 35% of end-stage renal disease in the US today and costs approximately $50,000-$65,000 per patient per year, exceeding $2 billion per year for all US patients. Approximately 40% of patients with type 1 diabetes and 5-15% of patients with type 2 diabetes eventually develop end-stage renal disease.

The pathophysiologic mechanisms of diabetic nephropathy are incompletely understood. The earliest demonstrable abnormalities include intrarenal hypertension, hyperfiltration (increased glomerular filtration rate), and microalbuminuria. Clinically, the most important screening tool for identifying early nephropathy is detection of microalbuminuria. Risk factors for development of diabetic nephropathy include hyperglycemia, hypertension, positive family history of nephropathy, and smoking. Diabetic nephropathy is generally considered to be a result of hypertension and hyperglycemia in diabetes, with many researchers considering hyperglycemia to be a significant contributing factor to the development of this disease.

Medical interventions thus far are not effective enough to treat or prevent progression of diabetic nephropathy and the development of end stage renal disease. In this regard, current treatments are primarily directed to improving complications of the diseases as follows: 1) control of blood-pressure (ACE-inhibitors inhibitors or Angiotensin receptor blockers (ARBs); 2) Control of glycemic values; and 3) lipoproteic diet, exercise or other life styles modifications. However, current treatment have limited impact on the progressive decline in kidney function and patients still progress to renal replacement therapy, either dialysis or renal transplantation.

Other treatment strategies have focused on one or more growth factors as therapeutic targets, often those identified as being upregulated in nephropathy models. For example, therapies directed at inhibiting TGFβ, either alone or in combination with ACE inhibitors have been examined. Vascular endothelial growth factor A (VEGF-A) and other factors involved in angiogenesis have also been studied as targets in the treatment of nephropathy.

VEGF and Nephropathy

The VEGF family of growth factors incorporates five ligands (VEGF-A, VEGF-B, VEGF-C, VEGF-D, and placenta growth factor (PIGF)) that can bind differentially to three receptor tyrosine kinases (VEGFR-1, -2, and -3) and the semaphorin receptors (neuropilin 1 and 2). The VEGF family of growth factors are involved in normal and pathological angiogenesis and lymphangiogenisis. VEGF-A binds to VEGFR-1, VEGFR-2, NP-1, and NP-2; VEGF-B binds to VEGFR-1 and NP-1. VEGF-C and VEGF-D are mainly involved in lymphangiogenesis and bind to VEGFR-2, VEGFR-3 and NP-2.

VEGF-A is the most well studied member of the VEGF family, and the role of VEGF-A and investigations of the inhibition of VEGF-A in relation to kidney and nephropathy have provided mixed outcomes, often resulting in deleterious effects on the kidney. Some of these studies have involved the administration of soluble VEGF receptor 1 (also known as sFlt-1), which may act as an antagonist of VEGF-A but also of VEGF-B and P1GF, and have led to proteinurea and hypertension (Nakagawa et al, Diabetes, 58, p1471-8, 2009). Kosugi et al (Am J Physiol Renal Physiol 298: F609-F616, 2010) concluded that sFlt-1 treatment is unlikely to be beneficial in diabetic nephropathy and that alternative approaches to treating diabetic renal disease are needed. A recent study involving an antagonist of VEGFR-1 (Yang et al, PLOS ONE, 9(4), e94540, 2014) in db/db mice concluded that inhibition of VEGFR-1 aggravates diabetic nephropathy, and actually suggested that VEGFR-1 activation may provide a therapeutic modality in type 2 diabetic nephropathy. As discussed above. VEGF-B is one of the ligands that signals through VEGFR-1, and these studies involving sFlt-1 or the antagonist of VEGFR-1 would have blocked VEGF-B signalling, albeit in a non-specific manner.

SUMMARY

In producing the present invention, the inventors proceeded against the knowledge in the art in relation to VEGF signaling in nephropathy and studied the effects of inhibiting signaling of VEGF-B in accepted mouse models of nephropathy. e.g., high fat fed mice and models of diabetic nephropathy including, nephropathy associated with type 1 diabetes and type 2 diabetes. The inventors studied the effect of this growth factor by preventing expression of VEGF-B (e.g., using genetically-modified mice in which expression of VEGF-B is reduced or prevented) or by administering an antagonist of VEGF-B (e.g., an antagonistic antibody). The present inventors have found that, surprisingly, the inhibition of VEGF-B signalling has a beneficial effect in a variety of animal models of nephropathy. For example, the inventors were able to prevent development of nephropathy, e.g., diabetic nephropathy and to treat (e.g., delay progression of) nephropathy, e.g., diabetic nephropathy depending on the treatment regime used.

The inventors found that antagonism of VEGF-B signaling decreases or prevents at least glomerular mesangial expansion, glomerular and tubular sclerosis, mesangial extracellular matrix deposition, abnormal thickening of glomerular basement membrane and renal lipid accumulation, e.g., in kidney glomeruli, podocyte loss, hypertension, glomerular vascular rearrangements and preserves podocyte structure in diabetic subjects. In some cases (e.g., in an experiment described herein) the changes in the kidney occurred despite a moderate effect on blood glucose levels in diabetic subjects, indicating that inhibiting VEGF-B provides a therapeutic/prophylactic benefit in nephropathy through a pathway additional to or other than glycemic control.

The findings by the inventors provide the basis for methods for treating or preventing nephropathy in a subject by inhibiting VEGF-B signaling. For example, the present disclosure provides a method for treating or preventing nephropathy in a subject, the method comprising administering to the subject a compound that inhibits VEGF-B signaling.

In one example, the nephropathy is nephritis, i.e., inflammatory kidney disease. For example, the nephropathy is IgA nephropathy or is caused by use of drugs (e.g., analgesics or chemotherapy), xanthine oxidase deficiency, polycystic kidney disease or is caused by an chronic disease, e.g., an inflammatory or autoimmune disease or diabetes.

For example, the nephropathy is glomerulonephritis and/or glomerulosclerosis. For example, the glomerulonephritis and/or glomerulosclerosis is a proliferative glomerulonephritis and/or glomerulosclerosis.

In one example, the nephropathy or nephritis is associated with or caused by another disease. For example, the nephropathy is caused by an inflammatory or autoimmune disease (e.g., systemic lupus erythematosis, Goodpasture syndrome), vasculitis (e.g., Wegener granulomatosus or microspcopic polyangitis) or diabetes.

In one example, the nephropathy or nephritis is associated with or caused by prediabetes.

In one example, the nephropathy or nephritis is associated with or caused by type 1 diabetes.

In one example, the nephropathy or nephritis is associated with or caused by type 2 diabetes.

For example, the present disclosure provides a method of treating or preventing diabetic nephropathy in a subject suffering from diabetes, the method comprising administering to the subject a compound that inhibits VEGF-B signaling.

As exemplified herein, the present inventors have shown that administration of an inhibitor of VEGF-B signaling to a subject suffering from diabetic nephropathy is effective in the treatment of this condition. Accordingly, the present disclosure additionally provides a method for treating diabetic nephropathy, the method comprising administering to a subject suffering from diabetic nephropathy an inhibitor of VEGF-B signaling.

In one example, the subject is at risk of developing nephropathy or is developing nephropathy (e.g., diabetic nephropathy). For example, the subject suffers from microalbuminuria or macroalbuminuria. In another example, the subject suffers from hypertension.

In one example, the present disclosure provides a method for preventing or delaying development of nephropathy (e.g., diabetic nephropathy), the method comprising administering to a subject suffering from microalbuminuria or macroalbuminuria (e.g., a subject suffering from diabetes and microalbuminuria or macroalbuminuria) a compound that inhibits VEGF-B signaling. In one example, the subject suffers from microalbuminuria.

In one example, the present disclosure provides a method for preventing or delaying development of nephropathy (e.g., diabetic nephropathy), the method comprising administering to a subject suffering from hypertension (e.g., a subject suffering from diabetes and hypertension) a compound that inhibits VEGF-B signaling.

In one example, the compound is administered in an amount effective to have one or more of the following effects:

Reduce or prevent hypertension;
Reduce or prevent glomerular and/or tubular sclerosis;
Reduce or prevent mesangial extracellular matrix deposition and/or abnormal thickening of the glomerular basement membrane;
Reduce or prevent glomerular mesangial expansion;
Reduce or prevent glomerular vascular rearrangements;
Reduce or prevent renal lipid accumulation;
Reduce or prevent glomerular lipid accumulation;
Reduce or prevent glomerular collagen deposits and/or arteriolar hyaliosis; and/or
Reduce or prevent macroalbuminuria.

In one example, the compound that inhibits VEGF-B signaling specifically inhibits VEGF-B signaling. This does not mean that a method of the present disclosure does not encompass inhibiting signaling of multiple VEGF proteins, only that the compound (or part thereof) that inhibits VEGF-B signaling is specific to VEGF-B, e.g., is not a general inhibitor of VEGF proteins. This term also does not exclude, e.g., a bispecific antibody or protein comprising binding domains thereof, which can specifically inhibit VEGF-B signaling with one (or more) binding domains and can specifically inhibit signaling of another protein with another binding domain.

In one example, a compound that inhibits VEGF-B signaling binds to VEGF-B. For example, the compound is a protein comprising an antibody variable region that binds to or specifically binds to VEGP-B and neutralizes VEGF-B signaling.

In one example, the compound is an antibody mimetic. For example, the compound is a protein comprising an antigen binding domain of an immunoglobulin. e.g., an IgNAR, a camelid antibody or a T cell receptor.

In one example, a compound is a domain antibody (e.g., comprising only a heavy chain variable region or only a light chain variable region that binds to VEGF-B) or a heavy chain only antibody (e.g., a camelid antibody or an IgNAR) or variable region thereof.

In one example, a compound is a protein comprising a Fv. For example, the protein is selected from the group consisting of:
(i) a single chain Fv fragment (scFv);
(ii) a dimeric scFv (di-scFv); or
(iv) a diabody:
(v) a triabody:
(vi) a tetrabody;
(vii) a Fab;
(viii) a F(ab')$_2$;
(ix) a Fv; or
(x) one of (i) to (ix) linked to a constant region of an antibody, Fc or a heavy chain constant domain ($C_H$)2 and/or $C_H$3.

In another example, a compound is an antibody. Exemplary antibodies are full-length and/or naked antibodies.

In one example, the compound is a protein that is recombinant, chimeric, CDR grafted, humanized, synhumanized, primatized, deimmunized or human.

In one example, the compound is a protein comprising an antibody variable region that competitively inhibits the binding of antibody 2H10 to VEGF-B. In one example, the protein comprises a heavy chain variable region ($V_H$) comprising a sequence set forth in SEQ ID NO: 3 and a light chain variable region ($V_L$) comprising a sequence set forth in SEQ ID NO: 4.

In one example, the compound is a protein comprising a humanized variable region of antibody 2H10. For example, the protein comprises a variable region comprising the complementarity determining regions (CDRs) of the $V_H$ and/or the $V_L$ of antibody 2H10. For example, the protein comprises:
(i) a $V_H$ comprising:
  (a) a CDR1 comprising a sequence set forth in amino acids 25-34 of SEQ ID NO: 3;
  (b) a CDR2 comprising a sequence set forth in amino acids 49-65 of SEQ ID NO: 3; and
  (c) a CDR3 comprising a sequence set forth in amino acids 98-108 of SEQ ID NO: 3; and/or
(ii) a $V_L$ comprising:
  (a) a CDR1 comprising a sequence set forth in amino acids 23-33 of SEQ ID NO: 4;
  (b) a CDR2 comprising a sequence set forth in amino acids 49-55 of SEQ ID NO: 4; and
  (c) a CDR3 comprising a sequence set forth in amino acids 88-96 of SEQ ID NO: 4.

In One Example, the Compound is a Protein Comprising a $V_H$ and a $V_L$, the $V_H$ and $V_L$ being Humanized Variable Regions of Antibody 2H10. For Example, the Protein Comprises:
(i) a $V_H$ comprising:
  (a) a CDR1 comprising a sequence set forth in amino acids 25-34 of SEQ ID NO: 3;
  (b) a CDR2 comprising a sequence set forth in amino acids 49-65 of SEQ ID NO: 3; and
  (c) a CDR3 comprising a sequence set forth in amino acids 98-108 of SEQ ID NO: 3; and
(ii) a $V_L$ comprising:
  (a) a CDR1 comprising a sequence set forth in amino acids 23-33 of SEQ ID NO: 4;
  (b) a CDR2 comprising a sequence set forth in amino acids 49-55 of SEQ ID NO: 4; and
  (c) a CDR3 comprising a sequence set forth in amino acids 88-96 of SEQ ID NO: 4.

In one example, the variable region or $V_H$ in any of the foregoing paragraphs comprises a sequence set forth in SEQ ID NO: 5.

In one example, the variable region or $V_L$ in any of the foregoing paragraphs comprises a sequence set forth in SEQ ID NO: 6.

In one example, the compound is an antibody.

In one example, the compound is an antibody comprising a $V_H$ comprising a sequence set forth in SEQ ID NO: 5 and a $V_L$ comprising a sequence set forth in SEQ ID NO: 6.

In one example, the protein or antibody is any form of the protein or antibody encoded by a nucleic acid encoding any of the foregoing proteins or antibodies.

In one example, the protein or antibody comprises:
(i) a $V_H$ comprising:
  (a) a CDR1 comprising a sequence encoded by a nucleic acid comprising SEQ ID NO: 11 or comprising an amino acid sequence of SEQ ID NO: 17;
  (b) a CDR2 comprising a sequence encoded by a nucleic acid comprising SEQ ID NO: 12 or comprising an amino acid sequence of SEQ ID NO: 18; and
  (c) a CDR3 comprising a sequence encoded by a nucleic acid comprising SEQ ID NO: 13 or comprising an amino acid sequence of SEQ ID NO: 19; and/or
(ii) a $V_L$ comprising:
  (a) a CDR1 comprising a sequence encoded by a nucleic acid comprising SEQ ID NO: 14 or comprising an amino acid sequence of SEQ ID NO: 20;
  (b) a CDR2 comprising a sequence encoded by a nucleic acid comprising SEQ ID NO: 15 or comprising an amino acid sequence of SEQ ID NO: 21; and
  (c) a CDR3 comprising a sequence encoded by a nucleic acid comprising SEQ ID NO: 16 or comprising an amino acid sequence of SEQ ID NO: 22.

[1] In one example, the protein or antibody comprises:
(i) a $V_H$ comprising:
  (a) a CDR1 comprising a sequence encoded by a nucleic acid comprising SEQ ID NO: 23 or comprising an amino acid sequence of SEQ ID NO: 29;
  (b) a CDR2 comprising a sequence encoded by a nucleic acid comprising SEQ ID NO: 24 or comprising an amino acid sequence of SEQ ID NO: 30; and
  (c) a CDR3 comprising a sequence encoded by a nucleic acid comprising SEQ ID NO: 25 or comprising an amino acid sequence of SEQ ID NO: 31; and/or
(ii) a $V_L$ comprising:
  (a) a CDR1 comprising a sequence encoded by a nucleic acid comprising SEQ ID NO: 26 or comprising an amino acid sequence of SEQ ID NO: 32;
  (b) a CDR2 comprising a sequence encoded by a nucleic acid comprising SEQ ID NO: 27 or comprising an amino acid sequence of SEQ ID NO: 33; and
  (c) a CDR3 comprising a sequence encoded by a nucleic acid comprising SEQ ID NO: 28 or comprising an amino acid sequence of SEQ ID NO: 34.

In one example, the protein or antibody comprises:
(i) a $V_H$ comprising
  (a) a CDR1 comprising a sequence encoded by a nucleic acid comprising SEQ ID NO: 35 or comprising an amino acid sequence of SEQ ID NO: 41;
  (b) a CDR2 comprising a sequence encoded by a nucleic acid comprising SEQ ID NO: 36 or comprising an amino acid sequence of SEQ ID NO: 42; and
  (c) a CDR3 comprising a sequence encoded by a nucleic acid comprising SEQ ID NO: 37 or comprising an amino acid sequence of SEQ ID NO: 43; and/or
(ii) a $V_L$ comprising:
  (a) a CDR1 comprising a sequence encoded by a nucleic acid comprising SEQ ID NO: 38 or comprising an amino acid sequence of SEQ ID NO: 44;
  (b) a CDR2 comprising a sequence encoded by a nucleic acid comprising SEQ ID NO: 39 or comprising an amino acid sequence of SEQ ID NO: 45; and
  (c) a CDR3 comprising a sequence encoded by a nucleic acid comprising SEQ ID NO: 40 or comprising an amino acid sequence of SEQ ID NO: 46.

In one example, the compound is within a composition. For example, the composition comprises a protein comprising an antibody variable region or a $V_H$ or a $V_L$ or an antibody as described herein. In one example, the composition additionally comprises one or more variants of the protein or antibody. For example, that comprises a variant missing an encoded C-terminal lysine residue, a deamidated variant and/or a glycosylated variant and/or a variant comprising a pyroglutamate, e.g., at the N-terminus of a protein and/or a variant lacking a N-terminal residue, e.g., a N-terminal glutamine in an antibody or V region and/or a variant comprising all or part of a secretion signal. Deamidated variants of encoded asparigine residues may result in isoaspartic, and aspartic acid isoforms being generated or even a succinamide involving an adjacent amino acid residue. Deamidated variants of encoded glutamine residues may result in glutamic acid. Compositions comprising a heterogeneous mixture of such sequences and variants are intended to be included when reference is made to a particular amino acid sequence.

In one example, the compound that inhibits VEGF-B signaling inhibits or prevents expression of VEGF-B. For example, the compound is selected from the group an antisense, a siRNA, a RNAi, a ribozyme and a DNAzyme.

In one example, the VEGF-B is mammalian VEGF-B, e.g., human VEGF-B.

In one example, the subject is a mammal, for example a primate, such as a human.

Methods of treatment described herein can additionally comprise administering a further compound to treat or prevent the nephropathy.

Methods of treatment of diabetic nephropathy described herein can additionally comprise administering a further compound to treat or prevent (or delay progression of) diabetes. Exemplary compounds are described herein.

The present disclosure also provides a compound that inhibits VEGF-B signaling for use in the treatment or prevention of nephropathy.

The present disclosure also provides for use of a compound that inhibits VEGF-B signaling in the manufacture of a medicament for treating or preventing nephropathy.

The present disclosure also provides a kit comprising a compound that inhibits VEGF-B signaling packaged with instructions for use in the treatment or prevention of nephropathy.

Exemplary nephropathies and compounds are described herein and are to be taken to apply mutatis mutandis to the examples of the disclosure set out in the previous three paragraphs.

BRIEF DESCRIPTION OF THE DRAWINGS

FIG. 15A shows postprandial blood glucose levels in untreated animals. Arrows indicate glucose levels at the start of the prophylactic or therapeutic trial. FIG. 15B shows ACR in untreated db/db//BKS animals Arrows indicate ACR at the start of the prophylactic or therapeutic trial FIGS. 15C and 15D show postprandial blood glucose levels from preventative anti-VEGF-B treatment in db/db//BKS separately shown for male (6C n=5/group) and female (6D, n=5-6/group) mice. FIGS. 15E and 15F show postprandial blood glucose levels from therapeutic anti-VEGF-B treatment in db/db//BKS separately shown for male (15E, n=5/group) and female (15F, n=5-6/group) mice. The administration period of anti-VEGF-B (2H10) treatment is indicated in the respective graphs.

FIG. 23A is a graphical representation showing quantification of glomerular sclerosis as measured by mesangial expansion in kidney sections from female db/db//BKS mice treated with anti-VEGF-B (2H10) or control antibody for 8 weeks (as indicated) in a therapeutic manner. Values are means±s.e.m. *P<0.05, P<0.01, *p<0.001 compared to controls.

FIG. 23B is a graphical representation showing quantification of glomerular sclerosis as measured by mesangial expansion in kidney sections from male db/db//BKS mice treated with anti-VEGF-B (2H10) or control antibody for 8 weeks (as indicated) in a therapeutic manner. Values are means±s.e.m.

FIG. 24 is a graphical representation showing quantification of oil red O staining in kidney sections from db/db//BKS mice treated with anti-VEGF-B (2H10) or control antibody for 8 weeks (as indicated) in a therapeutic manner. Values are means±s.e.m. *P<0.05, P<0.01, *p<0.001 compared to controls.

FIG. 26A is a graphical representation showing quantification of glomerular collagen IV staining in kidney sections from db/db//BKS mice treated with anti-VEGF-B (2H10) or control antibody in a therapeutic manner. Values are means±s.e.m. *P<0.05 compared to controls.

FIG. 26B is a graphical representation showing quantification of glomerular α-SMA staining in kidney sections from db/db//BKS mice treated with anti-VEGF-B (2H10) or control antibody in a therapeutic manner. Values are means±s.e.m. *P<0.05, **P<0.01 compared to controls. (n=4–5/group).

FIG. 26C is a graphical representation showing quantification of glomerular arteriolar thickness in kidney sections from db/db//BKS mice treated with anti-VEGF-B (2H10) or control antibody in a therapeutic manner. Values are means±s.e.m. *P<0.05, **P<0.01 compared to controls. (n=4–5/group).

KEY TO SEQUENCE LISTING

Figure 1A:
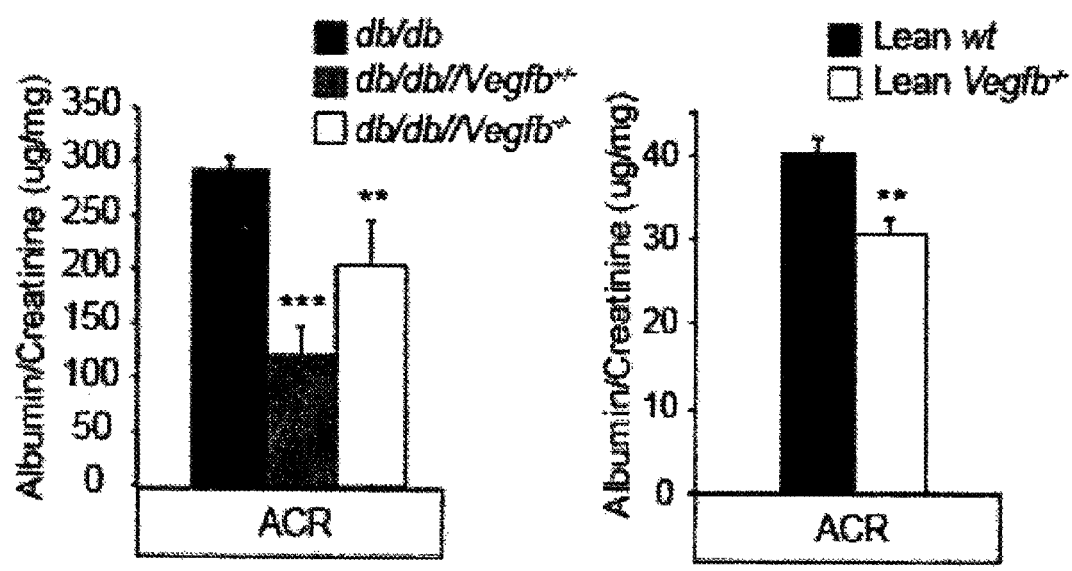
FIG. 1A comprises two graphical representations showing urine albumin/creatinine ratio (ACR) measured by ELISA for db/db, db/db//Vegfb$^{+/-}$ and db/db//Vegfb$^{-/-}$ mice (n=5 group, left graph) and lean wild type (wt) and lean Vegfb$^{-/-}$ mice (n=4-6/group, right graph). Values are means± s.e.m. *P<0.05, P<0.01, *P<0.001 compared to db/db controls.

SEQ ID NO: 1 is an amino acid sequence of a human VEGF-B$_{186}$ isoform containing a 21 amino acid N-terminal signal sequence SEQ ID NO: 2 is an amino acid sequence of a human VEGF-B$_{167}$ isoform containing a 21 amino acid N-terminal signal sequence SEQ ID NO: 3 is an amino acid sequence from a $V_H$ of antibody 2H10.

SEQ ID NO: 4 is an amino acid sequence from a $V_L$ of antibody 2H10.

SEQ ID NO: 5 is an amino acid sequence from a $V_H$ of a humanized form of antibody 2H10.

SEQ ID NO: 6 is an amino acid sequence of a $V_L$ of a humanized form of antibody 2H10.

SEQ ID NO: 7 is an amino acid sequence from a $V_H$ of antibody 4E12.

SEQ ID NO: 8 is an amino acid sequence of a $V_L$ of antibody 4E12.

SEQ ID NO: 9 is an amino acid sequence from a $V_H$ of antibody 2F5.

SEQ ID NO: 10 is an amino acid sequence of a $V_L$ of antibody 2F5.

SEQ ID NO: 11 is a nucleotide sequence from a $V_L$ CDR1 of antibody 2H10

SEQ ID NO: 12 is a nucleotide sequence from a $V_L$ CDR2 of antibody 2H10

SEQ ID NO: 13 is a nucleotide sequence from a $V_L$ CDR3 of antibody 2H10

SEQ ID NO: 14 is a nucleotide sequence from a $V_H$ CDR1 of antibody 2H10

SEQ ID NO: 15 is a nucleotide sequence from a $V_H$ CDR2 of antibody 2H10

SEQ ID NO: 16 is a nucleotide sequence from a $V_H$ CDR3 of antibody 2H10

SEQ ID NO: 17 is an amino acid sequence from a $V_L$ CDR1 of antibody 2H10

SEQ ID NO: 18 is an amino acid sequence from a $V_L$ CDR2 of antibody 2H10

SEQ ID NO: 19 is an amino acid sequence from a $V_L$ CDR3 of antibody 2H10

SEQ ID NO: 20 is an amino acid sequence from a $V_H$ CDR1 of antibody 2H10

SEQ ID NO: 21 is an amino acid sequence from a $V_H$ CDR2 of antibody 2H10

SEQ ID NO: 22 is an amino acid sequence from a $V_H$ CDR3 of antibody 2H10

SEQ ID NO: 23 is a nucleotide sequence from a $V_L$ CDR1 of antibody 2F5

SEQ ID NO: 24 is a nucleotide sequence from a $V_L$ CDR2 of antibody 2F5

SEQ ID NO: 25 is a nucleotide sequence from a $V_L$ CDR3 of antibody 2F5

SEQ ID NO: 26 is a nucleotide sequence from a $V_H$ CDR of antibody 2F5

SEQ ID NO: 27 is a nucleotide sequence from a $V_H$ CDR2 of antibody 2F5

SEQ ID NO: 28 is a nucleotide sequence from a $V_H$ CDR3 of antibody 2F5

SEQ ID NO: 29 is an amino acid sequence from a $V_L$ CDR1 of antibody 2F5

SEQ ID NO: 30 is an amino acid sequence from a $V_L$ CDR2 of antibody 2F5

SEQ ID NO: 31 is an amino acid sequence from a $V_L$ CDR3 of antibody 2F5

SEQ ID NO: 32 is an amino acid sequence from a $V_H$ CDR1 of antibody 2F5

SEQ ID NO: 33 is an amino acid sequence from a $V_H$ CDR2 of antibody 2F5

SEQ ID NO: 34 is an amino acid sequence from a $V_H$ CDR3 of antibody 2F5

SEQ ID NO: 35 is a nucleotide sequence from a $V_L$ CDR1 of antibody 4E12

SEQ ID NO: 36 is a nucleotide sequence from a $V_L$ CDR2 of antibody 4E12

SEQ ID NO: 37 is a nucleotide sequence from a $V_L$ CDR3 of antibody 4E12

SEQ ID NO: 38 is a nucleotide sequence from a $V_H$ CDR1 of antibody 4E12

SEQ ID NO: 39 is a nucleotide sequence from a $V_H$ CDR2 of antibody 4E12

SEQ ID NO: 40 is a nucleotide sequence from a $V_H$ CDR3 of antibody 4E12

SEQ ID NO: 41 is an amino acid sequence from a $V_L$ CDR11 of antibody 4E12

SEQ ID NO: 42 is an amino acid sequence from a $V_L$ CDR2 of antibody 4E12

SEQ ID NO: 43 is an amino acid sequence from a $V_L$ CDR3 of antibody 4E12

SEQ ID NO: 44 is an amino acid sequence from a $V_H$ CDR1 of antibody 4E12

SEQ ID NO: 45 is an amino acid sequence from a $V_H$ CDR2 of antibody 4E12

SEQ ID NO: 46 is an amino acid sequence from a $V_H$ CDR3 of antibody 4E12

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Any example of the present disclosure in relation to treatment or prevention of an nephropathy shall be taken to apply mutatis mutandis to inhibiting or preventing an innate immune response (e.g., an innate immune response in the digestive system and/or a systemic innate immune response) in a subject suffering from an nephropathy.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual. Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach. Volumes 1-4, IRL Press (1995 and 1996), and F. M. Ausubel et al. (editors), Current Protocols in Molecular Biology, Greene Pub. Associates and Wiley-Interscience (1988, including all updates until present). Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health. Bethesda, Md., 1987 and 1991, Bork et al., *J Mol. Biol.* 242, 309-320, 1994. Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

Any discussion of a protein or antibody herein will be understood to include any variants of the protein or antibody produced during manufacturing and/or storage. For example, during manufacturing or storage an antibody can be deamidated (e.g., at an asparagine or a glutamine residue) and/or have altered glycosylation and/or have a glutamine residue converted to pyroglutamine and/or have a N-terminal or C-terminal residue removed or "clipped" and/or have part or all of a signal sequence incompletely processed and, as a consequence, remain at the terminus of the antibody. It is understood that a composition comprising a particular amino acid sequence may be a heterogeneous mixture of the stated or encoded sequence and/or variants of that stated or encoded sequence.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

VEGF-B is known to exist in two major isoforms, referred to as VEGF-$B_{186}$ and VEGF-$B_{167}$. For the purposes of nomenclature only and not limitation exemplary sequences of human VEGF-$B_{186}$ is set out in NCBI Reference Sequence: NP_003368.1, in NCBI protein accession numbers NP_003368. P49765 and AAL79001 and in SEQ ID NO: 1. In the context of the present disclosure, the sequence of VEGF-$B_{186}$ can lack the 21 amino acid N-terminal signal sequence (e.g., as set out at amino acids 1 to 21 of SEQ ID NO: 1. For the purposes of nomenclature only and not limitation exemplary sequences of human VEGF-$B_{167}$ is set out in NCBI Reference Sequence: NP_001230662.1, in NCBI protein accession numbers AAL79000 and AAB06274 and in SEQ ID NO: 2. In the context of the present disclosure, the sequence of VEGF-B$_{167}$ can lack the 21 amino acid N-terminal signal sequence (e.g., as set out at amino acids 1 to 21 of SEQ ID NO: 2. Additional sequence of VEGF-B can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)). Reference to human VEGF-B may be abbreviated to hVEGF-B. In one example, reference herein to VEGF-B is to VEGF-B$_{167}$ isoform.

Reference herein to VEGF-B also encompasses the VEGF-B$_{10-108}$ peptide as described in WO2006/012688.

The term "nephropathy" shall be understood to mean damage to or disease of a kidney. This term encompasses all clinical-pathological changes in the kidney which may result in kidney fibrosis and/or glomerular diseases (e.g. glomerulosclerosis, glomerulonephritis) and/or chronic renal insufficiency, and can cause end stage renal disease and/or renal failure. Exemplary nephropathies include hypertensive nephropathy, diabetic nephropathy, and other types of nephropathy such as analgesic nephropathy, immune-mediated glomerulopathies (e.g. IgA nephropathy or Berger's disease, lupus nephritis), ischemic nephropathy. HIV-associated nephropathy, membranous nephropathy, glomerulonephritis, glomecrulosclerosis, radiocontrast media-induced nephropathy, toxic nephropathy, analgesic-induced nephrotoxicity, cisplatin nephropathy, transplant nephropathy, and other forms of glomerular abnormality or injury; glomerular capillary injury (tubular fibrosis). In some examples, the terms "nephropathy" or "nephropathies" refers specifically to a disorder or disease where there is either the presence of proteins (i.e. proteinuria), such as albumin, in the urine of a subject and/or the presence of renal insufficiency. Nephropathy is often diagnosed based on the presence of albumin in the urine (microalbuminuria or macroalbuminuria), increased blood urea nitrogen levels (e.g., levels above 20 mg/dL) and/or increased serum creatinine levels (e.g., levels above 1.3 mg/dL for males and 1.1 mg/dL for females).

The term "fibrosis" refers to abnormal processing of fibrous tissue, or fibroid or fibrous degeneration. Fibrosis can result from various injuries or diseases. Fibrosis typically involves the abnormal production, accumulation, or deposition of extracellular matrix components, including overproduction and increased deposition of, for example, collagen and fibronectin. As used herein, the terms "kidney fibrosis" or "renal fibrosis" or "fibrosis of the kidney" refer to diseases or disorders associated with the overproduction or abnormal deposition of extracellular matrix components, particularly collagen, leading to the degradation or impairment of kidney function.

The term "nephritis" will be understood to mean inflammation of a kidney. In the context of the present disclosure, nephritis encompasses a subset of nephropathy characterized by inflammation in a kidney. The inflammation can involve glomeruli, tubules, or interstitial tissue surrounding the glomeruli and tubules. Generally, nephritis is either glomerulonephritis (i.e., inflammation of the glomeruli) or interstitial nephritis (i.e., inflammation of the interstitial spaces between renal tubules).

The term "glomerulonephritis" encompasses a class of kidney diseases, which can be broken into sub-class of proliferative diseases and non-proliferative diseases. As the names suggest, "proliferative" diseases include forms of glomerulonephritis in which there is a significant increase in the number of cells in the glomerulus, while "non-proliferative" diseases include forms of glomerulonephritis in which such an increase in cell numbers is not present. Exemplary proliferative diseases include IgA nephropathy, post-infectious glomerulonephritis, membranoproliferative glomerulonephritis and rapidly progressive glomerulonephritis. Exemplary non-proliferative diseases include minimal change disease, focal segment glomerulosclerosis think basement membrane disease and membranous glomerulonephritis.

"Diabetic nephropathy" is a clinically well-defined pathology characterized by proteinuria, hypertension, edema and renal insufficiency. Characteristic aspects of diabetic nephropathy include glomerulosclerosis, modification of the vascular structure, and tubulointerstitial disease. The first clinical evidence of diabetic nephropathy is often the presence of albuminuria in the urine. e.g. microalbuminuria or macroalbuminuria. Diabetic nephropathy is typically characterized by the following: 1) glomerulosclerosis, 2) modification of the vascular structure, mainly in the small arterioles and 3) tubulointerstitial disease. The most characteristic aspect of diabetic nephropathy is the glomerular injury, detectable by the enlargement of the mesangium and by the thickening of the basal membrane, which often looks like a diffuse cicatrisation of the whole glomerule. The first clinical evidence of diabetic nephropathy is the presence of albuminuria or proteinuria.

By "microalbuminuria" is meant the presence of 30-300 mg albumin per 24 hours of urine collection and/or 30-300 mg/L albumin in a single sample. Generally, both of the foregoing should be measured in at least two of three samples over a two to three month period. Microalbuminuria can also be defined by a ratio of albumin to creatinine (ACR) of ≥3.5 mg/mmol for females or ≥2.5 mg/mmol for males or between 30-300 µg albumin/mg creatinine. Albumin levels can be assessed using, for example, commercially available dipsticks (e.g., comprising bromophenol blue as an indicator).

The term "macroalbuminuria" means the presence of amounts of albumin higher (or higher ACR) than is observed in microalbuminuria.

The term "proteinuria" means the amount of total protein in urine is about ≥30 mg/dL or a protein/creatinine ratio greater than 45 mg/mmol.

"Hypertension" refers to a subject (e.g., a human subject) having a systolic pressure of 140 mm Hg or higher and/or a diastolic pressure of 90 mm Hg or higher. In some examples of a method or use described herein, a subject is prehypertensive, e.g., having a systolic pressure of about 120-139 mm Hg or higher and/or a diastolic pressure of 80-89 mm Hg or higher.

The term "recombinant" shall be understood to mean the product of artificial genetic recombination. Accordingly, in the context of a recombinant protein comprising an antibody variable region, this term does not encompass an antibody naturally-occurring within a subject's body that is the product of natural recombination that occurs during B cell maturation. However, if such an antibody is isolated, it is to be considered an isolated protein comprising an antibody variable region. Similarly, if nucleic acid encoding the protein is isolated and expressed using recombinant means, the resulting protein is a recombinant protein comprising an antibody variable region. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The skilled artisan will be aware that an "antibody" is generally considered to be a protein that comprises a variable region made up of a plurality of polypeptide chains. e.g., a polypeptide comprising a light chain variable region ($V_L$) and a polypeptide comprising a heavy chain variable region ($V_H$). An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG. IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies, synhumanized antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. *Nature* 342, 877-883, 1989; and/or Al-Lazikani et al., *J Mol Biol* 273: 927-948, 1997; the IMGT numbering system of Lefranc et al., *Devel. And Compar. Immunol.*, 27: 55-77, 2003; or the AHO numbering system of Honnegher and Pltlkthun *J. Mol. Biol.*, 309: 657-670, 2001.

"Framework regions" (FRs) are those variable domain residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain. e.g., a minibody. A "Fab fragment" consists of a monovalent antigen-binding fragment of an antibody, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "$Fab_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a protein or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a protein of the disclosure reacts or associates more frequently, more rapidly, with greater duration and/or with greater affinity with a particular antigen or cell expressing same than it does with alternative antigens or cells. For example, a protein binds to VEGF-B with materially greater affinity (e.g., 20 fold or 40 fold or 60 fold or 80 fold to 100 fold or 150 fold or 200 fold) than it does to other growth factor (e.g., VEGF-A) or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

As used herein, the term "neutralize" shall be taken to mean that a protein is capable of blocking, reducing or preventing VEGF-B-signaling in a cell through the VEGF-R1. Methods for determining neutralization are known in the art and/or described herein.

As used herein, the term "specifically inhibits VEGF-B signaling" will be understood to mean that the compound inhibits VEGF-B signaling and does not significantly or detectably inhibit signaling by one or more other VEGF proteins, e.g., VEGF-A. VEGF-B, VEGF-C, VEGF-D and/or PIGF.

As used herein, the term "does not significantly inhibit" shall be understood to mean that the level of inhibition of signaling by a VEGF protein other than VEGF-B (e.g., signalling by VEGF-A, VEGF-B, VEGF-C, VEGF-D and/or PIGF) in the presence of a compound described herein is not statistically significantly lower than in the absence of the compound described herein (e.g., in a control assay which may be conducted in the presence of an isotype control antibody).

As used herein, the term "does not detectably inhibit" shall be understood to mean that a compound as described herein inhibits signalling of a VEGF protein other than VEGF-B (e.g., signalling by VEGF-A, VEGF-B, VEGF-C, VEGF-D and/or PIGF) by no more than 10% or 8% or 6% or 5% or 4% or 3% or 2% or 1% of the level of signalling detected in the absence of the compound described herein (e.g., in a control assay which may be conducted in the presence of an isotype control antibody).

As used herein, the terms "preventing", "prevent" or "prevention" include administering a compound of the disclosure to thereby stop or hinder the development of at least one symptom of a condition.

As used herein, the terms "treating", "treat" or "treatment" include administering a protein described herein to thereby reduce or eliminate at least one symptom of a specified disease or condition or to slow progression of the disease or condition.

As used herein, the term "subject" shall be taken to mean any animal including humans, for example a mammal. Exemplary subjects include but are not limited to humans and non-human primates. For example, the subject is a human.

Treatment of Nephropathy

The disclosure herein provides, for example, a method for treating or preventing nephropathy in a subject comprising administering to the subject a compound that inhibits VEGF-B signaling.

In one example, the subject suffers from diabetes. For example, a subject suffering from diabetes has a clinically accepted marker of diabetes, such as:

Fasting plasma glucose of greater than or equal to 7 nmol/L or 126 mg/dl;
Casual plasma glucose (taken at any time of the day) of greater than or equal to 11.1 nmol/L or 200 mg/dl with the symptoms of diabetes.
Oral glucose tolerance test (OTT) value of greater than or equal to 11.1 nmol/L or 200 mg/dl measured at a two-hour interval. The OGTT is given over a two or three-hour time span.

In one example, the subject suffers from type 1 diabetes.
In one example, the subject suffers from type 2 diabetes.

In one example, the subject suffers from diabetic nephropathy. For example, the subject suffers from nephropathy associated with type 1 diabetes. For example, the subject suffers from nephropathy associated with type 2 diabetes.

In one example, the subject is at risk of developing diabetic nephropathy. For example, the subject is at risk of developing nephropathy associated with type 1 diabetes. For example, the subject is at risk of developing nephropathy associated with type 2 diabetes.

In one example, the subject suffers from microalbuminuria. In accordance with this example, treatment according to the present disclosure may reduce the microalbuminuria (e.g., to less than about 30 mg albumin per 24 hours of urine collection and/or 30 mg/L albumin in a single sample and/or an ACR of less than 3.5 mg/mmol for females or less than 2.5 mg/mmol for males or less than about 30 µg albumin/mg creatinine.

In another example, treatment according to the present disclosure prevents or slows progression of microalbuminuria to macroalbuminuria.

In one example, the subject suffers from reduced glomerular filtration rate, e.g., as measured by reduced creatinine clearance rate (e.g., below 90 mL/min/1.73 m$^2$). In one example, a method of the disclosure enhances glomerular filtration rate.

In a further example, the subject suffers from hypertension or prehypertension. In one example, a method of the disclosure are effective in lowering a subject's systolic and/or diastolic blood pressure by at least 1, 2, 3, 4, 5, 6, 7, 8, 9, 10 mm Hg or more.

In one example, performing a method described herein according to any example of the disclosure results enhancement of a clinical response and/or delayed disease progression.

By "clinical response" is meant an improvement in the symptoms of disease. The clinical response may be achieved within a certain time frame, for example, within or at about 8 weeks from the start of treatment with, or from the initial administration. Clinical response may also be sustained for a period of time, such as for >24 weeks, or ≥48 weeks.

Quantitative assessment of renal function and parameters of renal dysfunction are well known in the art and can be found, for example, in Levey (*Am J Kidney Dis.* 22(1):207-214, 1993). Examples of assays for the determination of renal function/dysfunction are: serum creatinine level; creatinine clearance rate; cystatin C clearance rate, 24-hour urinary creatinine clearance, 24-hour urinary protein secretion; Glomerular filtration rate (GFR); urinary albumin creatinine ratio (ACR); albumin excretion rate (AER); and renal biopsy.

VEGF-B Signaling Inhibitors
Proteins Comprising Antibody Variable Regions

An exemplary VEGF-B signaling inhibitor comprises an antibody variable region, e.g., is an antibody or an antibody fragment that binds to VEGF-B and neutralizes VEGF-B signaling.

In one example, the antibody variable region binds specifically to VEGF-B.

Suitable antibodies and proteins comprising variable regions thereof are known in the art.

For example, anti-VEGF-B antibodies and fragments thereof are described in WO2006/012688.

In one example, the anti-VEGF-B antibody or fragment thereof is an antibody that competitively inhibits the binding of 2H10 to VEGF-B or an antigen binding fragment thereof. In one example, the anti-VEGF-B antibody or fragment thereof is antibody 2H10 or a chimeric, CDR grafted or humanized version thereof or an antigen binding fragment thereof. In this regard, antibody 2H10 comprises a $V_H$ comprising a sequence set forth in SEQ ID NO: 3 and a $V_L$ comprising a sequence set forth in SEQ ID NO: 4. Exemplary chimeric and humanized versions of this antibody are described in WO2006/012688.

In one example, the anti-VEGF-B antibody or fragment thereof comprises a $V_H$ comprising a sequence set forth in SEQ ID NO: 5 and a $V_L$ comprising a sequence set forth in SEQ ID NO: 6.

In one example, the anti-VEGF-B antibody or fragment thereof is an antibody that competitively inhibits the binding of 4E12 to VEGF-B or an antigen binding fragment thereof. In one example, the anti-VEGF-B antibody or fragment thereof is antibody 4E12 or a chimeric, CDR grafted or humanized version thereof or an antigen binding fragment thereof. In this regard, antibody 4E12 comprises a $V_H$ comprising a sequence set forth in SEQ ID NO: 7 and a $V_L$ comprising a sequence set forth in SEQ ID NO: 8.

In one example, the compound is a protein comprising a humanized variable region of antibody 4E12. For example, the protein comprises a variable region comprising the complementarity determining regions (CDRs) of the $V_H$ and/or the $V_L$ of antibody 4E12. For example, the protein comprises:
(i) a $V_H$ comprising:
  (a) a CDR1 comprising a sequence set forth in amino acids 25-34 of SEQ ID NO: 7;
  (b) a CDR2 comprising a sequence set forth in amino acids 49-65 of SEQ ID NO: 7; and
  (c) a CDR3 comprising a sequence set forth in amino acids 98-105 of SEQ ID NO: 7; and/or
(ii) a $V_L$, comprising:
  (a) a CDR1 comprising a sequence set forth in amino acids 24-34 of SEQ ID NO: 8;
  (b) a CDR2 comprising a sequence set forth in amino acids 50-56 of SEQ ID NO: 8; and
  (c) a CDR3 comprising a sequence set forth in amino acids 89-97 of SEQ ID NO: 8.

In one example, the anti-VEGF-B antibody or fragment thereof is an antibody that competitively inhibits the binding of 2F5 to VEGF-B or an antigen binding fragment thereof. In one example, the anti-VEGF-B antibody or fragment thereof is antibody 2F5 or a chimeric. CDR grafted or humanized version thereof or an antigen binding fragment thereof. In this regard, antibody 2E5 comprises a $V_H$ comprising a sequence set forth in SEQ ID NO: 9 and a $V_L$ comprising a sequence set forth in SEQ ID NO: 10.

In one example, the compound is a protein comprising a humanized variable region of antibody 2F5. For example, the protein comprises a variable region comprising the complementarity determining regions (CDRs) of the $V_H$ and/or the $V_L$ of antibody 2F5. For example, the protein comprises:
(i) a $V_H$ comprising:
  (a) a CDR1 comprising a sequence set forth in amino acids 25-34 of SEQ ID NO: 9;
  (b) a CDR2 comprising a sequence set forth in amino acids 49-65 of SEQ ID NO: 9; and
  (c) a CDR3 comprising a sequence set forth in amino acids 98-107 of SEQ ID NO: 9; and/or
(ii) a $V_L$ comprising:
  (a) a CDR1 comprising a sequence set forth in amino acids 24-34 of SEQ ID NO: 10;
  (b) a CDR2 comprising a sequence set forth in amino acids 50-56 of SEQ ID NO: 10; and
  (c) a CDR3 comprising a sequence set forth in amino acids 89-96 of SEQ ID NO: 10.

In another example, an antibody or protein comprising a variable region thereof is produced using a standard method, e.g., as is known in the art or briefly described herein.

Immunization-based Methods

To generate antibodies, VEGF-B or an epitope bearing fragment or portion thereof or a modified form thereof or nucleic acid encoding same (an "immunogen"), optionally formulated with any suitable or desired adjuvant and/or pharmaceutically acceptable carrier, is administered to a subject (for example, a non-human animal subject, such as, a mouse, a rat, a chicken etc.) in the form of an injectable composition. Exemplary non-human animals are mammals, such as murine animals (e.g., rats or mice). Injection may be intranasal, intramuscular, sub-cutaneous, intravenous, intradermal, intraperitoneal, or by other known route. Optionally, the immunogen is administered numerous times. Means for preparing and characterizing antibodies are known in the art (See, e.g., Antibodies: A Laboratory Manual. Cold Spring Harbor Laboratory, 1988). Methods for producing anti-VEGF-B antibodies in mice are described in WO2006/012688.

The production of polyclonal antibodies may be monitored by sampling blood of the immunized animal at various points following immunization. A second, booster injection, may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are exemplary antibodies contemplated by the present disclosure. Generally, production of monoclonal antibodies involves, immunizing a subject (e.g., a rodent, e.g., mouse or rat) with the immunogen under conditions sufficient to stimulate antibody producing cells. In some examples, a mouse genetically-engineered to express human antibodies and not express murine antibodies proteins, is immunized to produce an antibody (e.g., as described in PCT/US2007/008231 and/or Lonberg et al., Nature 368 (1994): 856-859). Following immunization, antibody producing somatic cells (e.g., B lymphocytes) are fused with immortal cells, e.g., immortal myeloma cells. Various methods for producing such fused cells (hybridomas) are known in the art and described, for example, in Kohler and Milstein, Nature 256, 495-497, 1975. The hybridoma cells can then be cultured under conditions sufficient for antibody production.

The present disclosure contemplates other methods for producing antibodies, e.g., ABL-MYC technology (as described, for example in Largaespada et al, Curr. Top. Microbiol. Immunol, 166, 91-96, 1990).

Library-Based Methods

The present disclosure also encompasses screening of libraries of antibodies or proteins comprising antigen binding domains thereof (e.g., comprising variable regions thereof) to identify a VEGF-B binding antibody or protein comprising a variable region thereof.

Examples of libraries contemplated by this disclosure include naïve libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001)

and used to encode and display proteins using a method known in the art. Other techniques for producing libraries of proteins are described in, for example in U.S. Pat. No. 6,300,064 (e.g., a HuCAL library of Morphosys AG); U.S. Pat. Nos. 5,885,793; 6,204,023; 6,291,158; or 6,248,516.

The proteins according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding domains of antibodies are expressed on phage, e.g., as described in U.S. Pat. Nos. 6,300,064; 5,885,793; 6,204,023; 6,291,158; or 6,248,516. Other phage display methods are known in the art and are contemplated by the present disclosure. Similarly, methods of cell display are contemplated by the disclosure, e.g., bacterial display libraries, e.g., as described in U.S. Pat. No. 5,516,637; yeast display libraries, e.g., as described in U.S. Pat. No. 6,423,538 or a mammalian display library.

Methods for screening display libraries are known in the art. In one example, a display library of the present disclosure is screened using affinity purification, e.g., as described in Scopes (In: Protein purification: principles and practice. Third Edition, Springer Verlag, 1994). Methods of affinity purification typically involve contacting proteins comprising antigen binding domains displayed by the library with a target antigen (e.g., VEGF-B) and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., *J Immunol Methods*. 354:85-90, 2010: or Jostock et al., *J Immunol Methods*, 289, 65-80, 2004. Alternatively, or additionally, standard cloning methods are used, e.g., as described in Ausubel et al (In: Current Protocols in Molecular Biology. Wiley Interscience, ISBN 047 150338, 1987), and/or (Sambrook et al (In: Molecular Cloning: Molecular Cloning: A Laboratory Manual, Cold Spring Harbor Laboratories, New York, Third Edition 2001). Deimmunized, Chimeric, Humanized, Synhumanized Primatized and Human Proteins The proteins of the present disclosure may be a humanized protein.

The term "humanized protein" shall be understood to refer to a protein comprising a human-like variable region, which includes CDRs from an antibody from a non-human species (e.g., mouse or rat or non-human primate) grafted onto or inserted into FRs from a human antibody (this type of antibody is also referred to a "CDR-grafted antibody"). Humanized proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, e.g., U.S. Pat. Nos. 5,225,539, 6,054,297, 7,566,771 or 5,585,089. The term "humanized protein" also encompasses a super-humanized protein, e.g., as described in U.S. Pat. No. 7,732,578.

The proteins of the present disclosure may be human proteins. The term "human protein" as used herein refers to proteins having variable and, optionally, constant antibody regions found in humans, e.g. in the human germline or somatic cells or from libraries produced using such regions. The "human" antibodies can include amino acid residues not encoded by human sequences. e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, e.g., as described in U.S. Pat. Nos. 6,300,064 and/or 6,248,516.

The proteins of the present disclosure may be synhumanized proteins. The term "synhumanized protein" refers to a protein prepared by a method described in WO2007/019620. A synhumanized protein includes a variable region of an antibody, wherein the variable region comprises FRs from a New World primate antibody variable region and CDRs from a non-New World primate antibody variable region. For example, a synhumanized protein includes a variable region of an antibody, wherein the variable region comprises FRs from a New World primate antibody variable region and CDRs from a mouse or rat antibody.

The proteins of the present disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

In one example a protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397).

The present disclosure also contemplates a deimmunized protein, e.g., as described in WO2000/34317 and WO2004/108158. De-immunized antibodies and proteins have one or more epitopes, e.g., B cell epitopes or T cell epitopes removed (i.e., mutated) to thereby reduce the likelihood that a subject will raise an immune response against the antibody or protein.

Other Proteins Comprising Antibody Variable Regions

The present disclosure also contemplates other proteins comprising a variable region or antigen binding domain of an antibody, such as:
(i) a single-domain antibody, which is a single polypeptide chain comprising all or a portion of the $V_H$ or a $V_L$ of an antibody (see, e.g., U.S. Pat. No. 6,248,516);
(ii) diabodies, triabodies and tetrabodies. e.g., as described in U.S. Pat. No. 5,844,094 and/or US2008152586;
(iii) scFvs. e.g., as described in U.S. Pat. No. 5,260,203;
(iv) minibodies, e.g., as described in U.S. Pat. No. 5,837,821:
(v) "key and hole" bispecific proteins as described in U.S. Pat. No. 5,731,168;
(vi) heteroconjugate proteins, e.g., as described in U.S. Pat. No. 4,676,980;
(vii) heteroconjugate proteins produced using a chemical cross-linker, e.g., as described in U.S. Pat. No. 4,676,980;
(viii) Fab'-SH fragments, e.g., as described in Shalaby et al, *J. Exp. Med.*, 175: 217-225, 1992; or
(ix) Fab$_3$ (e.g., as described in EP19930302894).

Constant Domain Fusions

The present disclosure encompasses a protein comprising a variable region of an antibody and a constant region or Fc or a domain thereof. e.g., $C_H2$ and/or $C_H3$ domain. Suitable constant regions and/or domains will be apparent to the skilled artisan and/or the sequences of such polypeptides are readily available from publicly available databases. Kabat et al also provide description of some suitable constant regions/domains.

Constant regions and/or domains thereof are useful for providing biological activities such as, dimerization, extended serum half-life e.g., by binding to FcRn (neonatal Fc Receptor), antigen dependent cell cytotoxicity (ADCC), complement dependent cytotoxicity (CDC, antigen dependent cell phagocytosis (ADCP).

The present disclosure also contemplates proteins comprising mutant constant regions or domains, e.g., as described in U.S. Pat. Nos. 7,217,797; 7,217,798; or US20090041770 (having increased half-life) or US2005037000 (increased ADCC).

Stabilized Proteins

Neutralizing proteins of the present disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al. *Proc. Natl. Acad. USA.* 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat Hinge regions of other IgG isotypes may be aligned with the IgG1 sequence by placing the first and last cysteine residues forming inter-heavy chain disulphide (S—S) bonds in the same positions (see for example WO2010/080538).

Additional Protein-Based VEGF-B Signaling Inhibitors

Other proteins that may interfere with the productive interaction of VEGF-B with its receptor include mutant VEGF-B proteins.

In one example, the inhibitor is a soluble protein comprising one or more domains of a VEGF-R1 that bind to VEGF-B (and, e.g., do not substantially bind to VEGF-A). In one example, the soluble protein additionally comprises a constant region of an antibody, such as an IgG1 antibody. For example, the soluble protein additionally comprises a Fc region and, optionally a hinge region of an antibody, e.g., an IgG1 antibody.

In one example, the protein inhibitor is an antibody mimetic. e.g., a protein scaffold comprising variable regions that bind to a target protein in a manner analogous to an antibody. A description of exemplary antibody mimetics follows.

Immunoglobulins and Immunoglobulin Fragments

An example of a compound of the present disclosure is a protein comprising a variable region of an immunoglobulin, such as a T cell receptor or a heavy chain immunoglobulin (e.g., an IgNAR, a camelid antibody).

Heavy Chain Immunoglobulins

Heavy chain immunoglobulins differ structurally from many other forms of immunoglobulin (e.g., antibodies) in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_{HH}$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble.

A general description of heavy chain immunoglobulins from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

V-Like Proteins

An example of a compound of the disclosure is a T-cell receptor. T cell receptors have two V-domains that combine into a structure similar to the Fv module of an antibody. Novotny et al., *Proc Natl Acad Sci USA* 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to an antigen. Such engineered lipocalins are known as anticalins. For further description of anticalins see U.S. Pat. No. 7,250,297B 1 or US20070224633.

Affibodies

In a further example, a compound of the disclosure is an affibody. An affibody is a scaffold derived from the Z domain (antigen binding domain) of Protein A of *Staphylococcus aureus* which can be engineered to bind to antigen. The Z domain consists of a three-helical bundle of approximately 58 amino acids. Libraries have been generated by randomization of surface residues. For further details see EP1641818.

Avimers

In a further example, a compound of the disclosure is an Avimer. Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see WO2002088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Methods for Producing Proteins

Recombinant Expression

In the case of a recombinant protein, nucleic acid encoding same can be cloned into expression vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce an antibody. Exemplary cells used for expressing a protein of the disclosure are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al, Molecular Cloning: A Laboratory Manual. Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding an antibody (e.g., derived from the information provided herein), an enhancer element, a promoter, and a transcription termination sequence. The skilled artisan will be aware of suitable sequences for expression of an antibody. Exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter. Simian virus 40 promoter (SV40), Rous sarcoma virus promoter (RSV). Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomvces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI. USA) amongst others.

The host cells used to produce the antibody may be cultured in a variety of media, depending on the cell type used. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

Protein Purification

Following production/expression, a protein of the disclosure is purified using a method known in the art. Such purification provides the protein of the disclosure substantially free of nonspecific protein, acids, lipids, carbohydrates, and the like. In one example, the protein will be in a preparation wherein more than about 90% (e.g. 95%, 98% or 99%) of the protein in the preparation is a protein of the disclosure.

Standard methods of peptide purification are employed to obtain an isolated protein of the disclosure, including but not limited to various high-pressure (or performance) liquid chromatography (HPLC) and non-HPLC polypeptide isolation protocols, such as size exclusion chromatography, ion exchange chromatography, hydrophobic interaction chromatography, mixed mode chromatography, phase separation methods, electrophoretic separations, precipitation methods, salting in/out methods, immunochromatography, and/or other methods.

In one example, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) is immobilized on a solid support. A sample comprising a protein is then contacted to the immobilized antibody or compound for a time and under conditions sufficient for binding to occur. Following washing to remove any unbound or non-specifically bound protein, the protein is eluted.

In the case of a protein comprising a Fc region of an antibody, protein A or protein G or modified forms thereof can be used for affinity purification. Protein A is useful for isolating purified proteins comprising a human γ1, γ2, or γ4 heavy chain Fc region. Protein G is recommended for all mouse Fc isotypes and for human γ3.

Nucleic Acid-Based VEGF-B Signaling Inhibitors

In one example of the disclosure, therapeutic and/or prophylactic methods as described herein according to any example of the disclosure involve reducing expression of VEGF-B. For example, such a method involves administering a compound that reduces transcription and/or translation of the nucleic acid. In one example, the compound is a nucleic acid. e.g., an antisense polynucleotide, a ribozyme, a PNA, an interfering RNA, a siRNA, a microRNA Antisense Nucleic Acids The term "antisense nucleic acid" shall be taken to mean a DNA or RNA or derivative thereof (e.g., LNA or PNA), or combination thereof that is complementary to at least a portion of a specific mRNA molecule encoding a polypeptide as described herein in any example of the disclosure and capable of interfering with a post-transcriptional event such as mRNA translation. The use of antisense methods is known in the art (see for example, Hartmann and Endres (editors). Manual of Antisense Methodology, Kluwer (1999)).

An antisense nucleic acid of the disclosure will hybridize to a target nucleic acid under physiological conditions. Antisense nucleic acids include sequences that correspond to structural genes or coding regions or to sequences that effect control over gene expression or splicing. For example, the antisense nucleic acid may correspond to the targeted coding region of a nucleic acid encoding VEGF-B, or the 5'-untranslated region (UTR) or the 3'-UTR or combination of these. It may be complementary in part to intron sequences, which may be spliced out during or after transcription, for example only to exon sequences of the target gene. The length of the antisense sequence should be at least 19 contiguous nucleotides, for example, at least 50 nucleotides, such as at least 100, 200, 500 or 1000 nucleotides of a nucleic acid encoding VEGF-B. The full-length sequence complementary to the entire gene transcript may be used. The length can be 100-2000 nucleotides. The degree of identity of the antisense sequence to the targeted transcript should be at least 90%, for example, 95-100%.

Exemplary antisense nucleic acids against VEGF-B are described, for example, in WO2003/105754.

Catalytic Nucleic Acid

The term "catalytic nucleic acid" refers to a DNA molecule or DNA-containing molecule (also known in the art as a "deoxyribozyme" or "DNAzyme") or a RNA or RNA-containing molecule (also known as a "ribozyme" or "RNAzyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are useful in this disclosure are a hammerhead ribozyme and a hairpin ribozyme.

RNA Interference

RNA interference (RNAi) is useful for specifically inhibiting the production of a particular protein. Without being limited by theory, this technology relies on the presence of dsRNA molecules that contain a sequence that is essentially identical to the mRNA of the gene of interest or part thereof, in this case an mRNA encoding a VEGF-B. Conveniently, the dsRNA can be produced from a single promoter in a recombinant vector host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present disclosure is well within the capacity of a person skilled in the art, particularly considering WO99/32619, WO99/53050, WO99/49029, and WO01/34815.

The length of the sense and antisense sequences that hybridize should each be at least 19 contiguous nucleotides, such as at least 30 or 50 nucleotides, for example at least 100, 200, 500 or 1000 nucleotides. The full-length sequence corresponding to the entire gene transcript may be used. The lengths can be 100-2000 nucleotides. The degree of identity of the sense and antisense sequences to the targeted transcript should be at least 85%, for example, at least 90% such as, 95-100%.

Exemplary small interfering RNA ("siRNA") molecules comprise a nucleotide sequence that is identical to about 19-21 contiguous nucleotides of the target mRNA. For example, the siRNA sequence commences with the dinucleotide AA, comprises a GC-content of about 30-70% (for example, 30-60%, such as 40-60% for example about 45%-55%), and does not have a high percentage identity to any nucleotide sequence other than the target in the genome of the mammal in which it is to be introduced, for example as determined by standard BLAST search. Exemplary siRNA that reduce expression of VEGF-B are commercially available from Santa Cruz Biotechnology or Novus Biologicals.

Short hairpin RNA (shRNA) that reduce expression of VEGF-B are also known in the art and commercially available from Santa Cruz Biotechnology.

Screening Assays

Compounds that inhibit VEGF-B signaling can be identified using techniques known in the art, e.g., as described below. Similarly, amounts of VEGF-B signaling inhibitors suitable for use in a method described herein can be determined or estimated using techniques known in the art, e.g., as described below.

Neutralization Assays

For compounds that bind to VEGF-B and inhibit signaling, a neutralization assay can be used.

In one example, a neutralization assay involves contacting VEGF-B with a compound in the presence or absence of detectably labeled soluble VECF-R1 or contacting detectably labeled VEGF-B with a compound in the presence or absence of a cell expressing VEGF-R1 or a soluble VEGF-R1. The level of VEGF-B bound to the VEGF-R1 is then assessed. A reduced level of bound VEGF-B in the presence of the compound compared to in the absence of the compound indicates the compound inhibits VEGF-B binding to VEGF-R1 and, as a consequence VEGF-B signaling.

Another neutralization assay is described in WO2006/012688 and involves contacting a fragment of VEGF-R1 comprising the second Ig-like domain immobilized on a solid support with a subsaturating concentration of recombinant VEGF-B pre-incubated with a compound. Following washing to remove unbound protein, the immobilized protein is contacted with anti-VEGF-B antibody and the amount of bound antibody (indicative of immobilized VEGF-B) determined. A compound that reduces the level of bound antibody compared to the level in the absence of the compound is considered an inhibitor of VEGF-B signaling.

In another example, a compound that inhibits VEGF-B signaling is identified using a cell dependent on VEGF-B signaling for proliferation, e.g., a BaF3 cell modified as described in WO2006/012688 to express a chimeric receptor incorporating the intracellular domain of the human erythropoictin receptor and the extracellular domain of VEGF-R1. Cells are cultured in the presence of VEGF-B and in the presence or absence of a compound. Cell proliferation is then assessed using standard methods, e.g., colony formation assays, thymidine incorporation or uptake of another suitable marker of cell proliferation (e.g., a MTS dye reduction assay). A compound that reduces the level of proliferation in the presence of VEGF-B is considered an inhibitor of VEGF-B signaling.

Compounds can also be assessed for their ability to bind to VEGF-B using standard methods. Methods for assessing binding to a protein are known in the art, e.g., as described in Scopes (In: Protein purification: principles and practice, Third Edition, Springer Verlag, 1994). Such a method generally involves labeling the compound and contacting it with immobilized VEGF-B. Following washing to remove non-specific bound compound, the amount of label and, as a consequence, bound compound is detected. Of course, the compound can be immobilized and the VEGF-B labeled. Panning-type assays can also be used. Alternatively, or additionally, surface plasmon resonance assays can be used.

Expression Assays

A compound that reduces or prevents expression of VEGF-B is identified by contacting a cell with the compound and determining the level of expression of the VEGF-B. Suitable methods for determining gene expression at the nucleic acid level are known in the art and include, for example, quantitative polymerase chain reaction (qPCR) or microarray assays. Suitable methods for determining expression at the protein level are also known in the art and include, for example, enzyme-linked immunosorbent assay (ELISA), fluorescence linked immunosorbent assay (FLISA), immunofluorescence or Western blotting.

In Vivo Assays

Compounds described herein can be tested for activity in animal models. Examples of animals models of type H diabetes and obesity include: the Ob/Ob mouse (monogenic model of obesity, leptin deficient), the db/db mouse (monogenic model of obesity, leptin resistant), the Zucker (fa/fa) rat (monogenic model of obesity, leptin resistant), the Goto-Kakizaki rat, the KK mouse, the NSY mouse, the OLETF rat, the Israeli sand rat, the Fat-fed streptozotocin-treated rat, the CBA/Ca mouse, the Diabetic Torri rat, the New Zealand obese mouse (see Rees and Alcolado *Diabet. Med.* 22, 359-370, 2005).

Known animal models of spontaneous type 2 diabetic nephropathy include: the spontaneously hypertensive/NIH-corpulent (SHR/N-cp) rat (model of obesity, type 2 diabetes and nephropathy), the lean SHR/N-cp rat and the Wistar-Kyoto/NIH-corpulent (WKY/N-cp) rat. Both of these models allow assessment of the role of hypertension and obesity in the pathogenesis of diabetic nephropathy: the SHR/N-cp rats have abnormal glucose tolerance, hypertension, and develop a renal disease reminiscent of human diabetic nephropathy, whereas the WKY/N-cp rats are also obese and have hyperlipidaemia, but their glucose control is less controlled than that of the SHR/N-cp rat). A further model is the LA/N-cp rat (also carries the gene for obesity, and exhibits hyperlipidaemia) (see Kimmel et al. *Acta Diabetologica,* 29, 142-148, 1992). As exemplified herein, the db/db mouse is also an effective model of diabetic nephropathy.

Pharmaceutical Compositions and Methods of Treatment

A compound that inhibits VEGF-B signaling (syn, active ingredient) is useful for parenteral, topical, oral, or local administration, aerosol administration, or transdermal administration, for prophylactic or for therapeutic treatment. In one example, the compound is administered parenterally, such as subcutaneously or intravenously.

Formulation of a compound to be administered will vary according to the route of administration and formulation (e.g., solution, emulsion, capsule) selected. An appropriate pharmaceutical composition comprising compound to be administered can be prepared in a physiologically acceptable carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The compound can be lyophilized for storage and reconstituted in a suitable carrier prior to use according to art-known lyophilization and reconstitution techniques.

The optimum concentration of the active ingredient(s) in the chosen medium can be determined empirically, according to procedures known to the skilled artisan, and will depend on the ultimate pharmaceutical formulation desired.

The dosage ranges for the administration of the compound of the disclosure are those large enough to produce the desired effect. For example, the composition comprises a therapeutically or prophylactically effective amount of the compound.

As used herein, the term "effective amount" shall be taken to mean a sufficient quantity of the compound to inhibit/reduce/prevent signaling of VEGF-B in a subject. The skilled artisan will be aware that such an amount will vary depending on, for example, the compound and/or the particular subject and/or the type and/or the severity of nephropathy being treated. Accordingly, this term is not to be construed to limit the disclosure to a specific quantity, e.g., weight or number of compounds.

As used herein, the term "therapeutically effective amount" shall be taken to mean a sufficient quantity of compound to reduce or inhibit one or more symptoms of nephropathy.

As used herein, the term "prophylactically effective amount" shall be taken to mean a sufficient quantity of compound to prevent or inhibit or delay the onset of one or more detectable symptoms of nephropathy.

In one example, the compound is administered in an amount effective to have one or more of the following effects:

Reduce or prevent hypertension;
Reduce or prevent glomerular and/or tubular sclerosis;
Reduce or prevent mesangial extracellular matrix deposition and/or abnormal thickening of the glomerular basement membrane;
Reduce or prevent glomerular mesangial expansion;
Reduce or prevent glomerular vascular rearrangements;
Reduce or prevent renal lipid accumulation;
Reduce or prevent glomerular lipid accumulation;
Reduce or prevent glomerular collagen deposits and/or arteriolar hyaliosis; and/or
Reduce or prevent macroalbuminuria.

The dosage should not be so large as to cause adverse side effects, such as hyper viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

Dosage can vary from about 0.1 mg/kg to about 300 mg/kg, e.g., from about 0.2 mg/kg to about 200 mg/kg, such as, from about 0.5 mg/kg to about 20 mg/kg, in one or more dose administrations daily, for one or several days.

In some examples, the compound is administered at an initial (or loading) dose which is higher than subsequent (maintenance doses). For example, the compound is administered at an initial dose of between about 1 mg/kg to about 30 mg/kg. The compound is then administered at a maintenance dose of between about 0.0001 mg/kg to about 1 mg/kg. The maintenance doses may be administered every 7-35 days, such as, every 14 or 21 or 28 days.

In some examples, a dose escalation regime is used, in which a compound is initially administered at a lower dose than used in subsequent doses. This dosage regime is useful in the case of subject's initially suffering adverse events In the case of a subject that is not adequately responding to treatment, multiple doses in a week may be administered. Alternatively, or in addition, increasing doses may be administered.

A subject may be retreated with the compound, by being given more than one exposure or set of doses, such as at least about two exposures of the compound, for example, from about 2 to 60 exposures, and more particularly about 2 to 40 exposures, most particularly, about 2 to 20 exposures.

In one example, any retreatment may be given when signs or symptoms of disease return. e.g., when the microalbuminuria progresses.

In another example, any retreatment may be given at defined intervals. For example, subsequent exposures may be administered at various intervals, such as, for example, about 24-28 weeks or 48-56 weeks or longer. For example, such exposures are administered at intervals each of about 24-26 weeks or about 38-42 weeks, or about 50-54 weeks.

A method of the present disclosure may also include co-administration of the at least one compound according to the disclosure together with the administration of another therapeutically effective agent for the prevention or treatment of a renal disorder or complication, nephropathy (e.g. diabetic nephropathy), diabetes, dyslipidemia, hypertension and/or obesity.

In one example, the compound(s) of the disclosure is used in combination with at least one additional known compound which is currently being used or is in development for preventing or treating diabetes. Examples of such known compounds include but are not limited to common anti-diabetic drugs such as sulphonylureas (e.g. glicazide, glipizide), metformin, glitazones (e.g. rosiglitazone, pioglitazone), prandial glucose releasing agents (e.g. repaglinide, nateglinide), acarbose and insulin (including all naturally-occurring, synthetic and modified forms of insulin, such as insulin of human, bovine or porcine origin; insulin suspended in, for example, isophane or zinc and derivatives such as insulin glulisine, insulin lispro, insulin lispro protamine, insulin glargine, insulin detemir or insulin aspart).

In one example, the compound(s) of the disclosure is used in combination with at least one additional known compound which is currently being used or in development for preventing or treating renal disorder such as nephropathy, or an associated disorder or complication. Examples of such known compounds include but are not limited to: ACE inhibitor drugs (e.g. captopril (Capotenm™, enalapril (InnovaceN™), fosinopril (Staril™), lisinopril (Zestril™), perindopril (Coversyl™), quinapril (Accupro™), trandanalopril (Gopten™), lotensin, moexipril, ramipril); RAS blockers; angiotensin receptor blockers (ARBs) (e.g. Olmesartan, Irhbesartan, Losartan, Valsartan, candesartan, eprosartan, telmisartan, etc); protein kinase C (PKC) inhibitors (e.g. ruboxistaurin); inhibitors of AGE-dependent pathways (e.g. aminoguanidine, ALT-946, pyrodoxamine (pyrododorin), OPB-9295, alagebrium); anti-inflammatory agents (e.g. cyclooxigenase-2 inhibitors, mycophenolate mophetil, mizoribine, pentoxifylline), GAGs (e.g. sulodexide (U.S. Pat. No. 5,496,807)); pyridoxamine (U.S. Pat. No. 7,030,146); endothelin antagonists (e.g. SPP 301), COX-2 inhibitors, PPAR-gamma antagonists and other compounds like amifostine (used for cisplatin nephropathy), captopril (used for diabetic nephropathy), cyclophosphamide (used for idiopathic membranous nephropathy), sodium thiosulfate (used for cisplatin nephropathy).

Additionally, the methods of the disclosure may also include co-administration of at least one other therapeutic agent for the treatment of another disease directly or indirectly related to diabetes and/or nephropathy, including but not limited to: dyslipidemia, hypertension, obesity, neuropathy, and/or retinopathy, etc. Additional examples of agents that can be co-administered with the compound(s) according to the invention are corticosteroids; immunosuppressive medications; antibiotics; antihypertensive and diuretic medications (such as ACE-inhibitors); lipid lowering agents such as bile sequestrant resins, cholestyramine, colestipol, nicotinic acid, and more particularly drugs and medications used to reduce cholesterol and triglycerides (e.g. fibrates (e.g. Gemfibrozil™) and HMG-CoA inhibitors such as Lovastatin™, Atorvastatin™, Fluvastatin™, Lescol™), Lipitor™, Mevacor™), Pravacholn™, Pravastatin™, Sinmvastatin™, Zocor™, Cerivastatin™), etc); compounds that inhibit intestinal absorption of lipids (e.g. ezetiminde); nicotinic acid; and Vitamin D.

As will be apparent from the foregoing, the present disclosure provides methods of concomitant therapeutic treatment of a subject, comprising administering to a subject in need thereof an effective amount of a first compound and a second compound, wherein said agent is a compound of the disclosure (i.e., an inhibitor of VEGF-B signaling), and the second agent is for the prevention or treatment of nephropathy, diabetic nephropathy, diabetes, hypertension, hyperlipidemia or obesity.

As used herein, the term "concomitant" as in the phrase "concomitant therapeutic treatment" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human).

In one example, the disclosure also provides a method for treating or preventing nephropathy in a subject, the method comprising administering to the subject a first pharmaceutical composition comprising at least one compound of the disclosure and a second pharmaceutical composition comprising one or more additional compounds.

In one example, a method of the disclosure comprises administering an inhibitor of VEGF-B signaling to a subject suffering from nephropathy (e.g., diabetic nephropathy) and receiving another treatment (e.g., for diabetes).

Kits

Another example of the disclosure provides kits containing compounds useful for the treatment of nephropathy as described above.

In one example, the kit comprises (a) a container comprising a compound that inhibits VEGF-B signaling as described herein, optionally in a pharmaceutically acceptable carrier or diluent; and (b) a package insert with instructions for treating nephropathy in a subject.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating the nephropathy and may have a sterile access port (for example, the container may be an intravenous solution bag or a vial having a stopper pierceable by a hypodermic injection needle). At least one active agent in the composition is the compound that inhibits VEGF-B signaling. The label or package insert indicates that the composition is used for treating a subject eligible for treatment, e.g., one having or predisposed to nephropathy, with specific guidance regarding dosing amounts and intervals of compound and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The kit optionally further comprises a container comprises a second medicament, wherein the compound that inhibits VEGF-B signaling is a first medicament, and which article further comprises instructions on the package insert for treating the subject with the second medicament, in an effective amount. The second medicament may be any of those set forth above.

The present disclosure includes the following non-limiting Examples.

EXAMPLE 1

Mice Deficient in VEGF-B are Resistant to the Development of Diabetic Nephropathy Diabetic Mice Deficient in VEGF-B have Improved Renal Function and Reduced Hypertension C57BKS/Lepr$^{db}$ (db/db//BKS) mice were obtained from Jackson Laboratory (as a model of diabetes and diabetic nephropathy) and bred with C57BL/6-Vegfb$^{-/-}$ mice. Db/db//Vegfb$^{-/-}$ mice were bred by mating heterozygous db/$^+$//Vegfb$^{+/-}$ mice with each other, creating db/db, db/db//Vegfb$^{+/-}$ and db/db//Vegfb$^{-/-}$. 42-weeks old female db/db, db/db//Vegfb$^{+/-}$ and db/db//Vegfb$^{-/-}$ were used in the study. Urine production was measured by photographing cages housing one animal/genotype. To measure glucosuria and proteinuria by dipstick analysis, mice were starved for 1 hr. urine was then collected and the glucose and protein concentration were directly measured using reagent strips according to the manufacturers (Uristix, Siemens). For detection of ACR 20-μl to 200-μl volume of urine was collected from each mouse. Urinary albumin was detected using Albuwell M kit, and urinary creatinine was measured using the Creatinine Companion murine ELISA kit (Exocell, Philadelphia, Pa.). Systolic and diastolic blood pressure was measured by a tail-cuff method using the CODA setup (Kent Scientific). All animals were habituated to the blood pressure measurement device for 2 weeks. They all underwent 1-2 cycle of 20 measurements reordered per day for a minimum of 3 days.

These analyses showed that deletion of Vegfb in diabetic db/db BKS mice improves renal physiology and reduces hypertension. For example, db/db//Vegfb$^{-/-}$ animals produced less urine than db/db, and db/db//Vegfb$^{+/-}$ animals, db/db//Vegfb$^{-/-}$ animals also had less glucose and protein in their urine than db/db, and db/db//Vegfb$^{+/-}$ animals.

FIG. 1A shows urine albumin/creatinine ratio measured by ELISA for db/db, db/db//Vegfb$^{+/-}$ and db/db//Vegfb$^{-/-}$ mice (n=5 group, left graph) and lean wild type and lean Vegfb$^{-/-}$ mice (n=4–6/group, right graph). These data show that db/db//Vegfb$^{-/-}$ animals have an improved urine albumin/creatinine ratio compared to db/db//Vegfb$^{+/-}$ animals. A similar effect was observed in lean animals deficient for Vegfb compared to lean wild-type animals.

Figure 1B:
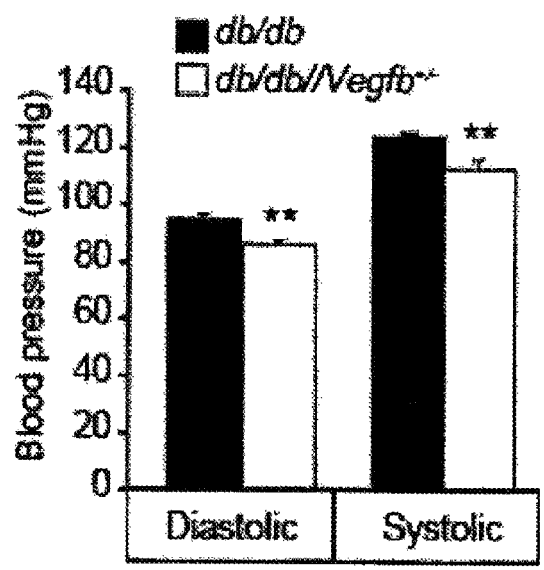
FIG. 1B is a graphical representation showing tail-cuff blood pressure (systolic and diastolic blood pressure; as indicated) in db/db and db/db//Vegfb$^{+/-}$ mice (n=5/group). Values are means±s.e.m. *P<0.05. **P<0.01 compared to db/db controls.

FIG. 1B shows tail-cuff blood pressure (systolic and diastolic blood pressure) in db/db and db/db//Vegfb$^{+/-}$ mice (n=5/group). These data demonstrate that db/db//Vegfb$^{-/-}$ animals have reduced systolic and diasystolic blood pressure compared to db/db animals.

These data show that diabetic db/db mice and lean mice with reduced expression of VEGF-B have an improved kidney function with better filtration capacity as measured by reduced concentration of urinary albumin and urinary albumin/creatinine ratio. The reduced VEGF-B expression also lowered both the systolic and diastolic blood pressure in db/db animals.

Glomerular and Tubular Sclerosis is Decreased Upon Verfb Deletion in Db/Db BKS Mice 42-weeks old female db/db, db/db//Vegfb+/− and db/db//Vegfb−/− mice were sacrificed and kidneys isolated, fixed, embedded, sectioned and stained with Periodic acid-Schiff (PAS) to assess glomerular mesangial expansion and tubular sclerosis according to the manufacturer's instructions (Sigma). At least 10 glomeruli or tubuli per animal, stained for PAS within each section were photographed with bright field microscopy (Axio Vision microscope, Carl Zeiss) at 20× magnification. The glomeruli were quantified using Axio Vision Run wizard program for i) glomerular PAS staining (pixel2/μm2) ii) nr of apoptotic glomeruli per frame. A glomerulus was designated as apoptotic upon intense PAS staining and a diameter lesser than 25 μm. The tubuli were quantified using Axio Vision Run wizard program for i) thickness of tubular basement membrane (μm2).

Figure 2A:
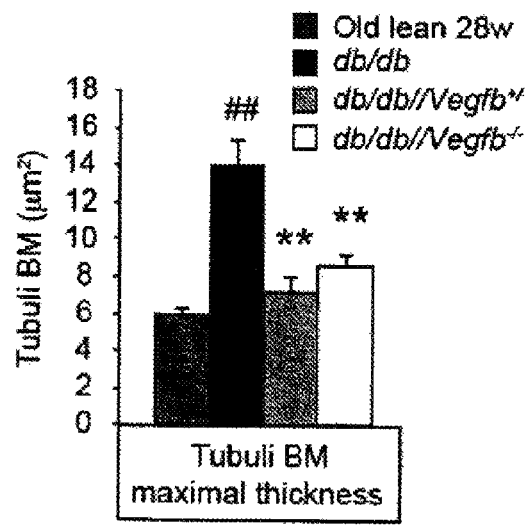
FIG. 2A is a graphical representation showing quantification of abnormalities in the tubuli compartments measured as thickening of tubuli basement membrane (BM) in kidney sections from db/db, db/db//Vegfb$^{+/-}$ and db/db//Vegfb$^{-/-}$ mice. Values are means±s.e.m. *P<0.05, **P<0.01 compared to db/db controls. ## P<0.01 compared to lean 28 week old wild type mice.
Figure 2B:
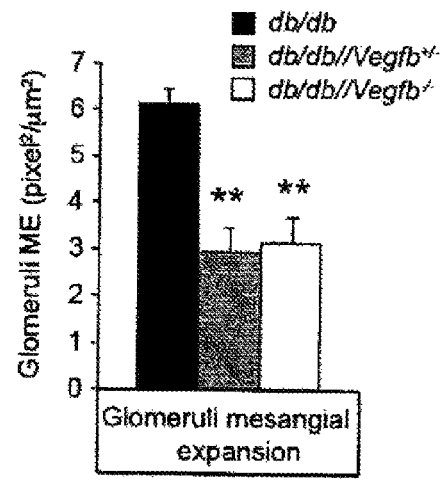
FIG. 2B is a graphical representation showing quantification of glomerular sclerosis as measured as mesangial expansion in kidney sections from db/db, db/db//Vegfb$^{+/-}$ and db/db//Vegf$^{-/-}$ mice. Values are means±s.e.m. *P<0.05. P<0.01, *P<0.001 compared to db/db controls.
Figure 2C:
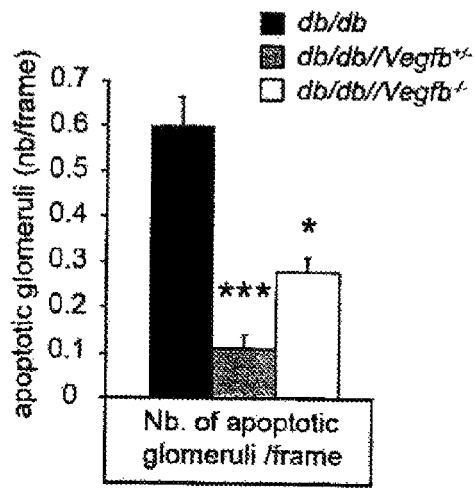
FIG. 2C is a graphical representation showing quantification of glomerular apoptosis measured as apoptotic glomeruli per frame (n=4/group) in kidney sections from db/db, db/db//Vegfb$^{+/-}$ and db/db//Vegfb$^{-/-}$ mice. Values are means±s.e.m. *P<0.05, P<0.01, *P<0.001 compared to db/db controls.

As shown in FIG. 2A db/db mice developed tubular sclerosis, whereas this defect was not observed in db/db//Vegfb$^{+/-}$ and db/db//Vegfb$^{-/-}$ mice. Moreover, db/db mice developed glomerular sclerosis, whereas db/db//Vegfb$^{+/-}$ and db/db//Vegfb$^{-/-}$ mice did not (FIG. 2B). These changes in db/db mice were associated with increased levels of apoptotic glomeruli compared to db/db//Vegfb$^{+/-}$ and db/db//Vegfb$^{-/-}$ mice (FIG. 2C).

These data show that glomerular and tubular sclerosis are decreased in kidneys from diabetic db/db animals with reduced expression of VEGF-B compared to db/db animals.

Mesangial Extracellular Matrix Deposition and Abnormal Thickening of Glomerular Basement Membrane (GBM) are Decreased in Vegfb-Deficient db/db BKS Mice Renal biopsies from 42-weeks old female db/db, db/db//Vegfb$^{+/-}$ and db/db//Vegfb$^{-/-}$ mice were used for transmission electron microscopy (TEM) analysis according to standard procedures. Briefly, tissues were fixed in fixation solution buffer (2% glutaraldehyde, 0.5% paraformaldehyde, 0.1 M cacodylate, 0.1M sucrose, 3 mM CaCl$_2$) and washed in 0.1 M cacodylate buffer pH 7.4 prior to staining in 2% OsO$_4$ in cacodylate buffer for 1 h at room temperature. Samples were dehydrated and en bloc staining was performed in 2% uranyl acetate in absolute ethanol for 1 h at room temperature. Then samples were taken through an Epon 812/acetone series and embedded at 60° C. in pure Epon 812. Thin sections of 70 nm thicknesses were cut on a Leica EM UC6 ultratome and mounted on formvar coated copper slot grids. Post-staining was done with 2% aqueous acetate pH 3.5 and Venable and Cogglesall's lead citrate. Grids were analyzed on a FEI TECNAI electron microscopy.

Figure 3A:
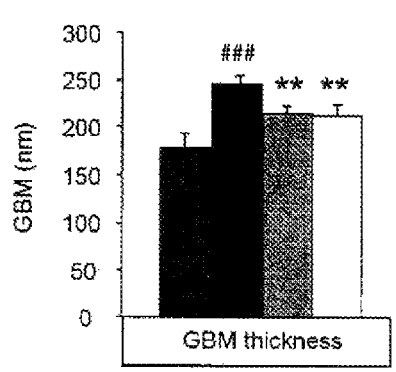
FIG. 3A is a graphical representation showing quantification of glomerular basement membrane thickness as measured using transmission electron microscopy (TEM) analysis of kidney sections from lean wt, db/db, db/db//Vegfb$^{+/-}$ and db/db//Vegfb$^{-/-}$ animals (as indicated). n=3-4/group. Values are means±s.e.m. $^{\#\#\#}$P<0.001 compared to lean db$^+$ controls and **P<0.01 compared to db/db controls.
Figure 3B:
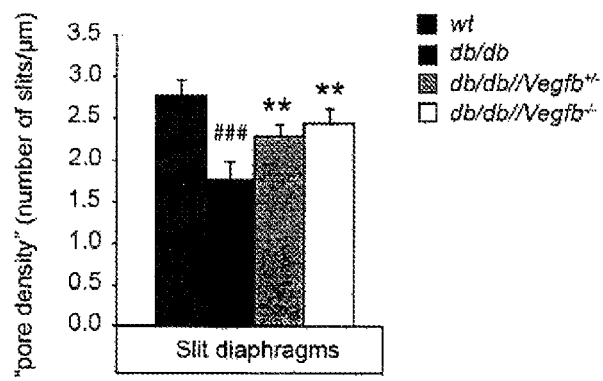
FIG. 3B is a graphical representation showing quantification of the number of slits as measured using transmission electron microscopy (TEM) analysis of kidney sections from lean wt, db//db, db/db//Vegf$^{+/-}$ and db/db//Vegfb$^{-/-}$ animals (as indicated). n=3-4/group. Values are means± s.e.m. $^{\#\#\#}$P<0.001 compared to lean db$^+$ controls and **P<0.01 compared to db/db controls.

High magnification TEM analysis showed that renal abnormalities associated with diabetic nephropathy, such as mesangial expansion and thickening of GBM are reduced in db/db mice with reduced expression of VEGF-B compared to db/db mice (FIG. 3A). Thickening of the GBM is a common feature in diabetic nephropathy. FIG. 3B shows that slit formation is preserved in db/db mice with reduced expression of VEGF-B. Podocyte formation was also found to be preserved in db/db mice with reduced expression of VEGF-B.

Deletion of Vegfb reduces renal lipid accumulation in db/db BKS mice

Oil red O (ORO) analysis was performed using kidneys from 42-week old female d/db, db/db//Vegfb$^{+/-}$, db/db//Vegfb$^{-/-}$ and lean wild type mice. Briefly, kidneys were dissected and flash frozen on dry ice and embedded in Tissue-Tek® (Sakura) directly on the mold of the cryostat. Cryosections (12 μm) were immersed 5-15 min in ORO working solution (2.5 g oil red O (Sigma-Aldrich), dissolved in 400 ml 99% isopropanol, further diluted 6:10 in H2O, filtered through a 22 μm filter (Corning)) and rinsed 10 min under running tap water before they were mounted. Stained sections were examined with bright field microscopy (Axio Vision microscope, Carl Zeiss) at 20× magnification and a minimum of 10 frames per section was captured. For quantification of lipid droplets, the amount of red pixels in each frame was quantified using Axio Vision Run wizard program for total ORO staining (pixel, a.u).

Figure 4A:
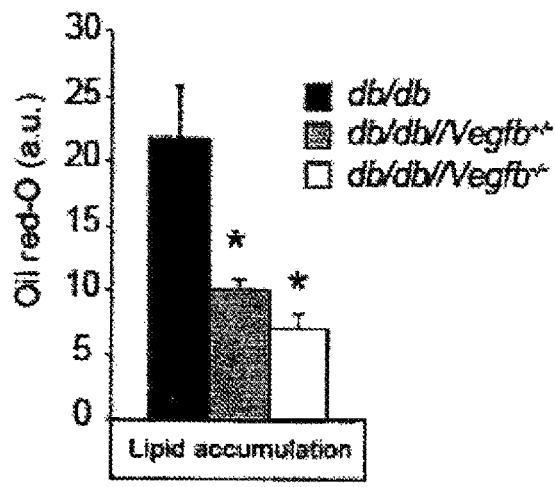
FIG. 4A is a graphical representation showing quantification of oil red O (ORO) analysis of kidney sections from db/db, db/db//Vegfb$^{+/-}$ and db/db//Vegfb$^{-/-}$ animals. Values are means±s.e.m. *P<0.05 compared to db/db controls.
Figure 4B:
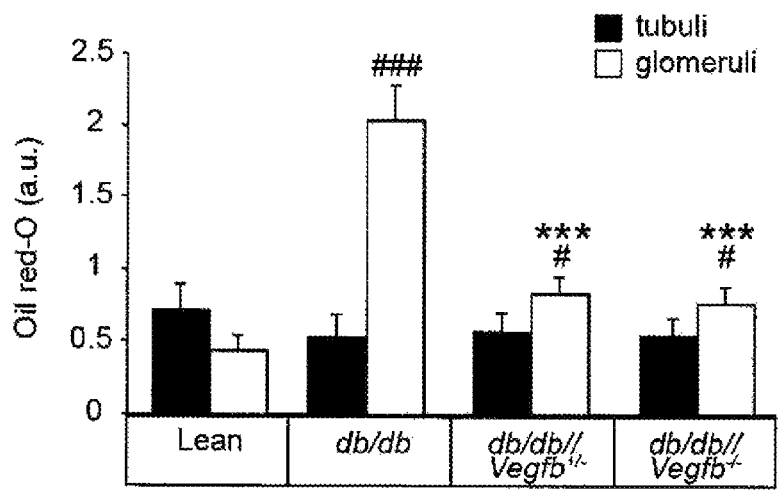
FIG. 4B is a graphical representation showing quantification of oil red O staining in glomeruli and tubular compartments (as indicated), db/db, db/db//Vegfb$^{+/-}$, db/db//Vegfb$^{-/-}$ and wild type animals. Values are means± s.e.m. $^\#$P<0.05 and $^{190}$ $^{\#\#}$P<0.001 compared to lean controls. ***P<0.001 compared to db/db controls.

Renal lipid droplet accumulation and structure are ameliorated in db/db mice with reduced expression of VEGF-B (FIG. 4A). In particular, the lipid droplets are fewer and smaller in kidney sections from Vegfb deficient db/db mice. FIG. 4B shows that reducing VEGF-B expression in db/db mice decreases the lipid accumulation in the glomeruli and presents fewer and smaller lipid droplets.

Glomerular Rearrangements are Prevented in db/db BKS Mice Deficient in Vegfb

Glomerular morphology was assessed in kidneys from 42-weeks old female db/db, db/db//Vegfb$^{+/-}$ and db/db//Vegfb$^{-/-}$ mice. Briefly, animals were sacrificed and kidneys collected, fixed in 4% PFA for 48 hrs, embedded and 3 µm sections prepared and thereafter immunostained for synaptopodin and/or pecam. Antigen retrieval was performed on 3 µm sections using Antigen retrieval solution Ph6 (Dako) and heated at 98° C. for 10 minutes. Sections were incubated at 4° C. for 12 hrs with primary antibodies rabbit anti-synaptopodin (Santa Cruz), goat anti-pecam (Abcam) Appropriate fluorescently labeled secondary antibodies (Invitrogen, Alexa fluor) were applied and sections were further incubated for 1 hrs at RT after which they were prepared for microscopy. At least 10 glomeruli per animal stained for synaptopodin and pecam within each section were photographed with an Axio Vision microscope (Carl Zeiss) at 40× magnification. The glomeruli were quantified using Axio Vision Run wizard program for glomerular i) synaptopodin staining (pixel$^2$/µm$^2$) and glomerular ii) pecam staining (pixel$^2$/µm$^2$).

Figure 5A:
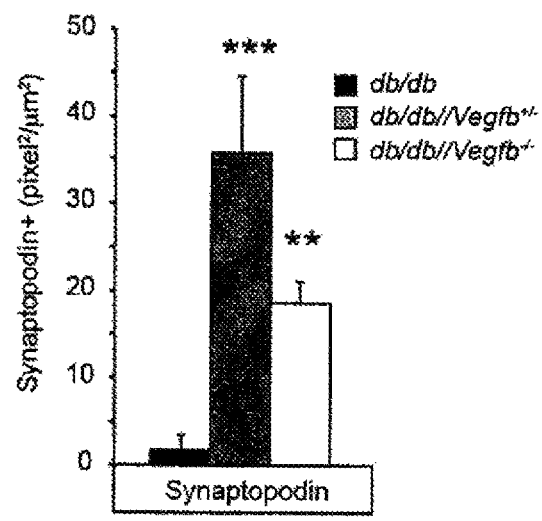
FIG. 5A is a graphical representation showing quantification of synaptopodin staining in glomeruli from db/db, db/db//Vegfb$^{+/-}$ and db/db//Vegfb$^{-/-}$. Values are means±s.e.m. *P<0.05. P<0.01. *P<0.001 compared to db/db controls.
Figure 5B:
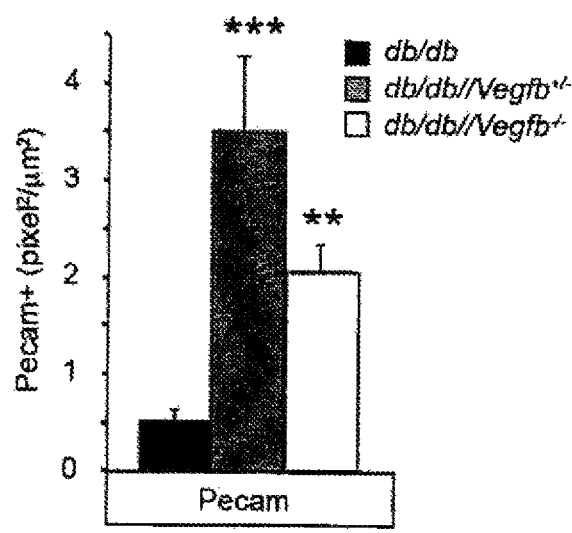
FIG. 5B is a graphical representation showing quantification of pecam staining in glomeruli from db/db, db/db//Vegfb$^{+/-}$ and db/db//Vegfb$^{-/-}$. Values are means±s.e.m. *P<0.05, P<0.01, *P<0.001 compared to db/db controls.

FIGS. 5A and 5B show increased expression of synaptopodin and pecam in glomeruli of db/db//Vegfb$^{+/-}$ and db/db//Vegfb$^{-/-}$ mice. These data and analysis of stained glomeruli indicate that overall glomeruli morphology is improved in Vegfb deficient db/db mice. Expression and structure of podcoytes and endothelial cells, i.e., cell types that are crucial for the filtration process, are preserved in db/db mice with reduced expression of VEGF-B.

Glomerular Collagen Deposits and Arteriolar Hyalinosis are Reduced in Vegfb-Deficient db/db BKS Mice Glomerular collagen deposits and arteriolar hyalinosis were assessed in kidneys from 42-weeks old female db/db, db/db//Vegfb$^{+/-}$ and db/db//Vegfb$^{-/-}$ mice. Briefly, animals were sacrificed and kidneys collected, fixed in 4% PFA for 48 hrs. embedded and 3 µm sections prepared and thereafter immunostained for collagen IV, pecam and/or α-SMA. Briefly, antigen retrieval was performed on 3 µm sections using Antigen retrieval solution Ph6 (Dako #S2367) and heated at 98° C. for 10 minutes. Sections were incubated at 4° C. for 12 hrs with primary antibodies rabbit anti-collagen IV (abcam), goat anti-pecam (ahcam) or α-SMA (Sigma). Appropriate fluorescently labeled secondary antibodies (Invitrogen, Alexa fluor) were applied and sections were further incubated for 1 hr at RT after which they were prepared for microscopy. At least 10 glomeruli per animal stained for collagen IV, pecam or α-SMA within each section were photographed with an Axio Vision microscope (Carl Zeiss) at 40× magnification. The glomeruli were quantified using Axio Vision Run wizard program for glomerular i) collagen IV staining (pixel$^2$/µm$^2$), glomerular ii) α-SMA staining (pixel$^2$/µm$^2$) iii) thickness of glomerular arterioles (µm$^2$).

Figure 6A:
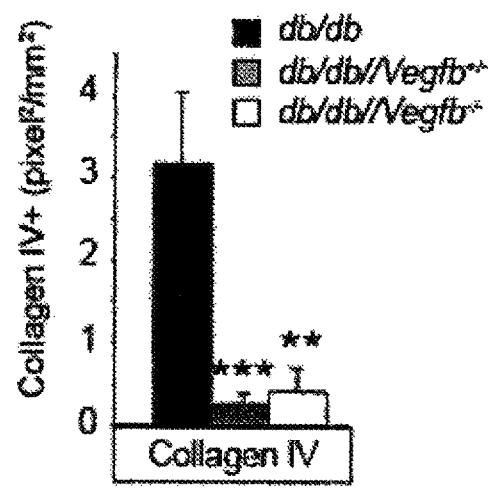
FIG. 6A is a graphical representation showing quantification of collagen IV staining in glomeruli in kidney sections from db/db, db/db//Vegfb$^{+/-}$ and db/db//Vegfb$^{+/-}$ mice. Values are means±s.e.m. *P<0.05, P<0.01, *P<0.001 compared to db/db controls.
Figure 6B:
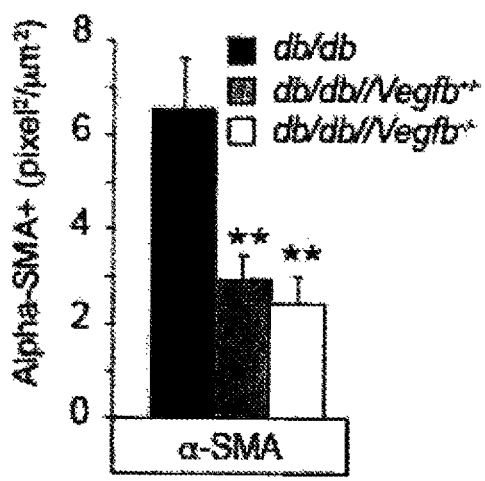
FIG. 6B is a graphical representation showing quantification of α-SMA staining in glomeruli in kidney sections from db/db, db/db//Vegfb$^{+/-}$ and db/db//Vegfb$^{-/-}$ mice. Values are means±s.e.m. *P<0.05, P<0.01, *P<0.001 compared to db/db controls.
Figure 6C:
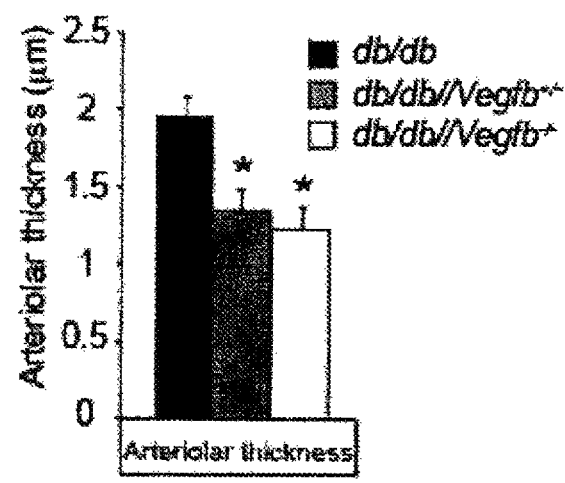
FIG. 6C is a graphical representation showing arteriolar thickness in kidney sections from db/db, db/db//Vegfb$^{+/-}$ and db/db//Vegfb$^{-/-}$ mice. Values are means±s.e.m. *P<0.05 compared to db/db controls.

FIG. 6 shows that levels of collagen IV (FIG. 6A) and α-SMA (FIG. 6B) were reduced in db/db//Vegfb$^{+/-}$ and db/db//Vegfb$^{-/-}$ mice compared to db/db mice. Furthermore, arteriolar thickness was reduced in db/db//Vegfb$^{+/-}$ and db/db//Vegfb$^{-/-}$ mice compared to db/db mice (FIG. 6C). These data indicate that pathological intra-glomerular collagen deposition (also known as glomerular extracellular matrix (ECM) deposits) and arteriolar hyalinosis are reduced in db/db mice with reduced expression of VEGF-B. These data show that common histological pathologies of diabetic nephropathy, such as glomerular ECM deposits and arteriolar hyalinosis are reduced in db/db mice with reduced expression of VEGF-B.

Lipids Accumulate Preferentially in the Kidney Glomeruli During Progression of Diabetic Nephropathy in db/db/BKS Mice Lean db$^+$. 6-weeks old db/db and 21-weeks old db/db//BKS mice were used for Oil red O (ORO) analysis. Kidneys were dissected and flash frozen on dry ice and embedded in Tissue-Tek® (Sakura) directly on the mold of the cryostat. Cryosections (12 µm) were immersed 5-15 min in oil red O working solution (2.5 g oil red O (Sigma-Aldrich), dissolved in 400 ml 99% isopropanol, further diluted 6:10 in H$_2$O, filtered through a 22 µm filter (Corning)) and rinsed 10 min under running tap water before they were mounted. Stained sections were examined with bright field microscopy (Axio Vision microscope, Carl Zeiss) at 20× magnification and a minimum of 10 frames per section was captured. For quantification of lipid droplets, the amount of red pixels in each frame was quantified using Axio Vision Run wizard program for total ORO staining (pixel, a.u).

Figure 7:
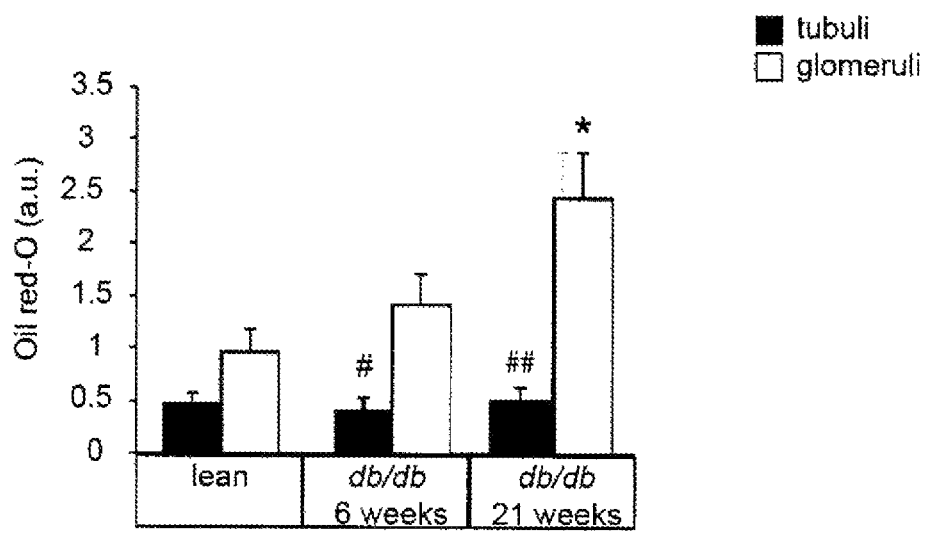
FIG. 7 is a graphical representation showing results of quantification of ORO staining both in the glomeruli and in the tubular compartment of lean wild type, db/db//BKS 6-weeks and db/db//BKS 21-weeks mice. n=5-7. Values are means±s.e.m. $^\#$P<0.05 and $^{\#\#}$P<0.01, tubuli compared to glomeruli. *P<0.05 glomeruli db/db//BKS 6-weeks compared to glomeruli db/db//BKS 21-weeks.

FIG. 7 shows that as macroalbuminuria develops in db/db//BKS mice, lipids accumulate preferentially in the glomeruli.

Glomerular Lipid Accumulation Correlates with Podocyte Loss in Progression of Diabetic Nephropathy in db/db//BKS Mice Lean db$^+$. 6-weeks old db/db and 21-weeks old db/db//BKS mice were used for analysis. Kidneys were dissected, fixed in 4% PFA for 48 h and subsequently processed for paraffin embedding using standard procedures. After embedding, 3-µm sections were prepared and thereafter immunostained for synaptopodin and/or pecam. Briefly, antigen retrieval was performed on 3 µm sections using antigen retrieval solution pH6 (Dako) and heated at 98° C. for 10 minutes. Sections were incubated at 4° C. for 12 h with primary antibodies guinea pig anti-adipophilin (Fitzgerald) and rabbit anti-synaptopodin (Santa Cruz) Appropriate fluorescently labeled secondary antibodies (Invitrogen. Alexa fluor) were applied and sections were further incubated for 1 h at RT after which they were prepared for microscopy. At least 10 glomeruli per animal stained for adipophilin and synaptopodin within each section were photographed with an Axio Vision microscope (Carl Zeiss) at 40× magnification. The glomeruli were quantified using Axio Vision Run wizard program for glomerular i) adipophilin staining (pixel$^2$/µm$^2$) and ii) synaptopodin staining (pixel$^2$/µm).

Figure 8:
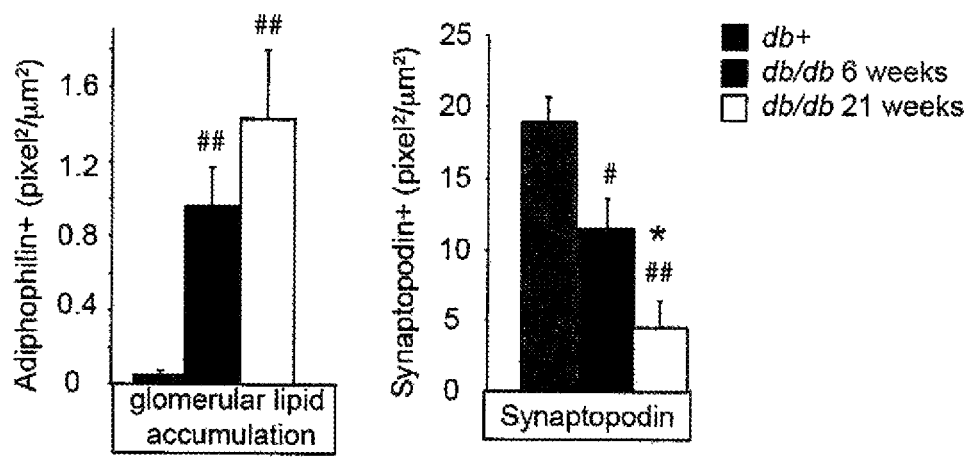
FIG. 8 includes two graphical representations showing glomerular lipid accumulation correlates with podocyte loss in progression of DN in db/db//BKS mice. The left hand graph shows quantification of adipophilin staining and the right hand graph shows quantification of synaptopodin staining. n=3–5/group Values are means±s.e.m. #P<0.05, ##P<0.01, compared to lean db+ controls. *P<0.05 db/db//BKS 6-weeks compared to glomeruli db/db//BKS 21-weeks.

FIG. 8 shows that during the development of diabetic nephropathy, lipids accumulate in the glomeruli and podocyte number declines in parallel.

The Vegfb Signalling Pathway is Upregulated During the Progression of Diabetic Nephropathy Kidneys from lean db$^+$, and 6-, 12- and 21-weeks old db/db//BKS mice were dissected and flash frozen on dry ice. Total RNA was extracted and purified from kidneys using the RNeasy Mini kit (Qiagen) according to the manufacturer's instructions. First strand cDNA was synthesized from 0.5-1 µg total RNA using iScript cDNA Synthesis Kit (Bio-Rad). Real-Time quantitive PCR was performed using KAPA SYBR FAST qPCR Kit Master Mix (2×) Universal (KAPA Biosystems) in Rotor-Gene Q (Qiagen) Real-Time PCR thermal cycler according to the manufacturer's instructions. Expression levels were normalized to the expression of L19 and β-2 microbulin.

Figure 9:
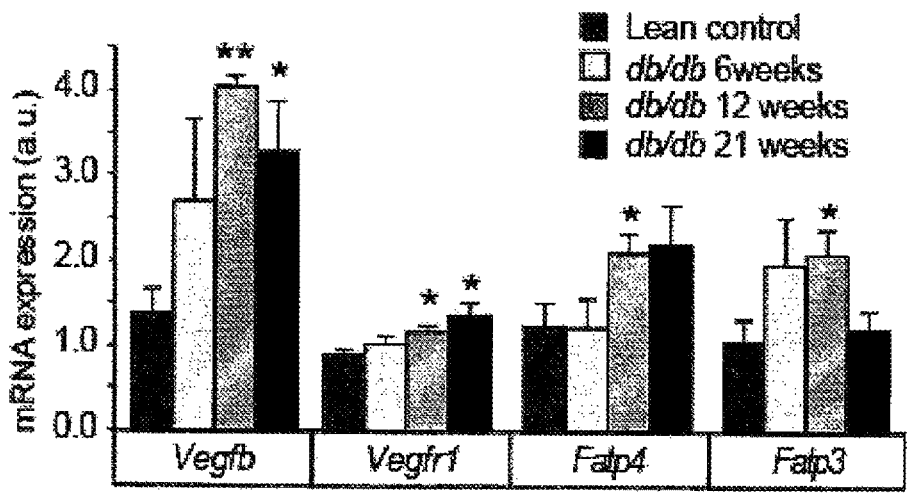
FIG. 9 is a graphical representation showing relative renal mRNA expression of Vegfb, Vegfr1, Fatp4 and Fatp3 in lean db*, and 6-, 12- and 21-weeks old db/db//BKS (as indicated). Values are means±s.e.m. *P<0.05. **P<0.01, compared with lean control animals. Vegfb, vascular endothelial growth factor B; Vegfr1, vascular endothelial growth factor receptor 1; Fatp3, fatty acid transporter 3; Fatp4, fatty acid transporter 4.

As shown in FIG. 9, in diabetic nephropathy, renal expression of Vegfb, the downstream targets of VEGF-B.

Fatp3 and Fatp4, and the main VEGF-B receptor, Vegfr1 are upregulated. These data indicate that the renal VEGF-B signaling pathway is a suitable target for treating diabetic nephropathy.

Renal function is improved in high fat fed Vegf-b$^{+/-}$ mice and Vegf-b$^{-/-}$ mice Male wild type, Vegf$^{+/-}$ and Vegfb$^{+/-}$ mice where fed 60% high fat diet (HFD) (Research Diets. USA) for 30 weeks, started at age 5 weeks. The study included lean wild type control animals as well. For detection of ACR 20-μl to 200-μl volume of urine was collected from each mouse. Urinary albumin was detected using Albuwell M kit, and urinary creatinine was measured using the Creatinine Companion murine ELISA kit (Exocell, Philadelphia, Pa.).

Figure 10A:
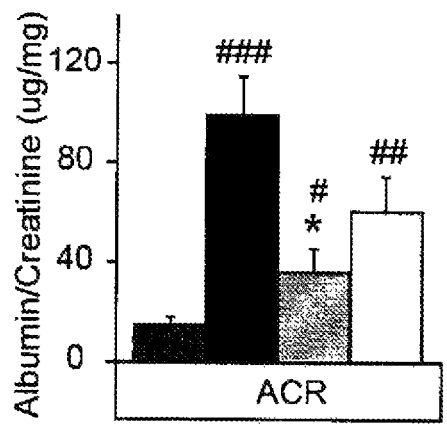
FIG. 10A is a graphical representation showing analysis of urine albumin/creatinine ratio in high fat diet (HFD) fed WT, HFD fed Vegfb$^{+/-}$ HFD fed Vegfb$^{-/-}$ mice and lean control animals. Values are means±s.e.m. #P<0.05. ##P<0.01, ###P<0.001 compared to lean control animals. *P<0.05, **P<0.01 compared to wt HFD fed.
Figure 10B:
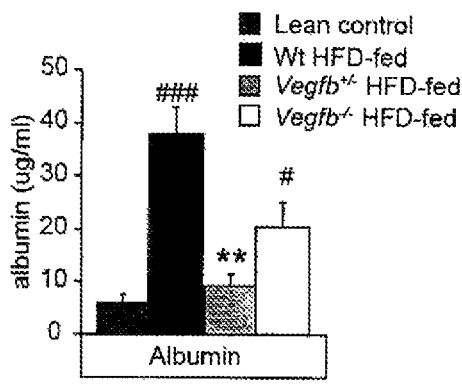
FIG. 10B is a graphical representation showing analysis of urine albumin in HFD fed WT, HFD fed Vegfb$^{+/-}$ HFD fed Vegfb$_{-/-}$ mice and lean control animals. Values are means±s.e.m. #P<0.05, ##P<0.01, ###P<0.001 compared to lean control animals. *P<0.05, **P<0.01 compared to wt HFD fed.

FIG. 10 shows that HFD-mediated leakage of urinary protein was reduced in HFD fed mice with reduced expression of VEGF-B. Thus kidney filtration capacity was improved as measured both by albumin excretion (FIG. 10B) and ACR (FIG. 10A).

Glomerular Mesangial Expansion and Hypertrophy are Decreased in HFD Fed Vegf-b$^{+/-}$ and Vegf-b$^{-/-}$ Mice Male wild type, Vegfb$^{+/-}$ and Vegfb$^{-/-}$ mice were fed 60% HFD (Research Diets. USA) for HFD for 30 weeks, started at age 5 weeks. The study also included lean control animals. Animals were sacrificed by isofluorane anaesthetics and total blood was removed by cardiac puncture. Kidneys were dissected, fixed in 4% PFA for 48 h and subsequently processed for paraffin embedding using standard procedures. After embedding, 3-μm sections were prepared and stained with PAS (Sigma) according to the manufacturer. At least 10 glomeruli per animal stained for PAS within each section were photographed with bright field microscopy (Axio Vision microscope, Carl Zeiss) at 40× magnification. The glomeruli were quantified using Axio Vision Run wizard program for glomerular PAS staining (pixel$^2$/lμm$^2$).

Figure 11A:
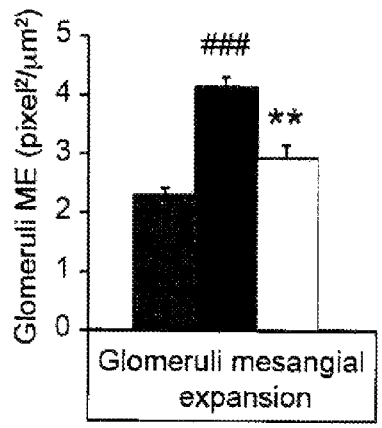
FIG. 11A is a graphical representation showing quantification of glomerular mesangial expansion in HFD fed Vegf-b$^{+/-}$ and Vegf-b$^{-/-}$ mice. Analysis of HFD fed WT, Vegfb$^{+/-}$, Vegfb$^{-/-}$ mice and lean control animals. n=5–10/group. Values are means±s.e.m. Scale bars, 50 mm. #P<0.05. ###P<0.001 compared to lean control animals, **P<0.01 compared to wt HFD fed.
Figure 11B:
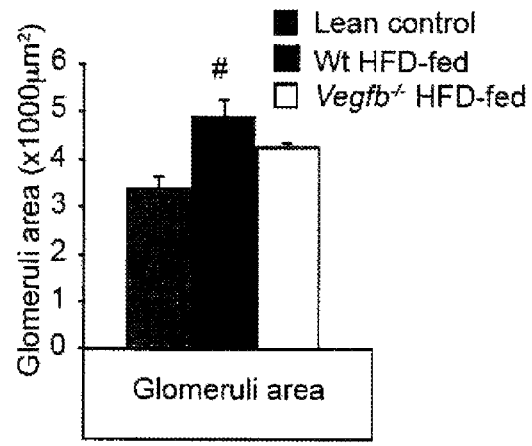
FIG. 11B is a graphical representation showing quantification of glomerular area in HFD fed Vegf-b$^{+/-}$ and Vegf-b$^{-/-}$ mice. Analysis of HFD fed WT, Vegfb$^{+/-}$, Vegfb$^{-/-}$ mice and lean control animals. n=5–10/group. Values are means±s.e.m. Scale bars, 50 mm. #P<0.05, ###P<0.001 compared to lean control animals. **P<0.01 compared to wt HFD) fed.

FIG. 11 shows that HFD induced renal glomerular mesangial expansion (FIG. 11A) and hypertrophy (FIG. 11B) are prevented in HFD fed mice with reduced expression of VEGF-B.

Glomerular Lipid Accumulation is Reduced in in HFD Fed Vegf-b$^{+/-}$ and Vegf-b$^{-/-}$ Mice Male wild type, Vegfb$^{+/-}$ and Vegfb$^{-/-}$ mice where fed 60% HFD (Research Diets, USA) for HFD for 30 weeks, started at age 5 weeks. The study also included lean wild type control animals. Animals were sacrificed by isofluorane anaesthetics and total blood was removed by cardiac puncture. Kidneys were dissected and flash frozen on dry ice and embedded in Tissue-Tek@ (Sakura) directly on the mold of the cryostat. Cryosections (12 μm) were immersed 5-15 min in oil red O working solution (2.5 g oil red O (Sigma-Aldrich), dissolved in 400 ml 99% isopropanol, further diluted 6:10 in H$_2$O, filtered through a 22 μm filter (Corning)) and rinsed 10 min under running tap water. Thereafter the sections were submerged for 3 s in hematoxylin solution and rinsed under tap water before they were mounted. Stained sections were examined with bright field microscopy. At least 10 glomeruli per animal stained for ORO and hematoxylin within each section were photographed with an Axio Vision microscope (Carl Zeiss) at 40× magnification. The glomeruli were quantified using Axio Vision Run wizard program for glomerular ORO staining (pixel$^2$/μm$^2$).

Figure 12:
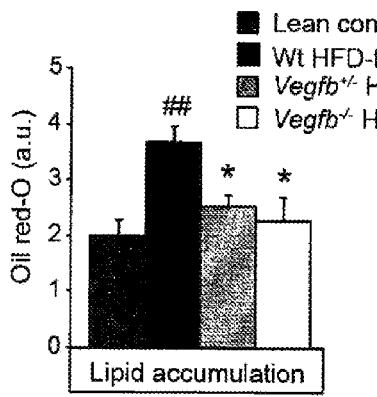
FIG. 12 is a graphical representation showing quantification of ORO staining of kidney sections from HFD fed WT, HFD fed Vegfb$^{+/-}$, HFD fed Vegfb$^{-/-}$ mice and lean control animals. n=5–10/group. Values are means±s.e.m. ##P<0.01 compared to lean control animals. *P<0.05 compared to wt HFD fed.

FIG. 12 and analysis of stained kidney sections shows that HFD increases renal lipid accumulation mostly in the glomeruli. However, this ectopic lipid accumulation is reduced in HFD fed mice with reduced expression of VEGF-B. The lipid droplets were reduced both in number and size.

Glomerular Lipid Accumulation is Reduced, and Podocyte Integrity is Preserved in HFD Fed Vegf-b$^{+/-}$ and Vegf-b$^{-/-}$ Mice Male wild type, Vegf$^{+/-}$ and Vegfb$^{-/-}$ mice were fed 60% HFD (Research Diets. USA) for HFD for 30 weeks, starting at age 5 weeks. The study additionally included lean wild type control animals. Animals were sacrificed by isofluorane anaesthetics and total blood was removed by cardiac puncture. Kidneys were dissected, fixed in 4% PFA for 48 h and subsequently processed for paraffin imbedding using standard procedures. After embedding, 3-μm sections were prepared and thereafter immunostained for synaptopodin and/or pecam. Briefly, antigen retrieval was performed on 3 μm sections using Antigen retrieval solution Ph6 (Dako) and heated at 98° C. for 10 minutes. Sections were incubated at 4° C. for 12 h with primary antibodies guinea pig anti-adipophilin (Fitzgerald) and rabbit anti-podocin (Sigma) Appropriate fluorescently labeled secondary antibodies (Invitrogen. Alexa flouor) were applied and sections were further incubated for 1 h at RT after which they were prepared for microscopy. At least 10 glomeruli per animal stained for adipophilin and synaptopodin within each section were photographed with an Axio Vision microscope (Carl Zeiss) at 40× magnification. The glomeruli were quantified using Axio Vision Run wizard program for glomerular i) adipophilin staining (pixel$^2$/μm$^2$) and ii) podocin staining (pixel$^2$/μm$^2$).

Figure 13:
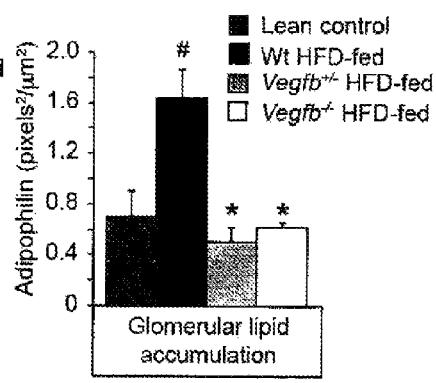
FIG. 13 is a graphical representation showing quantification of adipophilin staining in glomeruli of kidney sections from HFD fed WT, HFD fed Vegfb$^{+/-}$, HFD fed Vegfb$^{-/-}$ mice and lean control animals. Values are means±s.e.m. #P<0.05 compared to lean control animals. *P<0.05 compared to wt HFD fed.

FIG. 13 and analysis of stained sections shows that HFD driven ectopic renal lipid accumulation is reduced in mice with reduced expression of VEGF-B. In parallel the structural integrity and numbers of podocytes are increased.

Glomerular ECM Deposits and Arteriolar Hyalinosis are Reduced in HFD Fed Vegf-b$^{+/-}$ and Vegf-b$^{-/-}$ Mice Male wild type, Vegf$^{+/-}$ and Vegfb$^{-/-}$ mice were fed 60% HFD) (Research Diets, USA) for HFD for 30 weeks, starting at age 5 weeks. The study included lean wild typecontrol animals as well. Animals were sacrificed by isofluorane anaesthetics and total blood was removed by cardiac puncture. Kidneys were dissected, fixed in 4% PFA for 48 h and subsequently processed for paraffin imbedding using standard procedures. After embedding, 3-μm sections were prepared and thereafter immunostained for collagen IV, pecam and/or α-SMA Briefly, antigen retrieval was performed on 3 μm sections using Antigen retrieval solution Ph6 (Dako #82367) and heated at 98° C. for 10 minutes. Sections were incubated at 4° C. for 12 h with primary antibodies rabbit anti-collagen IV (abcam), goat anti-pecam (abeam) or α-SMA (sigma). Appropriate fluorescently labeled secondary antibodies (Invitrogen. Alexa fluor) were applied and sections were further incubated for 1 hr at RT after which they were prepared for microscopy. At least 10 glomeruli per animal stained for collagen IV, pecam or α-SMA within each section were photographed with an Axio Vision microscope (Carl Zeiss) at 40× magnification. The glomeruli were quantified using Axio Vision Run wizard program for glomerular i) collagen IV staining (pixel$^2$/μm) and ii) thickness of glomerular arterioles (μm$^2$).

Figure 14A:
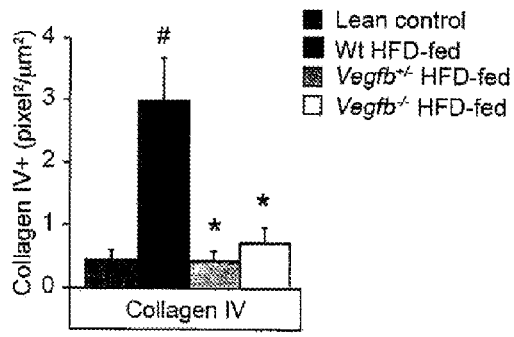
FIG. 14A is a graphical representation showing quantification of collagen IV staining in kidney sections from HFD fed WT. HFD fed Vegfb$^{+/-}$, HFD fed Vegfb$^{-/-}$ mice and lean control animals. n=5–10/group. Values are means±s.e.m. #P<0.05, ##P<0.01 compared to lean control animals. *P<0.05, **P<0.01 compared to wt HFD fed.
Figure 14B:
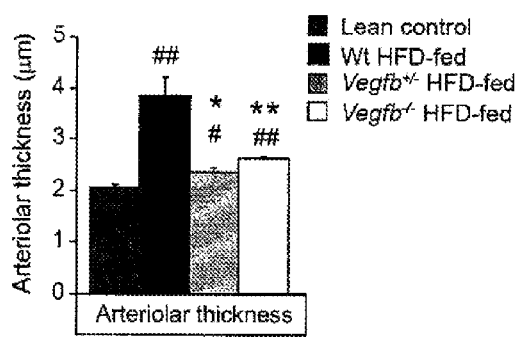
FIG. 14B is a graphical representation showing quantification of arteriolar thickness in kidney sections from HFD fed WT, HFD fed Vegfb$^{+/-}$, HFD fed Vegfb$^{-/-}$ mice and lean control animals. n=5–10/group. Values are means±s.e.m. #P<0.05, ##P<0.01 compared to lean control animals. *P<0.05, **P<0.01 compared to wt HFD fed.

FIG. 14 and analysis of stained sections show that key histological pathologies in diabetic nephropathy such as increased glomerular ECM accumulation (FIG. 14A) and arteriolar hyalinosis (FIG. 14B) are reduced in HFD) fed mice with reduced expression of VEGF-B.

EXAMPLE 2

A Neutralizing Anti-VEGF-B Antibody Treats or Prevents Progression of Diabetic Nephropathy Antibody-Mediated Inhibition of VEGF-B Moderately Influences Blood Glucose Levels in Diabetic Db/Db//BKS Mice C57BKS/Leprdb (db/db/BKS) mice were purchased from Jackson Laboratory and injected intraperitoneally twice weekly, starting at 6 (preventative trial) or 12 (therapeutic trial) weeks of age and continued for 8 weeks with 400 µg of either 2H10 (neutralizing anti-VEGF-B antibody) or isotype-matched control antibody. In the preventive trial, start values of ACR and blood glucose were <50 µg albumin/mg creatinine and <15 mM, respectively. In the therapeutic trial, start values of ACR and blood glucose were >150 µg albumin/mg creatinine and >15 mM, respectively. Postprandial blood glucose levels of mice were monitored bi-weekly after removal of food for 2 hrs. Glucose measurements were performed on blood drawn from the tail vein using a Bayer Contour Glucose meter. For detection of ACR 20-µl to 200-µl volume of urine was collected from each mouse. Urinary albumin was detected using Albuwell M kit, and urinary creatinine was measured using the Creatinine Companion murine ELISA kit (Exocell, Philadelphia, Pa.).

Figure 15A:
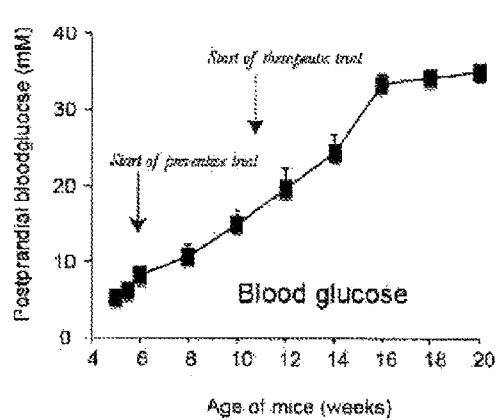
FIGS. 15A-F are graphical representations showing analysis of db/db//BKS mice that were treated with anti-VEGF-B (2H10) or control antibody (labeled as "C") for 8 weeks.

FIGS. 15A and C-F show blood glucose levels of db/db/BKS mice treated therapeutically or prophylactically with antibody 2H10. As shown, administration of the antibody after diabetes had progressed in the experiments described herein (as in the aggressive models of diabetes used herein) did not substantially reduce blood glucose levels.

Figure 15B:
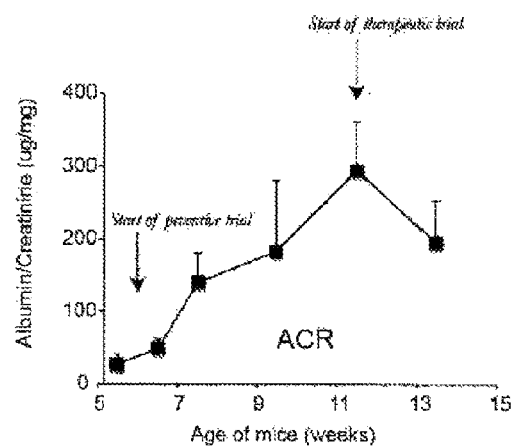
Figure 15C:
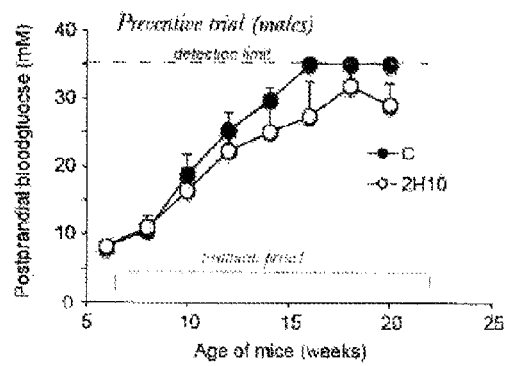
Figure 15D:
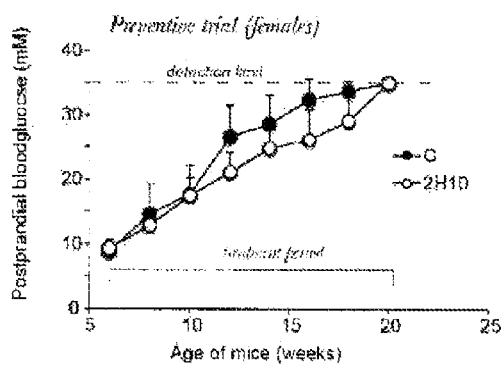
Figure 15E:
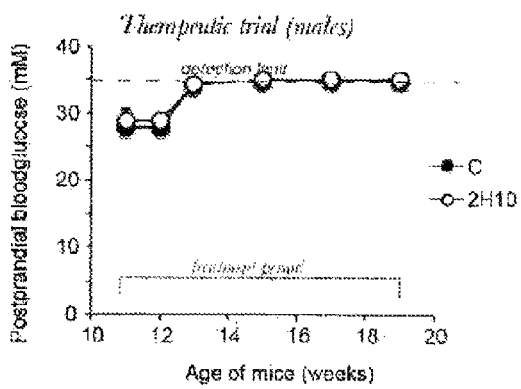
Figure 15F:
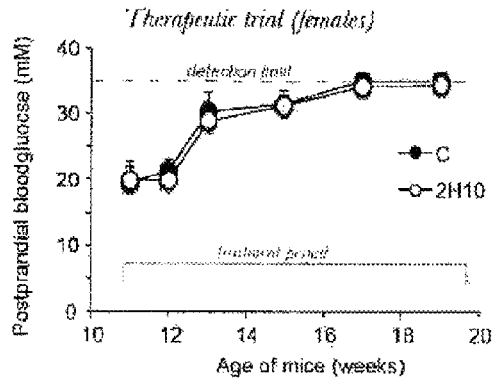

FIG. 15B shows ACR levels in db/db/BKS mice treated therapeutically or prophylactically with antibody 2H10.

These data show that db/db//BKS mice develop microalbuminuria at 6 weeks of age and macroalbuminiuria is established at 12 weeks. Neither preventative or therapeutic anti-VEGF-B antibody administration to db/db//BKS mice in these trials detectably lowered blood glucose levels.

Prophylactic Anti-VEGF-B Treatment (Using 2H10) Decreases Glomerular and Tubular Sclerosis in db/db//BKS Mice Kidneys from 6-8 weeks old db/db//BKS treated with 2H10 or isotype matched control antibody for 8 weeks as described above were collected, fixed in 4% PFA for 48 hrs, embedded and 3 µm sections were prepared and stained with PAS (Sigma) according to the manufacturer's instructions. At least 10 glomeruli per animal stained for PAS within each section were photographed with bright field microscopy (Axio Vision microscope, Carl Zeiss) at 40× magnification. The glomeruli were quantified using Axio Vision Run wizard program for glomerular PAS staining (pixel$^2$/µm$^2$).

Figure 16A:
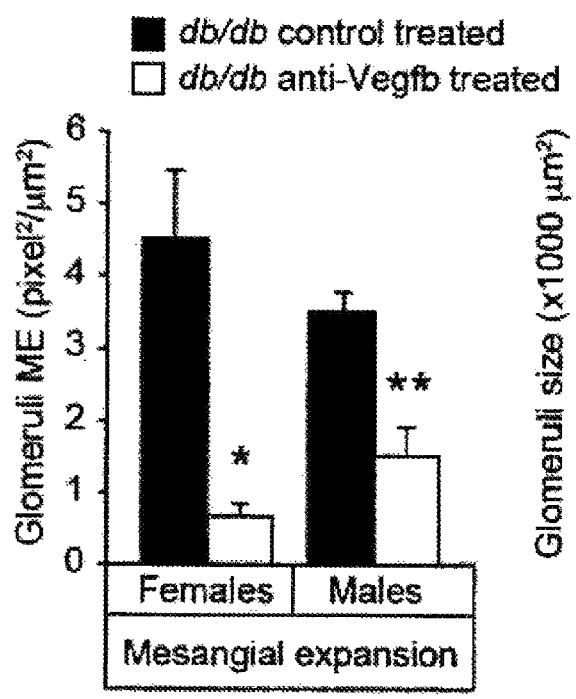
FIG. 16A is a graphical representation showing quantification of glomerular sclerosis as measured by mesangial expansion in kidney sections from db/db//BKS mice treated with anti-VEGF-B (2H10) or control antibody for 8 weeks (as indicated). Values are means±s.e.m. *P<0.05, **P<0.01 compared to control treated db/db//BKS mice.
Figure 16B:
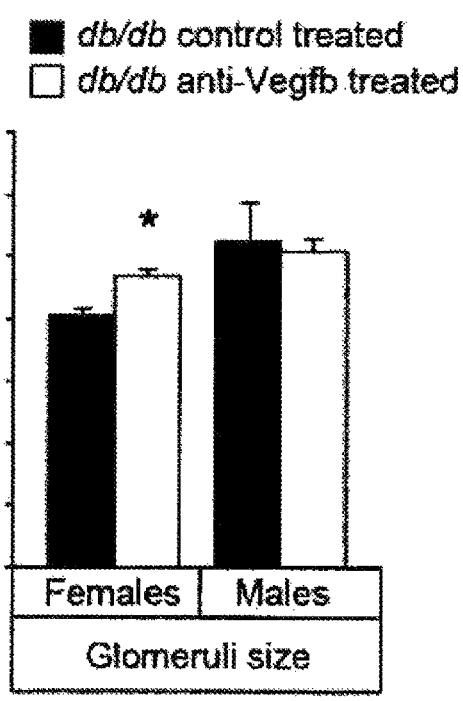
FIG. 16B is a graphical representation showing quantification of tubular sclerosis as measured by glomeruli size in kidney sections from db/db//BKS mice treated with anti-VEGF-B (2H10) or control antibody for 8 weeks (as indicated) in a prophylactic manner. Values are means±s.e.m. *P<0.05, **P<0.01 compared to control treated db/db//BKS mice.

As shown in FIGS. 16A and 16B mice treated with 2H10 show reduced levels of glomerular sclerosis and tubular sclerosis. These data demonstrate that anti-VEGF-B treatment in db/db//BKS mice reduces both glomerular sclerosis and tubular sclerosis, despite no detectable differences in blood glucose levels.

Prophylactic Anti-VEGF-B Treatment (Using 2H10) Hinders Vascular Rearrangements in db/db//BKS Mice Kidneys from 6-8 weeks old db/db//BKS treated with 2110 or isotype matched control antibody for 8 weeks as described above or age and sex-matched lean db/+ animals were collected, fixed in 4% PFA for 48 hrs, embedded and 3 µm sections were prepared and immunostained for pecam or podocin. Briefly, antigen retrieval was performed on 3 µm sections using Antigen retrieval solution Ph6 (Dako #S2367) and heated at 98° C. for 10 minutes. Sections were incubated at 4° C. for 12 hrs with primary antibodies goat anti-pecam (abcam) and rabbit anti-podocin (sigma). Appropriate fluorescently labeled secondary antibodies (Invitrogen, Alexa fluor) were applied and sections were further incubated for 1 hr at RT after which they were prepared for microscopy. At least 10 glomeruli per animal stained for pecam within each section were photographed with an Axio Vision microscope (Carl Zeiss) at 40× magnification. The glomeruli were quantified using Axio Vision Run wizard program for glomerular i) pecam (pixel$^2$/µm$^2$) and ii) podocin staining (pixel$^2$/µm$^2$).

Figure 17A:
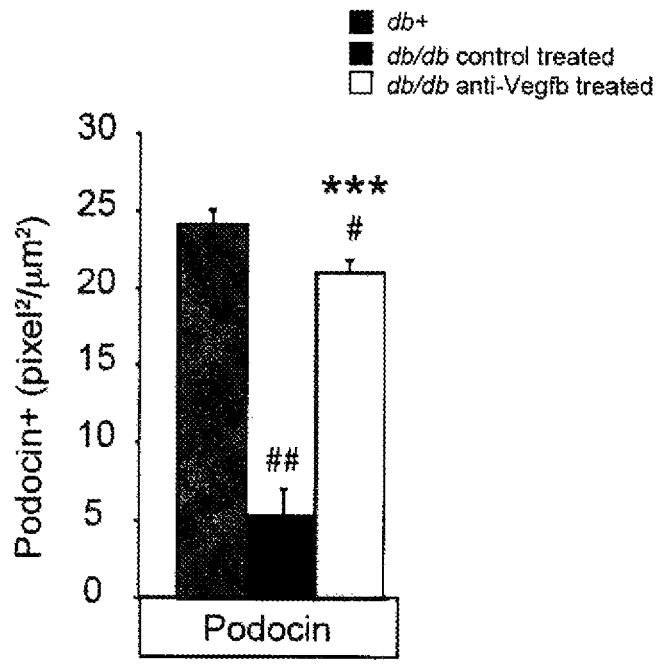
FIG. 17A is a graphical representation showing quantification of glomerular podocin staining in kidney sections from db/db//BKS mice treated with anti-VEGF-B (2H10) or control antibody in a prophylactic manner or db+ control mice. Values are means±s.e.m. ##P<0.01, compared to lean db+ controls. P<0.01, *P<0.001 compared to db/db control treated. n=3–7/group.
Figure 17B:
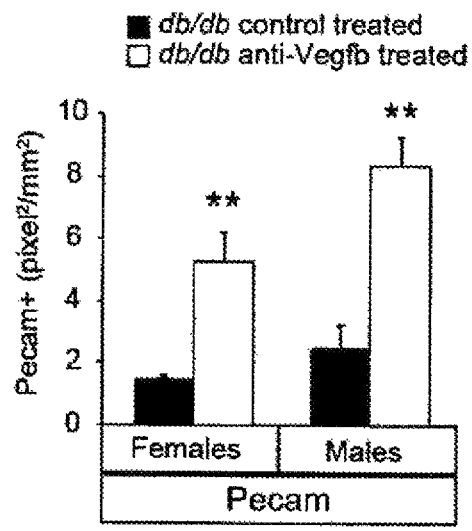
FIG. 17B is a graphical representation showing quantification of glomerular pecam staining in kidney sections from db/db//BKS mice treated with anti-VEGF-B (2H10) or control antibody in a prophylactic manner. Values are means±s.e.m. *P<0.05, **P<0.01 compared to controls.

As shown in FIG. 17A, the level of podocin staining was preserved in mice treated with 2H10. The level of pecam staining was increased in mice treated with 2H10 (FIG. 17B). These data and analysis of the stained sections indicate that blood vessel morphology in the glomeruli is improved in anti-VEGF-B treated db/d b/BKS mice and that inhibition of VEGF-B preserves vascular density and structure. These data also show inhibition of VEGF-B preserves vascular density and structure. Thus both structure and integrity of the cell types composing the glomerular filtration barrier, podocytes and endothelial cells, are preserved in db/db//BKS mice treated with anti-VEGF-B antibody.

Prophylactic Anti-VEGF-B Treatment (Using 2H10) Reserves Podocyte Structure in db/db//BKS Mice Kidneys from 6-8 weeks old db/db//BKS treated with 2H10 or isotype matched control antibody for 8 weeks as described above were collected, fixed in 4% PFA for 48 hrs, embedded and 3 µm sections were prepared and immunostained for synaptodin and/or pecam. Briefly, antigen retrieval was performed on 3 µm sections using Antigen retrieval solution Ph6 (Dako #S2367) and heated at 98° C. for 10 minutes. Sections were incubated at 4° C. for 12 hrs with primary antibodies rabbit anti-synaptopodin (Santa Cruz). Appropriate fluorescently labeled secondary antibodies (Invitrogen. Alexa fluor) were applied and sections were further incubated for 1 hr at RT after which they were prepared for microscopy. At least 10 glomeruli per animal stained for pecam within each section were photographed with an Axio Vision microscope (Carl Zeiss) at 40× magnification. The glomeruli were quantified using Axio Vision Run wizard program glomerular i) adipophilin staining (pixel$^2$/µm$^2$) and ii) synaptopodin staining (pixel$^2$/µm$^2$).

Figure 18A:
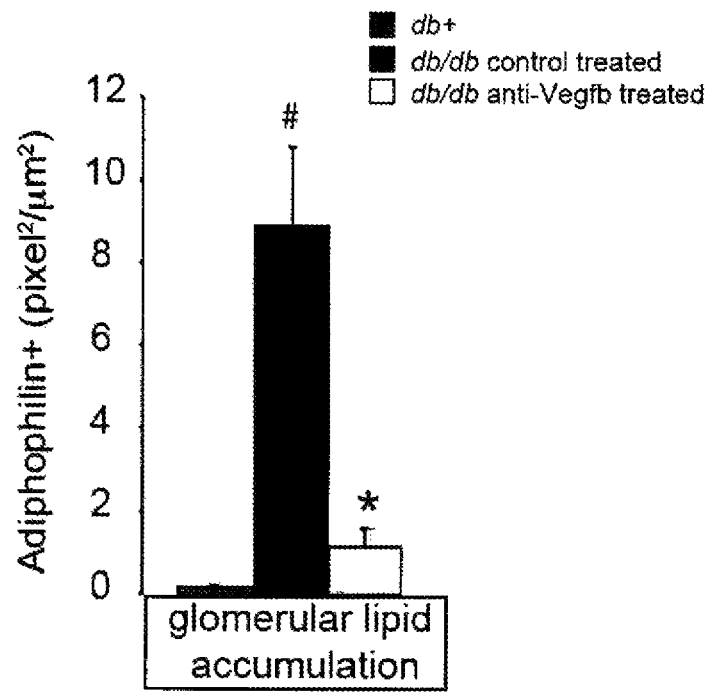
FIG. 18A is a graphical representation showing quantification of glomerular adipophilin staining in kidney sections from db/db//BKS mice treated with anti-VEGF-B (2H10) or control antibody in a prophylactic manner. Values are means±s.e.m. #P<0.05, compared to lean db+ controls. (n=3–7/group).
Figure 18B:
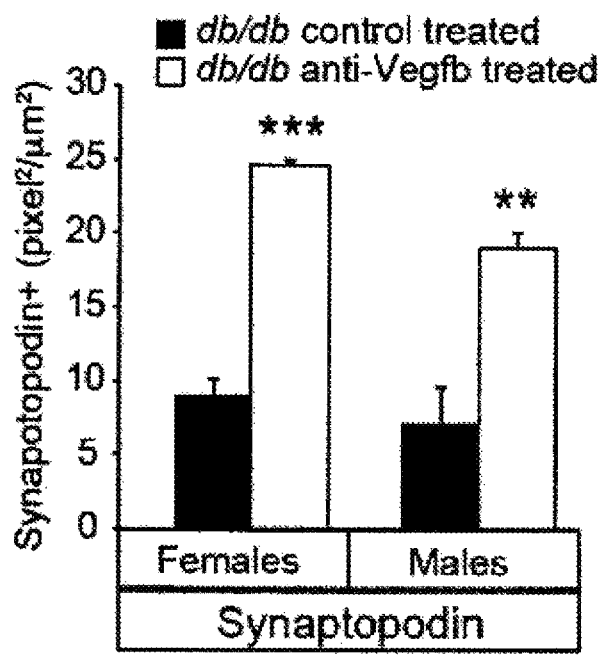
FIG. 18B is a graphical representation showing quantification of glomerular synaptopodin staining in kidney sections from db/db//BKS mice treated with anti-VEGF-B (2H10) or control antibody in a prophylactic manner. Values are means±s.e.m. *P<0.05, **P<0.01 compared to controls. (n=3–5/group.

As shown in FIG. 18A, the level of adipophilin staining was reduced in mice treated with 2H10. FIG. 18B shows that synaptopodin staining was increased in mice treated with 2H10. These data and analysis of the stained sections indicate that structure and integrity of the cell types composing the glomerular filtration barrier, podocytes and endothelial cells, are preserved in db/db//BKS mice treated with anti-VEGF-B antibody. These data also show that treatment with anti-VEGF-B antibody drastically reduced ectopic glomerular lipid accumulation and preserves podocyte expression and morphology.

Prophylactic Anti-VEGF-B Treatment (Using 2H10) Reduces Glomerular Collagen Accumulation (Extracellular Matrix Deposits) in db/db//BKS Mice Kidneys from 6-weeks old db/db//BKS treated with 2H10 or isotype matched control antibody for 8 weeks as described above were collected, fixed in 4% PFA for 48 hrs, embedded and 3 µm sections were prepared and immunostained for glomerular collagen IV. Briefly, antigen retrieval was performed on 3 µm sections using Antigen retrieval solution Ph6 (Dako #S2367) and heated at 98° C. for 10 minutes. Sections were incubated at 4° C. for 12 hrs with primary antibodies rabbit anti-synaptopodin (Santa Cruz).

Appropriate fluorescently labeled secondary antibodies (Invitrogen, Alexa fluor) were applied and sections were further incubated for 1 hr at RT after which they were prepared for microscopy. At least 10 glomeruli per animal stained for pecam within each section were photographed with an Axio Vision microscope (Carl Zeiss) at 40× magnification. The glomeruli were quantified using Axio Vision Run wizard program for glomerular collagen IV staining (pixel$^2$/μm$^2$).

Figure 19:
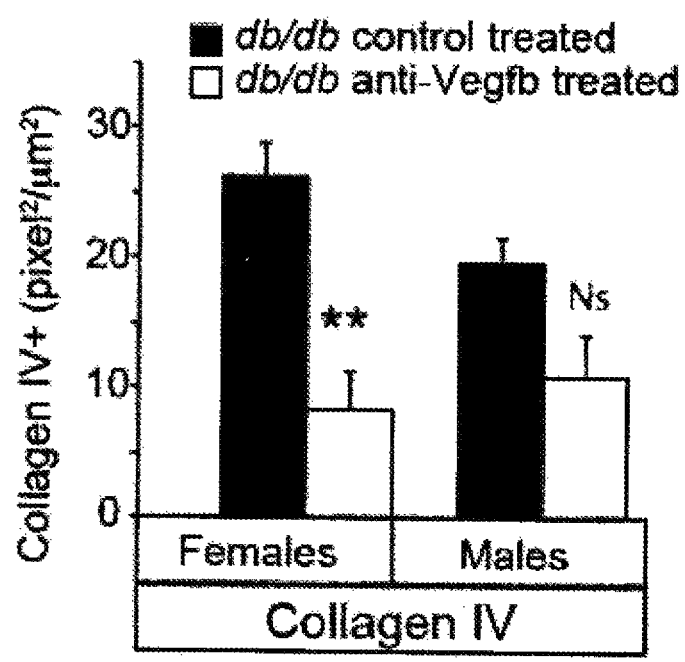
FIG. 19 is a graphical representation showing quantification of glomerular collagen IV staining in kidney sections from db/db//BKS mice treated with anti-VEGF-B (2H10) or control antibody in a prophylactic manner. Values are means±s.e.m. *P<0.05, **P<0.01 compared to controls. (n=3–5/group).

As shown in FIG. 19, the level of glomerular collagen IV staining was increased in mice treated with 2H10. These data and analysis of the stained sections indicate that antibody-mediated inhibition of VEGF-B reduces intra-glomerular pathological collagen accumulation (extracellular matrix accumulation) in db/db//BKS mice, a histological characteristic in diabetic nephropathy.

Prophylactic Anti-VEGF-B Treatment (Using 2H10) Improves the Plasma Lipid Profile in in db/db//BKS Mice Blood was collected from 6-8 weeks old female db/db/ BKS mice and age and sex-matched lean db/+ by cardiac puncture which were previously treated with 2H10 or isotype-matched control antibody for 8 weeks. The blood was centrifuged at 14000 rpm, 4° C. for 10 minutes, whereafter plasma was separated and frozen in aliquots at—80° C. Commercially available kits were used for enzymatic determination of NEFAs (Wako Chemicals, Neuss, Germany), beta-hydroxybutyrate (Stanbio Laboratories, Boerne, Tex., USA) and HDL-c and LDL-c (BioVision, Mountain View, Calif. USA).

Figure 20:
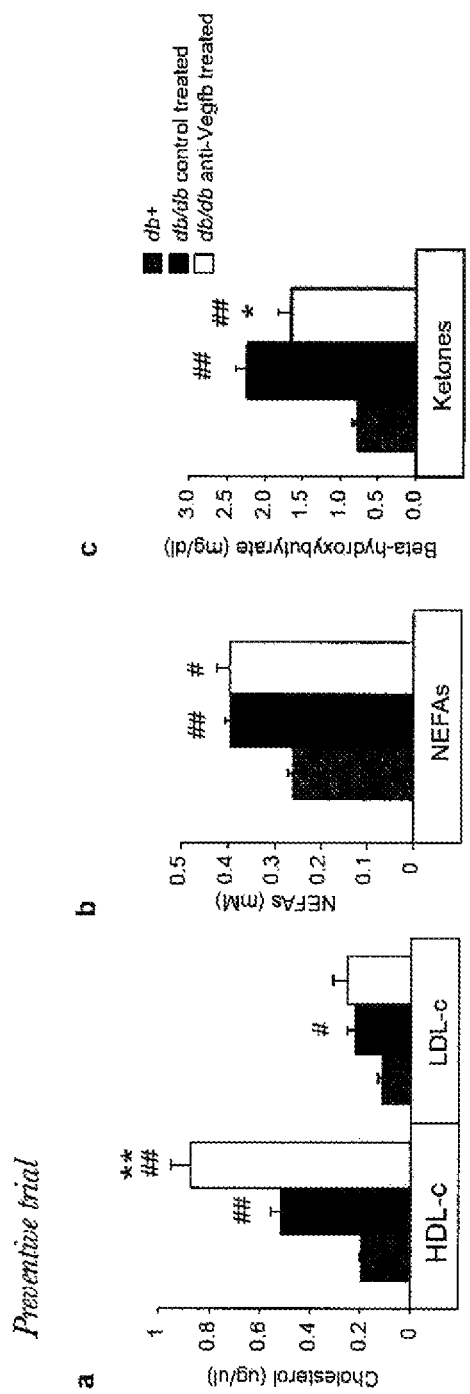
FIGS. 20A-C are a series of graphical representations showing pharmacological inhibition of VEGF-B, using 2H10 in a prophylactic manner, improves the plasma lipid profile in diabetic db/db//BKS mice. Analysis of db/db//BKS mice treated with anti-VEGF-B (2H10) or control antibody (n=–8/group) and lean db/+ animals (n=3). The graphs depict plasma levels of (FIG. 11A) HDL-c and LDL-c, (FIG. 11B) non-esterified FAs (NEFAs) and (FIG. 11B) ketones. #/*P<0.05. ##/**P<0.01, compared to lean db+ or compared to db/db control treated. Values are means±s.e.m.

As shown in FIG. 20, administration of 2H10 protected the db/db/BKS mice against elevated levels of ketones, a key hallmark of type 2 diabetes. The anti-VEGF-B treatment increased plasma HDL-c levels, also commonly known as the "good" cholesterol carrier. Reducing of VEGF-B signaling by 2H10 had no effect of plasma LDL-c levels or NEFAs.

Prophylactic Anti-VEGF-B Treatment (Using 2H10) Prevents GBM Thickening and Podocyte Abnormalities Kidneys were collected from 6-8 weeks old female db/db/ BKS were treated with 2H10 or isotype-matched control antibody for 8 weeks and used for transmission electron microscopy (TEM) analysis. The preparation of the renal biopsies for TEM was performed according to standard procedures. Tissues were fixed in the fixation solution buffer (2% glutaraldehyde, 0.5% paraformaldehyde, 0.1 M cacodylate, 0.1M sucrose, 3 mM CaCl$_2$) and washed in 0.1 M cacodylate buffer pH 7.4 prior to staining in 2% OsO$_4$ in cacodylate buffer for 1 h at room temperature. Samples were dehydrated and en bloc staining was performed in 2% uranyl acetate in absolute ethanol for 1 h at room temperature. Then samples were taken through an Epon 812/acetone series and embedded at 60° C. in pure Epon 812. Thin sections of 70 nm thicknesses were cut on a Leica EM UC6 ultratome and mounted on formvar coated copper slot grids. Post-staining was done with 2% aqueous acetate pH 3.5 and Venable and Cogglesall's lead citrate. Grids were analyzed on a FEI TECNAI electron microscopy.

Figure 21A:
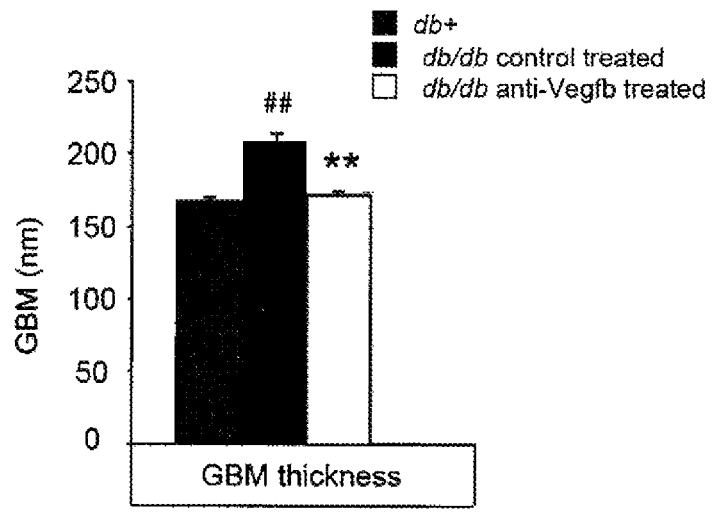
FIG. 21A is a graphical representation showing quantification of GBM thickness in kidney sections from lean db+ and db/db//BKS mice prophylactically treated with anti-VEGF-B (2H10) or control antibody. n=3–4/group. Values are means±s.e.m. ##P<0.01 compared to lean db+ controls and **P<0.01 compared to db/db control treated.
Figure 21B:
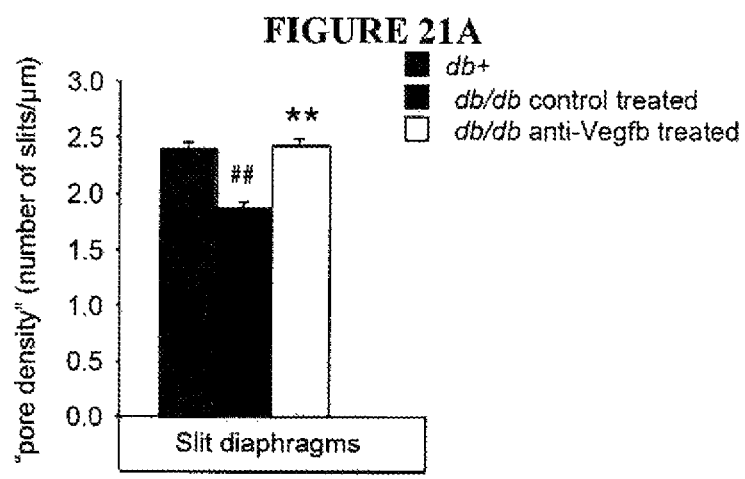
FIG. 21B is a graphical representation showing quantification of the number of slits in kidney sections from lean db+ and db/db//BKS mice prophylactically treated with anti-VEGF-B (2H10) or control antibody. n=3–4/group. Values are means±s.e.m. ##P<0.01 compared to lean db+ controls and **P<0.01 compared to db/db control treated.

High magnification TEM analysis showed that thickening of GBM, the first renal pathology in db/db mice, when treated with 21110, is decreased (FIG. 21A). Furthermore, anti-VEGF-B treatment in db/db//BKS mice preserves podocyte morphology, measured as number of slit formations (FIG. 21B).

Prophylactic Anti-VEGF-B Treatment (Using 2H10) Reduces Glomerular Lipid Accumulation in db/db//BKS Mice Blood and kidneys were collected from 6-8 weeks old db/db//BKS mice treated with 2H10 or isotype-matched control antibody for 8 weeks or lean db/+ mice. Kidneys were dissected and flash frozen on dry ice and embedded in Tissue-Tek® (Sakura) directly on the mold of the cryostat. Cryosections (12 μm) were immersed 5-min in oil red O working solution (2.5 g oil red O (Sigma-Aldrich), dissolved in 400 ml 99% isopropanol, further diluted 6:10 in H$_2$O, filtered through a 22 μm filter (Corning)) and rinsed 10 min under running tap water. Thereafter the sections were submerged for 3 s in hematoxylin solution and rinsed under tap water before they were mounted. Stained sections were examined with bright field microscopy. At least 10 glomeruli per animal stained for ORO and hematoxylin within each section were photographed with an Axio Vision microscope (Carl Zeiss) at 40× magnification. The glomeruli were quantified using Axio Vision Run wizard program for glomerular ORO staining (pixel$^2$/μm$^2$).

Figure 22:
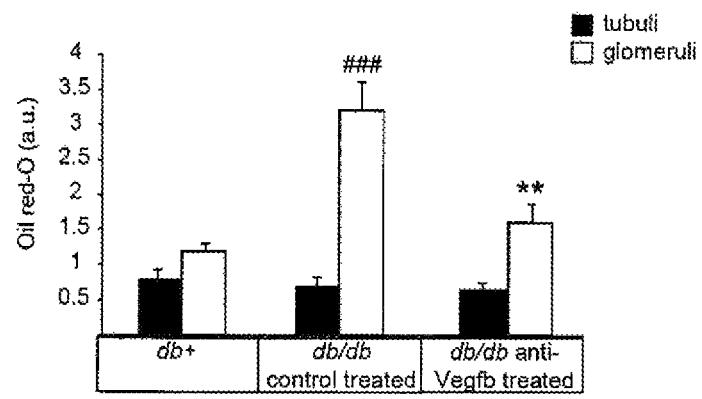
FIG. 22 is a graphical representation showing quantification of the oil red O staining both in the glomeruli and in the tubular compartment in kidney sections from db/db//BKS mice treated with anti-VEGF-B (2H10) or control antibody and lean db/+ animals. n=3–7/group. Values are means±s.e.m. ###P<0.001, compared to lean db+ controls. **P<0.01 compared to db/db control treated.

A specific increase in lipid accumulation was detected in the glomeruli of diabetic animals in comparison to lean non-diabetic animals (FIG. 22). Inhibition of VEGF-B in db/db//BKS drastically reduced this ectopic glomerular lipid accumulation. The lipid droplets were reduced both in number and size. The analysis indicated that the droplets predominantly accumulated in endothelial cells, and podocytes.

Therapeutic Anti-VEGF-B Treatment (Using 2H10) Decreases Glomerular and Tubular Sclerosis in Severe Diabetic db/db//BKS Mice Kidneys from 12-weeks old male and female db/db/BKS treated with 2H10 or isotype-matched control antibody for 8 weeks, were collected, fixed in 4% PFA for 48 hrs, embedded and 3 μm sections were prepared and stained with PAS (Sigma) according to the manufacturer's instructions. At least 10 glomeruli per animal stained for PAS within each section were photographed with bright field microscopy (Axio Vision microscope, Carl Zeiss) at 40× magnification. The glomeruli were quantified using Axio Vision Run wizard program for glomerular PAS staining (pixel$^2$/μm$^2$).

Results shown in FIGS. 23A and 23B and from analysis of the stained sections indicate that therapeutic inhibition of VEGF-B in d/db/BKS mice reduces glomerular and tubular sclerosis. The effect is only detected in female animals, most likely because the disease is more aggressive in male db/db//BKS mice (a commonly observed effect).

Therapeutic Anti-VEGF-B Treatment (Using 2H10) Reduces Renal Lipid Accumulation in Severe Diabetic db/db//BKS Mice Kidneys from 12-weeks old male and female db/db//BKS treated with 2H10 or isotype-matched control antibody for 8 weeks, were collected, and flash frozen on dry ice and embedded in Tissue-Tek® (Sakura) directly on the mold of the cryostat. Cryosections (12 μm) were immersed 5-15 min in ORO working solution (2.5 g ORO (Sigma-Aldrich), dissolved in 400 ml 99% isopropanol, further diluted 6:10 in H2O, filtered through a 22 μm filter (Corning)) and rinsed 10 min under running tap water before they were mounted. Stained sections were examined with bright field microscopy (Axio Vision microscope, Carl Zeiss) at 20× magnification and a minimum of 10 frames per section was captured. For quantification of lipid droplets, the amount of red pixels in each frame was quantified using Axio Vision Run wizard program for total ORO staining (pixel, a.u).

As shown in FIG. 24, the amount of ORO staining was reduced in female db/db//BKS mice receiving antibody treatment. These data and analysis of the stained sections indicate that both numbers and size of lipid droplets were reduced in female db/db//BKS mice treated with anti-VEGF-B antibody. Anti-VEGF-B antibody treatment did not reduce renal lipid accumulation in male db/db//BKS mice, most likely as a result of the more aggressive development of the disease in male animals.

Therapeutic Anti-VEGF-B Treatment (Using 2H10) Prevents Glomerular Rearrangements in Severe Diabetic db/db//BKS Mice Kidneys from 12-weeks old female db/db/BKS treated with 2H10 or isotype-matched control antibody for 8 weeks, were collected, fixed in 4% PFA for 48 hrs. embedded and 3 μm sections were prepared and immunostained for synaptodin or pecam. Briefly, antigen retrieval was performed on 3 μm sections using Antigen retrieval solution Ph6 (Dako #S2367) and heated at 98° C. for 10 minutes. Sections were incubated at 4° C. for 12 his with primary antibodies rabbit anti-synaptopodin (Santa Cruz). Appropriate fluorescently labeled secondary antibodies (Invitrogen, Alexa fluor) were applied and sections were further incubated for 1 hr at RT after which they were prepared for microscopy. At least 10 glomeruli per animal stained for pecam within each section were photographed with an Axio Vision microscope (Carl Zeiss) at 40× magnification. The glomeruli were quantified using Axio Vision Run wizard program for glomerular synaptopodin or pecam staining (pixel$^2$/μm$^2$).

Figure 25A:
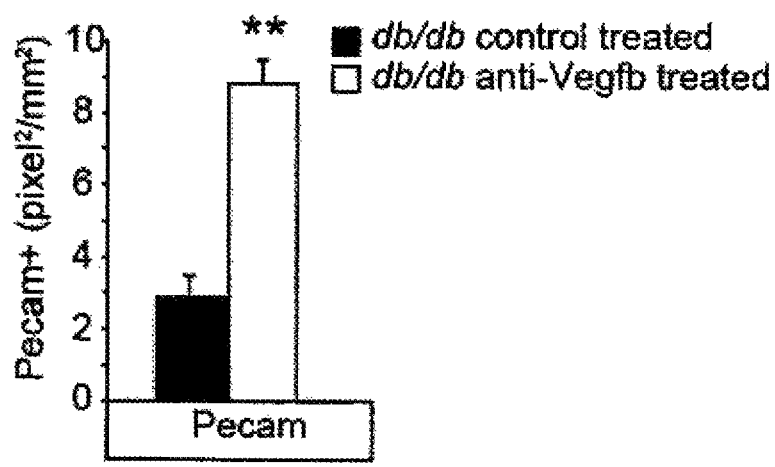
FIG. 25A is a graphical representation showing quantification of glomerular pecam staining in kidney sections from db/db//BKS mice treated with anti-VEGF-B (2H10) or control antibody in a therapeutic manner. Values are means±s.e.m. *P<0.05, **P<0.01 compared to controls.
Figure 25B:
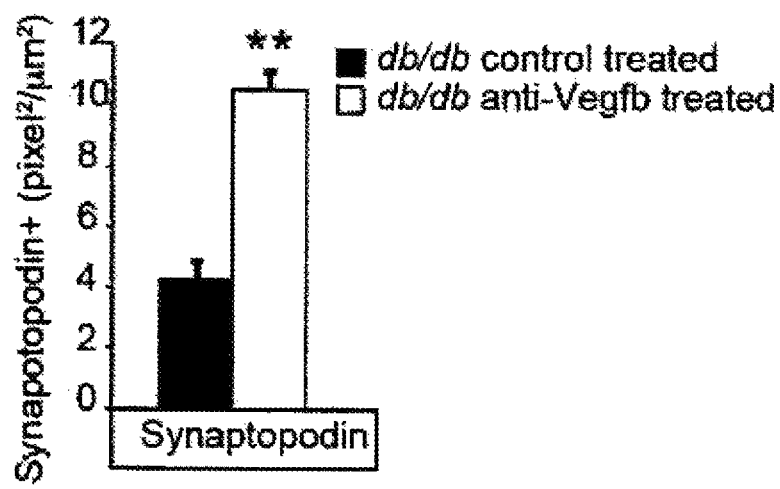
FIG. 25B is a graphical representation showing quantification of glomerular synaptopodin staining in kidney sections from db/db//BKS mice treated with anti-VEGF-B (2H10) or control antibody in a therapeutic manner. Values are means±s.e.m. *P<0.05, **P<0.01 compared to controls. (n=4–5/group).

FIGS. 25A and 25B show increased levels of pecam and synaptopodin levels in glomeruli of mice treated therapeutically with anti-VEGF antibody. These data and analysis of the stained sections indicate that glomeruli morphology is improved in db/db//BKS treated with anti-VEGF-B antibody. Expression and structure of podcoytes and endothelial cells, i.e cell types that are crucial for the glomerular filtration process, are preserved in treated db/db//BKS mice. Thus, these data also indicate that therapeutic treatment with an anti-VEGF antibody also prevents vascular and podocyte loss db/db//BKS mice.

Therapeutic Anti-VEGF-B Treatment (Using 2H10) Reduces Glomerular Collagen Accumulation and Arteriolar Hyalinosis in Severe Diabetic db/db//BKS Mice Kidneys from 12-weeks old female db/db//BKS treated with 2H10 or isotype-matched control antibody for 8 weeks, were collected, fixed in 4% PFA for 48 hrs, embedded and 3 μm sections were prepared and immunostained for collagen IV, pecam, and/or α-SMA. Briefly, antigen retrieval was performed on 3 μm sections using Antigen retrieval solution Ph6 (Dako #S2367) and heated at 98° C. for 10 minutes. Sections were incubated at 4° C. for 12 hrs with primary antibodies rabbit anti-synaptopodin (Santa Cruz). Appropriate fluorescently labeled secondary antibodies (Invitrogen, Alexa fluor) were applied and sections were further incubated for 1 hr at RT after which they were prepared for microscopy. At least 10 glomeruli per animal stained for pecam within each section were photographed with an Axio Vision microscope (Carl Zeiss) at 40× magnification. The glomeruli were quantified using Axio Vision Run wizard program for glomerular collagen IV, pecam, and/or α-SMA staining (pixel$^2$/μm$^2$).

FIGS. 26A-C show reduced levels of collagen IV, α-SMA and arteriolar thickness in db/db/BKS mice treated with 2H10. These data and analysis of the stained sections show pathological intra glomerular collagen deposition (extracellular matrix deposition) and arteriolar hyalinosis are reduced in db/db//BKS mice treated with anti-VEGF-B antibody.

Therapeutic Anti-VEGF-B Treatment (Using 2H10) Prevents the Development of Macroalbuminuria in Diabetic db/db//BKS Mice with Established Microalbuminuria db/db/BKS mice were injected ip, twice weekly, starting at 6-8 weeks of age, and continued for 8 weeks with 400 μg of either 2H10 or isotype-matched control antibody. For detection of ACR 20-μl to 200-μl volume of urine was collected from each mouse. Urinary albumin was detected using Albuwell M kit, and urinary creatinine was measured using the Creatinine Companion murine ELISA kit (Exocell, Philadelphia, Pa.). Systolic and diastolic blood pressure was measured by a tail-cuff method using the CODA setup (Kent Scientific). All animals were habituated to the blood pressure measurement device for 2 weeks. Animals underwent 1-2 cycle of 20 measurements reordered per day for a minimum of 3 days. For mouse renal functional studies, individual mice were housed in metabolic cages. Bodyweight and urine volume in 24 h were monitored for 2 consecutive days. Urine samples of the latter 24 h were used to measure urine creatinine. After housing in metabolic cages the animals were sacrificed by isofluorane anaesthetics and total blood was removed by cardiac puncture, and used to measure plasma creatine. Kidneys were dissected and weighed on a microscale. Creatinine clearance was calculated by (urine [Cr]× urine volume)/(plasma ([Cr]×24 h).

Figure 27A:
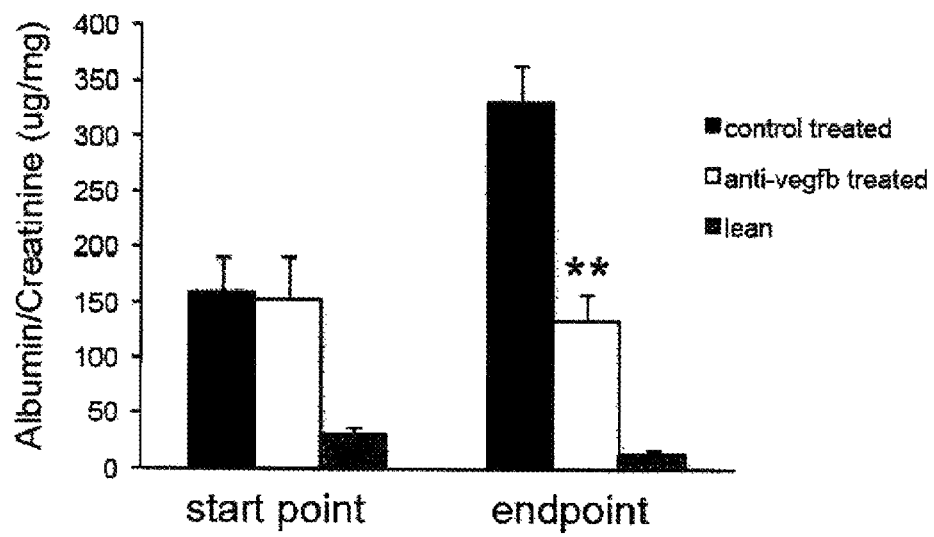
FIG. 27A is a graphical representation showing urine ACR measured by ELISA in db/db//BKS mice treated with anti-VEGF-B (2H10) or control antibody for 8 weeks or lean animals (n=3–7 group). Values are means±s.e.m. Startpoint and endpoint shows ACR before and after the treatment period, respectively. *P<0.05, **P<0.01 compared to control treated animals.
Figure 27B:
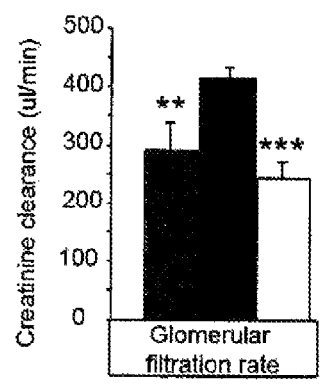
FIG. 27B is a graphical representation showing glomerular filtration rate measured as creatinine clearance in db/db//BKS mice treated with anti-VEGF-B (2H10) or control antibody for 8 weeks or lean animals (n=3–7 group). Values are means±s.e.m. *P<0.05, P<0.01, *P<0.001 compared to db/db control treated animals.
Figure 27C:
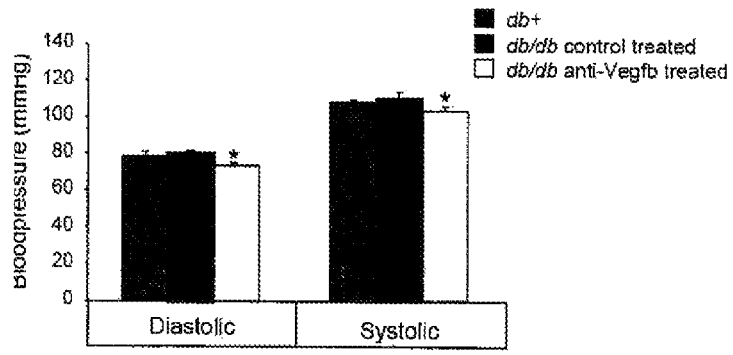
FIG. 27C is a graphical representation showing tail-cuff blood pressure (systolic and diastolic blood pressure) in db/db//BKS mice treated with anti-VEGF-B (2H10) or control antibody for 8 weeks or lean animals (n=3–7 group). Values are means±s.e.m. *P<0.05, P<0.01. *P<0.001 compared to db/db control treated animals.
Figure 27D:
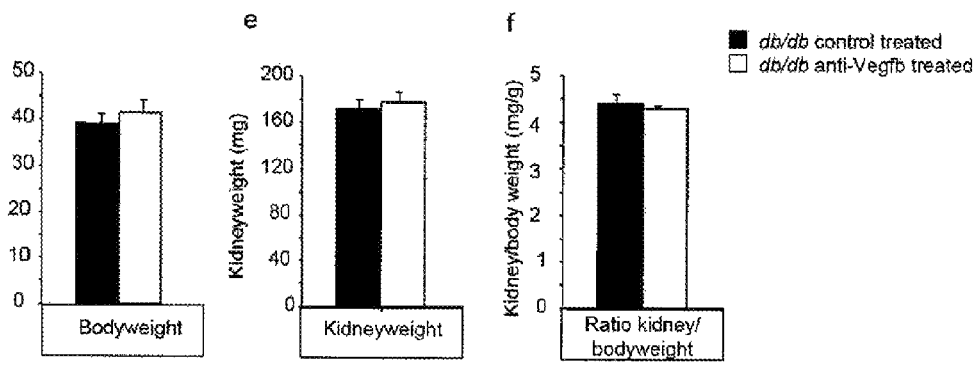
FIG. 27D is a series of three graphical representations showing bodyweight (left hand graph), kidney weight (center graph) and ratio of bodyweight to kidney weight (right hand graph) in db/db//BKS mice treated with anti-VEGF-B (2H10) or control antibody for 8 weeks or lean animals (n=4 group). Values are means±s.e.m. *P<0.05, P<0.01. *P<0.001 compared to db/db control treated animals.

FIG. 27A shows treatment of db/db/BKS mice with 2H10 prevents progression of microalbuminuria to macroalbuminuria, in particular, the ACR did not significantly change over the course of the study in treated mice. FIG. 27B shows glomerular filtration rate (measured as creatinine clearance) was also reduced in db/db//BKS mice treated with 2H10 FIG. 27C shows that the development of hypertension was prevented by inhibition of VEGF-B. FIG. 27D shows that reducing the expression of VEGF-B had no effect on body or kidney weight. These data indicate that db/db mice treated with anti-VEGF-B antibody have an improved kidney function with better filtration capacity as measured by reduced concentration of urinary albumin, urinary albumin/creatinine ratio and creatinine clearance.

Therapeutic Anti-VEGF-B Treatment (Using 2H10) in HFD Fed Mice has a Minor Effect on Blood Glucose Levels Mice were fed 60% HFD (Research Diets, USA) for HFD for 30 weeks, starting at age 5 weeks. Antibody treatment commenced at week 11 and mice were treated with 2H10 or isotype-matched control antibody for 20 weeks. Postprandial BG levels of mice were recorded at the end of the trial, after removal of food for 2 h. Glucose measurements were performed on blood drawn from the tail vein using a Bayer Contour Glucose meter.

Figure 28:
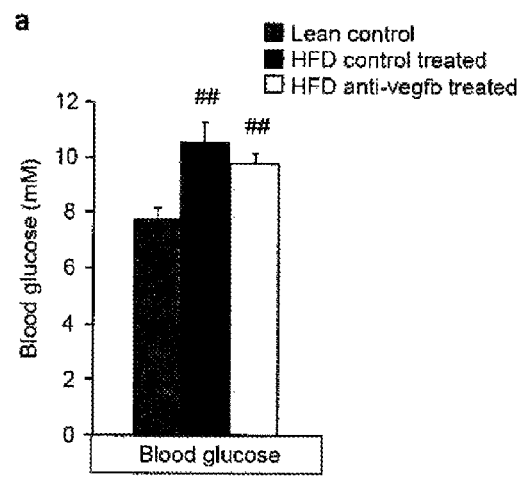
FIG. 28 is a graphical representation showing blood glucose levels in HFD fed mice treated therapeutically with anti-VEGF-B (2H10) or control antibody, and lean control animals. Postprandial blood glucose levels at the end of the treatment period. Values are means±s.e.m. ##P<0.01 compared to lean control animals.

FIG. 28 shows that HFD increases blood glucose levels, however anti-VEGF-B treatment does not prevent the development of hyperglycemia.

Therapeutic-VEGF-B Treatment (Using 21110) in HFD Fed Mice Improves Renal Function without Decreasing Blood Glucose Levels Mice were fed 60% HFD (Research Diets, USA) for HFD for 30 weeks, starting at age 5 weeks. The study also included lean wild type control animals. Antibody treatment commenced at week 11 and mice were treated with 2H10 or isotype-matched control antibody for 20 weeks. For detection of albumin and ACR 20-μl to 200-μl volume of urine was collected from each mouse at the endpoint of the trial. Urinary albumin was detected using Albuwell M kit, and urinary creatinine was measured using the Creatinine Companion murine ELISA kit (Exocell, Philadelphia, Pa.).

Figures 29A, 29B:
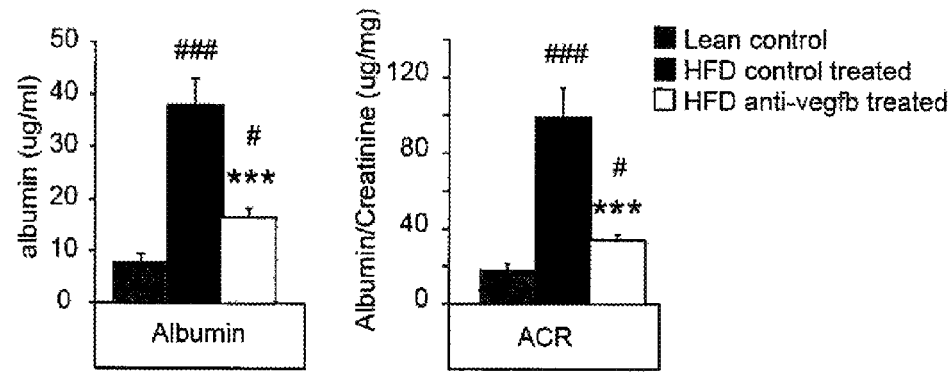
FIG. 29A is a graphical representation showing urine albumin levels in HFD fed mice treated therapeutically with anti-VEGF-B (2H10) or control antibody, and lean control animals (n=5–10/group). ACR, albumin/creatinine ratio, Values are means±s.e.m. #P<0.05. ###P<0.001 compared to lean control animals. ***P<0.001 compared to HFD fed control treated.
FIG. 29B is a graphical representation showing urine albumin/creatinine ratio as measured by ELISA in HFD fed mice treated therapeutically with anti-VEGF-B (2H10) or control antibody, and lean control animals (n=5–10/group). Values are means±s.e.m. #P<0.05, ###P<0.001 compared to lean control animals. ***P<0.001 compared to HFD fed control treated.

While anti-VEGF-B treatment in HFD fed mice did not lower blood glucose levels, the treatment had a significant impact on diabetic renal physiology (FIG. 29). The kidney filtration capacity was improved as measured by reduced albumin excretion (FIG. 29A). ACR (FIG. 29B) and GFR. Anti-VEGF-B treatment in HFD fed mice had no effect on body or kidney weight, in comparison to control treated mice.

Therapeutic Anti-VEGF-B Treatment (Using 2H10) in HFD Fed Mice Improves Plasma Lipid Profile Mice were fed 60% HFD (Research Diets, USA) for HFD for 30 weeks, starting at age 5 weeks. The study additionally included lean wild type control animals. Antibody treatment commenced at week 11 and mice were treated with 2H10 or isotype-matched control antibody for 20 weeks. Animals were sacrificed by isofluorane anaesthetics and total blood was removed by cardiac puncture. The blood was centrifuged at 14000 rpm, 4° C. for 10 minutes, whereafter plasma was separated and frozen in aliquots at −80° C. Commercially available kits were used for enzymatic determination of NEFAs (Wako Chemicals, Neuss, Germany), beta-hydroxybutyrate (Stanbio Laboratories. Boerne, Tex., USA) and triglycerides (Sigma-Aldrich).

Figure 30A:
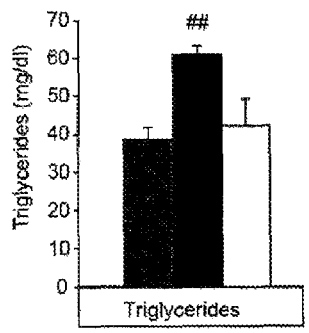
FIG. 30A is a graphical representation showing plasma levels of triglycerides in HFD fed mice treated therapeutically with anti-VEGF-B (2H10) or control antibody and lean wt animals (n=5–10/group). #P<0.05. ##P<0.01, compared to lean control animals. Values are means±s.e.m. *P<0.05, compared to HFD fed control treated.
Figure 30B:
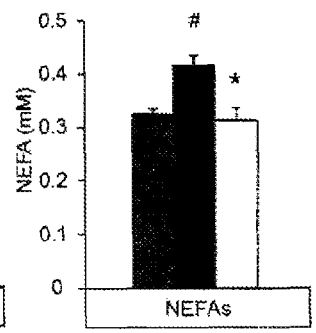
FIG. 30B is a graphical representation showing plasma levels of non-esterified FAs (NEFAs) in HFD fed mice treated therapeutically with anti-VEGF-B (2H10) or control antibody and lean wt animals (n=5–10/group). #P<0.05, ##P<0.01, compared to lean control animals. Values are means±s.e.m. *P<0.05, compared to HFD fed control treated.
Figure 30C:
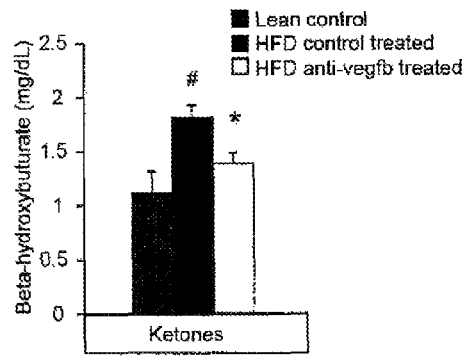
FIG. 30C is a graphical representation showing plasma levels of ketones in HFD fed mice treated therapeutically with anti-VEGF-B (2H10) or control antibody and lean wt animals (n=5–10/group). #P<0.05, ##P<0.01, compared to lean control animals. Values are means±s.e.m. *P<0.05, compared to HFD fed control treated.

FIG. 30 shows that administration of 2H10 in HFD fed mice protected against elevated levels of lipid species associated with T2D. For example, anti-VEGF-B antibody treatment decreased plasma levels of triglycerides (FIG. 30A), NEFAs (FIG. 30B) and ketones (FIG. 30C).

Therapeutic Anti-VEGF-B Treatment (Using 2H10) in HFD Fed Mice Prevents Glomerular Mesangial Expansion and Sclerosis Mice were fed 60% HFD (Research Diets, USA) for HFD for 30 weeks, starting at age 5 weeks. The study also included lean wild type control animals. Antibody treatment commenced at week 11 and mice were treated with 2H10 or isotype-matched control antibody for 20 weeks. Animals were sacrificed by isofluorane anaesthetics and total blood was removed by cardiac puncture. Kidneys were dissected, post-fixated in 4% PFA for 48 h and subsequently processed for paraffin imbedding using standard procedures. After embedding, 3-μm sections were prepared and stained with PAS (Sigma) according to the manufacturer. At least 10 glomeruli per animal stained for PAS within each section were photographed with bright field microscopy (Axio Vision microscope, Carl Zeiss) at 40× magnification. The glomeruli were quantified using Axio Vision Run wizard program for glomerular PAS staining (pixel$^2$/μm$^2$).

Figure 31A:
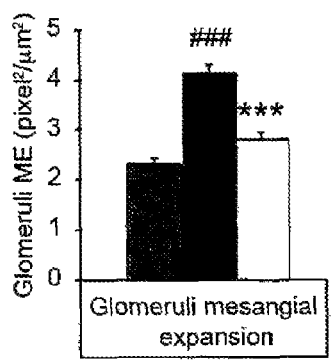
FIG. 31A is a graphical representation showing quantification of glomerular mesangial expansion in HFD fed mice treated therapeutically with anti-VEGF-B (2H10) or control antibody and lean wt animals. n=5-10/group. Values are means±s.e.m. #P<0.05, ###P<0.001 compared to lean control animals. ***P<0.001 compared to HFD fed control treated.
Figure 31B:
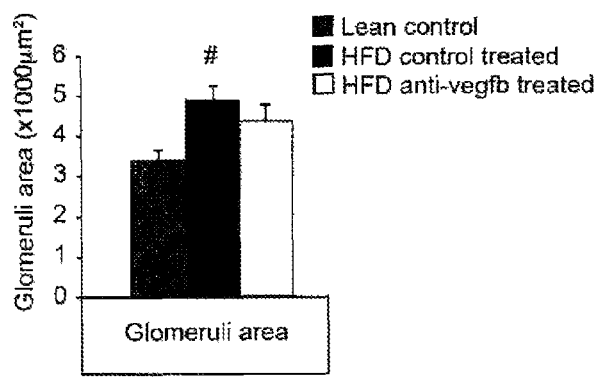
FIG. 31B is a graphical representation showing quantification of glomeruli area in HFD fed mice treated therapeutically with anti-VEGF-B (2H10) or control antibody and lean wt animals. n=5-10/group. Values are means±s.e.m. #P<0.05. ###P<0.001 compared to lean control animals. ***P<0.001 compared to HFD fed control treated.

Data presented in FIG. 31 and analysis of stained sections shows that administration of 2H10 in HFD fed mice protected against glomerular mesangial expansion (FIG. 31A) and glomerular hypertrophy (FIG. 31B).

Therapeutic Anti-VEGF-B Treatment (Using 2H10) in HFD Fed Mice Prevents Glomerular Lipid Accumulation Mice were fed 60% HFD (Research Diets, USA) for HFD for 30 weeks, starting at age 5 weeks. The study also included lean wild type control animals. Antibody treatment commenced at week 11 and mice were treated with 2H10 or isotype-matched control antibody for 20 weeks. Animals were sacrificed by isofluorane anaesthetics and total blood was removed by cardiac puncture. Kidneys were dissected and flash frozen on dry ice and embedded in Tissue-Tek® (Sakura) directly on the mold of the cryostat. Cryosections (12 μm) were immersed 5-15 min in oil red O working solution (2.5 g oil red O (Sigma-Aldrich), dissolved in 400 ml 99% isopropanol, further diluted 6:10 in H$_2$O, filtered through a 22 μm filter (Corning)) and rinsed 10 min under running tap water. Thereafter the sections were submerged for 3 s in hematoxylin solution and rinsed under tap water before they were mounted. Stained sections were examined with bright field microscopy. At least 10 glomeruli per animal stained for ORO and hematoxylin within each section were photographed with an Axio Vision microscope (Carl Zeiss) at 40× magnification. The glomeruli were quantified using Axio Vision Run wizard program for glomerular ORO staining (pixel$^2$/μm$^2$).

Figure 32:
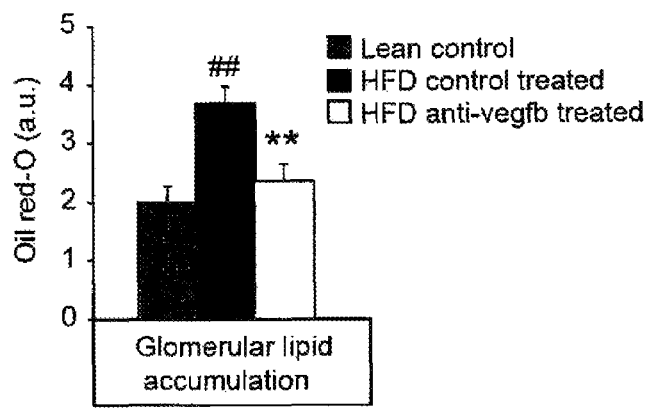
FIG. 32 is a graphical representation showing quantification of oil red O staining of glomeruli of kidney sections from HFD fed mice treated therapeutically with anti-VEGF-B (2H10) or control antibody, and lean control animals. ##P<0.01 compared to lean control and **P<0.01 compared to HD control treated animals.

Data presented in FIG. 32 and analysis of stained sections shows that administration of 2H10 in HFD fed mice protects against ectopic renal lipid accumulation. Lipid droplets are reduced both in number and size.

Therapeutic Anti-VEGF-B Treatment (with 2H10) in HFD Fed Mice Prevents Glomerular Lipid Accumulation and Preserves Podocyte Integrity Mice were fed 60%. HFD (Research Diets, USA) for HFD for 30 weeks, starting at age 5 weeks. The study also included lean wild type control animals. Antibody treatment commenced at week 11 and mice were treated with 2H10 or isotype-matched control antibody for 20 weeks. Animals were sacrificed with isofluorane anaesthetics and total blood was removed by cardiac puncture. Kidneys were dissected, post-fixated in 4% PFA for 48 h and subsequently processed for paraffin imbedding using standard procedures, After embedding, 3-μm sections were prepared and thereafter immunostained for collagen IV, pecam and/or α-SMA Briefly, antigen retrieval was performed on 3 μm sections using Antigen retrieval solution Ph6 (Dako #S2367) and heated at 98° C. for 10 minutes. Sections were incubated at 4° C. for 12 h with primary antibodies rabbit anti-collagen IV (abeam), goat anti-pecam (Abcam) or α-SMA (Sigma). Appropriate fluorescently labeled secondary antibodies (Invitrogen, Alexa fluor) were applied and sections were further incubated for 1 hr at RT after which they were prepared for microscopy. At least 10 glomeruli per animal stained for collagen IV, pecam or α-SMA within each section were photographed with an Axio Vision microscope (Carl Zeiss) at 40× magnification. The glomeruli were quantified using Axio Vision Run wizard program for glomerular i) collagen IV staining (pixel$^2$/μm$^2$) and ii) thickness of glomerular arterioles (μm$^2$).

Figure 33A:
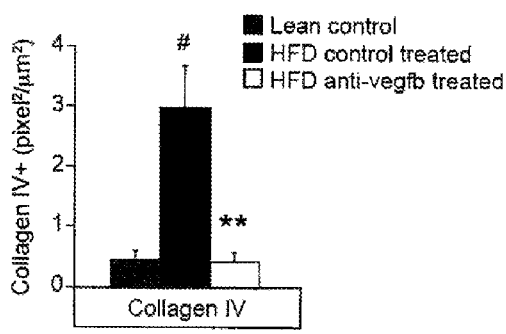
FIG. 33A is a graphical representation showing quantification of collagen IV staining of kidney sections from HFD fed mice treated therapeutically with anti-VEGF-B (2H10) or control antibody, and lean control animals. #P<0.05 compared to lean control animals. *P<0.05 compared to HFD fed control treated.
Figure 33B:
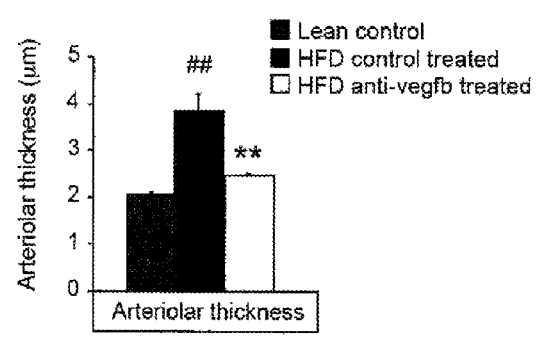
FIG. 33B is a graphical representation showing quantification of arteriolar thickness in kidney sections from HFD fed mice treated therapeutically with anti-VEGF-B (2H10) or control antibody, and lean control animals. #P<0.05 compared to lean control animals. *P<0.05 compared to HFD fed control treated.

Data presented in FIG. 33 and analysis of stained sections shows that administration of 2H10 in HFD fed mice protects against histological diabetic nephropathy-associated pathologies, such as increased glomerular ECM accumulation (FIG. 33A) and arteriolar hyalinosis (FIG. 33B).

Therapeutic Anti-VEGF-B Treatment (with 2H10) in STZ Injected Animals has No Effect on Blood Glucose Levels For induction of type I diabetes, a streptozotozin (STZ) model was employed. Experiments were performed with male B1/6 mice from Charles River. Mice were starved for 4 hrs prior to STZ injections, and received 50 mg/kg body weight streptozotocin (Sigma-Aldrich) in 50 mM sodium citrate (pH 4.5) or sodium citrate buffer intraperitoneally on day 1, 2, 3, 4 and 5. BG levels of mice were recorded before and 1 week after STZ administration. Animals with blood glucose levels above 12 mmol/l were regarded as hyperglycemic. Animals were divided randomly in two groups and treated with 2H10 or isotype-matched control antibody twice weekly. Postprandial BG levels of mice treated with anti-VEGF-B (2H10) or control antibody, and lean control animals were recorded biweekly after removal of food for 2 h. Glucose measurements were performed on blood drawn from the tail vein using a Bayer Contour Glucose meter.

Figure 34A:
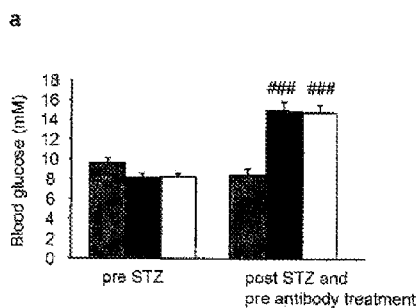
FIG. 34A is a graphical representation showing blood glucose levels before and after streptozotocin (STL) injections. Lean control animals were not injected with STZ. After STZ injections, animals with established hyperglycemia (blood glucose levels over 12 mM) were dosed with anti-VEGF-B (2H10) or control antibody. (n=3-7/group). Values are means±s.e.m. ##P<0.01, ###P<0.001 compared to lean control animals. STZ, streptozotocin
Figure 34B:
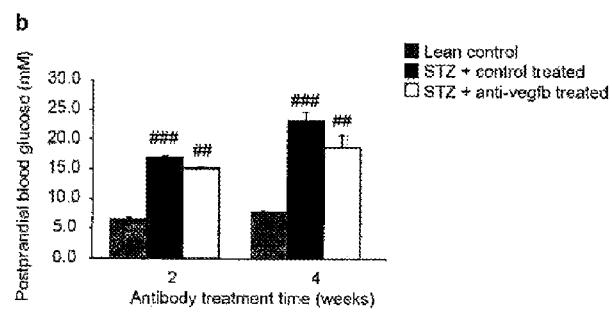
FIG. 34B is a graphical representation showing blood glucose levels in mice treated with ST (other than lean control animals) and treated anti-VEGF-B antibody (2H10) or control antibody, and lean control animals. Lean control animals were not injected with STZ. (n=3-7/group). Values are means±s.e.m. ##P<0.01, ###P<0.001 compared to lean control animals. STZ, streptozotocin

As shown in FIG. 34A, STZ injection in male mice induces hyperglycemia. However, anti-VEGF-B treatment after STZ injections has no major effect on blood glucose levels (FIG. 34B).

Therapeutic Anti-VEGF-B Treatment in STZ-Injected Animals, Using 2H10, Improves Renal Function For induction of type I diabetes, the streptozotozin (STZ) model was employed. Experiments were performed with male Bl/6 mice from Scanbur. Mice were starved for 4 hrs prior to STZ injections, and received 50 mg/kg body weight STZ (Sigma-Aldrich) in 50 mM sodium citrate buffer (pH 4.5) intraperitoneally on day 1-5. BG levels of mice were recorded before and 1 week after STZ administration. Animals with glucose levels above 12 mmol/l were regarded as hyperglycemic. Animals were divided randomly in two groups and treated with 2H10 or isotype-matched control antibody twice weekly as above. For detection of albumin and ACR 20-μl to 200-μl volume of urine was collected from each mouse at the endpoint of the trial (ongoing experiment, only 1 wk of treatment reported. Urinary albumin was detected using Albuwell M kit, and urinary creatinine was measured using the Creatinine Companion murine ELISA kit (Exocell. Philadelphia, Pa.).

Figure 35A:
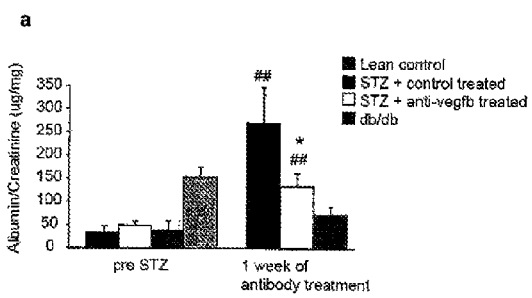
FIG. 35A is a graphical representation showing albumin/creatinine ratio (ACR) in mice pre-STL administration and after STZ-administration with dosing of anti-VEGF-B (2H10) or control antibody for 1 week. Lean control animals and db/db animals were not injected with STZ. Urine albumin/creatinine ratio was measured by ELISA (n=3-6/group). ACR, albumin/creatinine ratio, Values are means±s.e.m. ##P<0.01 compared to pre STZ animals. *P<0.05 compared to STZ control treated animals. STZ, streptozocin
Figure 35B:
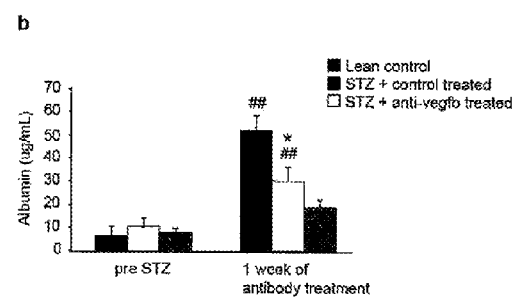
FIG. 35B is a graphical representation showing albumin levels in mice pre-STZ administration and after STZ-administration with dosing of anti-VEGF-B (2H10) or control antibody for 1 week. Lean control animals were not injected with STZ. Urine albumin levels were measured by ELISA (n=3-6/group). Values are means±s.e.m. ##P<0.01 compared to pre STZ animals. *P<0.05 compared to STZ control treated animals. STZ, streptozotocin

Despite minor effects on blood glucose levels in mice dosed with anti-VEGF-B antibody 2H10 after STZ injections, the renal function of diabetic mice was significantly improved by antibody treatment. The kidney filtration capacity was improved as measured by reduced albumin excretion (FIG. 35A) and ACR (FIG. 35B).

The invention claimed is:

1. A method of treating diabetic nephropathy in a subject suffering from type 1 diabetes and diabetic nephropathy, the method comprising administering to the subject an effective amount of a compound that inhibits VEGF-B signaling, wherein the compound is a nucleotide or is a protein comprising an antibody variable region that binds to or specifically binds to VEGF-B and neutralizes VEGF-B signaling.

2. A method of delaying the progression of diabetic nephropathy in a subject suffering from type 1 diabetes and microalbuminuria or macroalbuminuria, the method comprising administering to the subject an effective amount of a compound that inhibits VEGF-B signaling, wherein the compound is a nucleotide or is a protein comprising an antibody variable region that binds to or specifically binds to VEGF-B and neutralizes VEGF-B signaling.

3. The method of claim 1, wherein the compound is administered in an amount effective to have one or more of the following effects:
   (a) reduce or delay progression of hypertension;
   (b) reduce or delay progression of glomerular and/or tubular sclerosis;
   (c) reduce or delay progression of mesangial extracellular matrix deposition and/or abnormal thickening of the glomerular basement membrane;
   (d) reduce or delay progression of glomerular mesangial expansion;
   (e) reduce or delay progression of glomerular vascular rearrangements;
   (f) reduce or delay progression of renal lipid accumulation;
   (g) reduce or delay progression of glomerular lipid accumulation;
   (h) reduce or delay progression of glomerular collagen deposits and/or arteriolar hyaliosis; and/or
   (i) reduce or delay progression of macroalbuminuria.

4. The method of claim 1, wherein the compound is a protein comprising a Fv.

5. The method of claim 4, wherein the protein is selected from the group consisting of:
   (a) a single chain Fv fragment (scFv);
   (b) a dimeric scFv (di-scFv); or
   (c) a diabody;
   (d) a triabody;
   (e) a tetrabody;
   (f) a Fab;
   (g) a $F(ab')_2$;
   (h) a Fv;
   (i) one of (a) to (h) linked to a constant region of an antibody, Fc or a heavy chain constant domain ($C_H$) 2 and/or $C_H3$; or
   (j) an antibody.

6. The method of claim 1, wherein the compound is a protein comprising an antibody variable region that competitively inhibits the binding of antibody 2H10(comprising a heavy chain variable region ($V_H$) comprising a sequence set forth in SEQ ID NO: 2 and a light chain variable region ($V_L$) comprising a sequence set forth in SEQ ID NO: 3) to VEGF-B.

7. The method of claim 6, wherein the compound is a protein comprising a humanized form of a variable region of antibody 2H10 or the compound is a humanized form of antibody 2H10.

8. The method of claim 7, wherein the compound is an antibody comprising a $V_H$ comprising a sequence set forth in SEQ ID NO: 5 and a $V_L$ comprising a sequence set forth in SEQ ID NO: 6.

9. The method of claim 1, wherein the compound that inhibits VEGF-B signaling reduces expression of VEGF-B.

10. The method of claim 9, wherein the compound is selected from the group an antisense, a siRNA, a RNAi, a ribozyme and a DNAzyme.

11. The method of claim 1, additionally comprising administering a further compound to treat the nephropathy or to treat or delay progression of diabetes.

* * * * *